(12) United States Patent
Purandare et al.

(10) Patent No.: US 11,485,741 B2
(45) Date of Patent: Nov. 1, 2022

(54) MACROCYCLIC TOLL-LIKE RECEPTOR 7 (TLR7) AGONISTS

(71) Applicant: BRISTOL-MYERS SQUIBB COMPANY, Princeton, NJ (US)

(72) Inventors: Ashok V. Purandare, Pennington, NJ (US); Honghe Wan, Pennington, NJ (US); Liqi He, San Jose, CA (US); Sanjeev Gangwar, Foster City, CA (US); Shoshana L. Posy, Highland Park, NJ (US); Yam B. Poudel, Fremont, CA (US); Prasanna Sivaprakasam, Lawrenceville, NJ (US); Naidu S. Chowdari, Dublin, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 17/043,886

(22) PCT Filed: Apr. 23, 2019

(86) PCT No.: PCT/US2019/028697
§ 371 (c)(1),
(2) Date: Sep. 30, 2020

(87) PCT Pub. No.: WO2019/209811
PCT Pub. Date: Oct. 31, 2019

(65) Prior Publication Data
US 2021/0053979 A1 Feb. 25, 2021

Related U.S. Application Data

(60) Provisional application No. 62/661,736, filed on Apr. 24, 2018.

(51) Int. Cl.
*C07D 487/16* (2006.01)
*A61K 47/60* (2017.01)

(52) U.S. Cl.
CPC ............ *C07D 487/16* (2013.01); *A61K 47/60* (2017.08)

(58) Field of Classification Search
CPC .............................. C07D 487/16; A61K 47/60
See application file for complete search history.

(56) References Cited

U.S. PATENT DOCUMENTS

| | | | |
|---|---|---|---|
| 6,028,076 A | 2/2000 | Hirota et al. | |
| 6,376,501 B1 | 4/2002 | Isobe et al. | |
| 7,241,890 B2 | 7/2007 | Kasibhatla et al. | |
| 7,521,454 B2 | 4/2009 | Isobe et al. | |
| 7,642,350 B2 | 1/2010 | Pryde | |
| 7,691,877 B2 | 4/2010 | Jones | |
| 8,148,371 B2 | 4/2012 | Isobe et al. | |
| 8,729,088 B2 | 5/2014 | Carson et al. | |
| 8,993,755 B2 | 3/2015 | Graupe et al. | |
| 9,050,376 B2 | 6/2015 | Carson et al. | |
| 9,127,006 B2 | 9/2015 | Desai et al. | |
| 9,161,934 B2 | 10/2015 | Halcomb et al. | |
| 9,173,935 B2 | 11/2015 | Maj et al. | |
| 9,295,732 B2 | 3/2016 | Lioux et al. | |
| 9,499,549 B2 | 11/2016 | Mcgowan | |
| 9,662,336 B2 | 5/2017 | Coe | |
| 9,902,730 B2 | 2/2018 | Li et al. | |
| 9,944,649 B2 | 4/2018 | Cortez | |
| 2007/0225303 A1 | 9/2007 | Ogita et al. | |
| 2009/0105212 A1 | 4/2009 | Isobe et al. | |
| 2009/0118263 A1 | 5/2009 | Hashimoto et al. | |
| 2011/0028715 A1 | 2/2011 | Isobe et al. | |
| 2012/0003298 A1 | 1/2012 | Barberis et al. | |
| 2012/0083473 A1 | 4/2012 | Holldack et al. | |
| 2012/0231023 A1 | 9/2012 | Rawski et al. | |
| 2012/0302598 A1 | 11/2012 | Jones | |
| 2013/0202629 A1 | 8/2013 | Carson et al. | |
| 2014/0141033 A1 | 5/2014 | Vernejoul et al. | |
| 2014/0323441 A1 | 10/2014 | Bonfanti et al. | |
| 2015/0299221 A1 | 10/2015 | Bonfanti et al. | |

(Continued)

FOREIGN PATENT DOCUMENTS

EP 3546457 A1 10/2019
JP 2004137157 A 5/2004

(Continued)

OTHER PUBLICATIONS

Akinbobuyi et al., Facile syntheses of functionalized toll-like receptor 7 agonists, 2015, 459-460, 56, Tetrahedron Letters.
Akinbobuyi et al., Synthesis and immunostimulatory activity of substituted TLR7 agonists, 2016, 4246-4249, 26, Bioorganic & Medicinal Chemistry Letters.
Beesu et al., Identification of High-Potency Human TLR8 and Dual TLR7/TLR8 Agonists in Pyrimidine-2,4-diamines, 2017, 2084-2098, 60, J Med Chem.
Berghofer et al., Natural and Synthetic TLR7 Ligands Inhibit CpG-A- and CpG-C-Oligodeoxynucleotide-Induced IFN . . . , 2007, 4072-4079, 178, The Journal of Immunology.
Chan et al., Synthesis and Characterization of PEGylated Toll Like Receptor 7 Ligands, 2011, 445-454, 22, Bioconugate Chemistry.

(Continued)

*Primary Examiner* — Alicia L Otton
(74) *Attorney, Agent, or Firm* — Joseph F. Reidy; Yuan Chao

(57) ABSTRACT

Compounds having a structure according to formula are modulators of TLR7 activity and can be used to treat conditions amenable to treatment by the modulation of TLR7 activity.

(I)

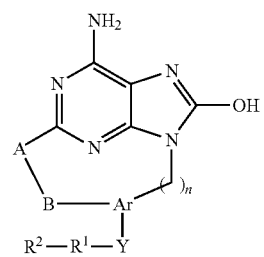

18 Claims, 17 Drawing Sheets

(56) References Cited

U.S. PATENT DOCUMENTS

| | | |
|---|---|---|
| 2016/0168150 A1 | 6/2016 | Me |
| 2016/0199499 A1 | 7/2016 | Carson et al. |
| 2016/0304531 A1 | 10/2016 | Bonfanti et al. |
| 2017/0121421 A1 | 5/2017 | Cortez et al. |
| 2017/0273983 A1 | 9/2017 | Ding et al. |
| 2019/0055245 A1 | 2/2019 | Poudel |
| 2019/0055246 A1 | 2/2019 | He |
| 2019/0055247 A1 | 2/2019 | He |

FOREIGN PATENT DOCUMENTS

| | | | |
|---|---|---|---|
| WO | 2007028129 A1 | 3/2007 | |
| WO | WO 2014009509 | * 1/2014 | ........... C07D 487/16 |
| WO | 2015036044 A1 | 3/2015 | |
| WO | 2016107536 A1 | 7/2016 | |
| WO | 2017076346 A1 | 5/2017 | |
| WO | 2017216293 A1 | 12/2017 | |
| WO | 2018095426 A1 | 5/2018 | |

OTHER PUBLICATIONS

Chan et al., Synthesis and Immunological Characterization of Toll-Like Receptor 7 Agonistic Conjugates, 2009, 1194-_1200, vol. 20, Bioconjugate Chemistry.

Embrechts et al., 2,4-Diaminoquinazolines as Dual Toll-like Receptor (TLR) 7/8 Modulators for the Treatment of Hepatitis B Virus, 2018, 6236_6246, 61, Journal of Medicinal Chemistry.

Gadd et al., Targeted Activation of Toll-Like Receptors: Conjugation of a Toll-Like Receptor 7 Agonist to a Monoclonal Antibody Maintains Antigen Binding and Specificity, 2015, 1743_1752, 26, Bioconjugate Chemistry.

Gianluca Papeo, MutT Homolog 1 (MTH1): The Silencing of a Target, Journal of Medicinal Chemistry, Mar. 24, 2016, pp. 2343-2345, vol. 59, No. 6.

Haoyu S. Yu et al., Accurate and Reliable Prediction of the Binding Affinities of Macrocycles to Their Protein Targets, Journal of Chemical Theory and Computation, Nov. 30, 2017, pp. 6290-6300, vol. 13, No. 12.

International Search Report; dated Jul. 3, 2019.

Isobe et al., Synthesis and Biological Evaluation of Novel 9-Substituted-8-Hydroxyadenine Derivatives as Potent nterferon Inducers, 2006, 2088-2095,49, J Med Chem.

James S. Scott et al., Practical application of ligand efficiency metrics in lead optimisation, Bioorganic & Medicina Chemistry, Jul. 1, 2018, pp. 3006-3015, vol. 26, No. 11.

Jason G. Kettle et al., Potent and Selective Inhibitors of MTH1 Probe Its Role in Cancer CellSurvival, Journal of Medicinal Chemistry, Mar. 24, 2016, pp. 2346-2361, 59, No. 6.

Koga-Yamakawa et al., Intratracheal and oral administration of SM-276001: A selective TLR7 agonist, leads to antitumor efficacy in primary and metastatic models of cancer, 2013, 580-590, 132, IJC Cancer.

Lund et al., Recognition of single-stranded RNA viruses by Toll-like receptor 7, 2004, 5598-5603, 101:15, ProcNatlAcadSciUSA.

McGowan et al., Identification and Optimization of Pyrrolo[3,2-d]pyrimidine Toll-like Receptor 7 (TLR7) Selective Agonists for the Treatment of Hepatitis B, 2017, 6137-6151, 60, J Med Chem.

Musmuca et al., Small-Molecule Interferon Inducers. Toward the Comprehension of the Molecular Determinants through Ligand-Based Approaches, 2009, 1777-1786,49, J Chem Inform Model.

Nakamura et al., Synthesis and evaluation of 8-oxoadenine derivatives as potent Toll-like receptor 7 agonists with nigh water solubility, 2013, 669-672, 23, BioorgMedChemLett.

Vincent Wagner et al., Computational Macrocyclization:From de novo Macrocycle Generation to Binding Affinity Estimation, ChemMedChem, Oct. 25, 2017, pp. 1866-1872, vol. 12, No. 22.

Yoshiaki, JP2004137157_abst, 2004.

Yu et al., Toll-Like Receptor 7 Agonists: Chemical Feature Based Pharmacophore Identification and Molecular Docking Studies, 2013, 1-12, Plossone.

Zhang et al., Structural Analysis Reveals that Toll-like Receptor 7 Is a Dual Receptor for Guanosine and Single-Stranded RNA, 2016, 737_748, 45, Immunity.

* cited by examiner

BINDING OF COMPOUND IIa-02 TO TLR7

Linker Compound 1

MACROCYCLIC TOLL-LIKE RECEPTOR 7 (TLR7) AGONISTS

CROSS-REFERENCE TO RELATED APPLICATIONS

This application claims the benefit under 35 U.S.C. § 119(e) of U.S. Provisional Application Ser. No. 62/661,736, filed Apr. 24, 2018; the disclosure of which is incorporated herein by reference.

BACKGROUND OF THE INVENTION

This disclosure relates to Toll-like receptor 7 ("TLR7") agonists and conjugates thereof, and methods for the preparation and use of such agonists and their conjugates.

Toll-like receptors ("TLRs") are cell-surface receptors that recognize pathogen-associated molecular patterns ("PAMPs"). Activation of a TLR by the binding of its cognate PAMP signals potential infection by a pathogen and stimulates the immune system to fight the infection. Humans have 11 TLRs, named TLR1 through TLR11.

The activation of a TLR—with TLR7 being the most studied—by an agonist can have an adjuvant effect on the action of vaccines and immunotherapy agents in treating a variety of conditions other than actual pathogen infection, by stimulating the immune response.

TLR7 recognizes PAMPs associated with single-stranded RNA viruses. Its activation induces secretion of Type I interferons such as IFNα and IFNβ (Lund et al. 2004). It has two binding sites, one for single stranded RNA ligands such as ssRNA40 (Berghöfer et al. 2007) and one for guanosine (Zhang et al. 2016).

TLR7 can bind to, and be activated by, guanosine-like synthetic agonists such as imiquimod, resiquimod, and gardiquimod, which are based on a 1H-imidazo[4,5-c]quinoline scaffold.

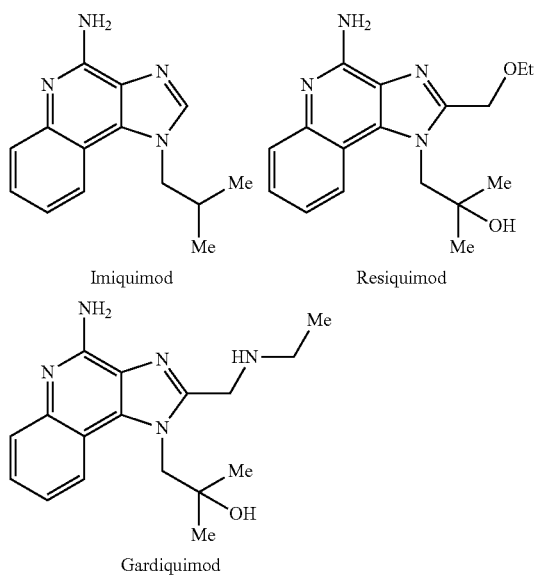

Imiquimod

Resiquimod

Gardiquimod

Synthetic TLR7 agonists based on a pteridinone molecular scaffold are also known, as exemplified by vesatolimod (Desai et al. 2015), which has been in Phase 2 clinical trials.

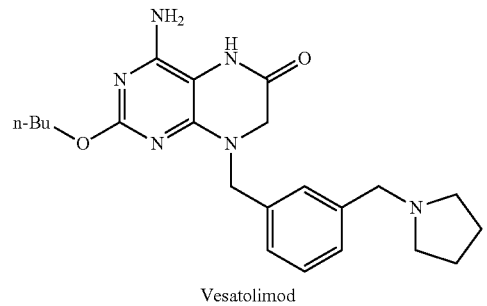

Vesatolimod

Other synthetic TLR7 agonists are based on a purine-like scaffold, frequently according to formula (A):

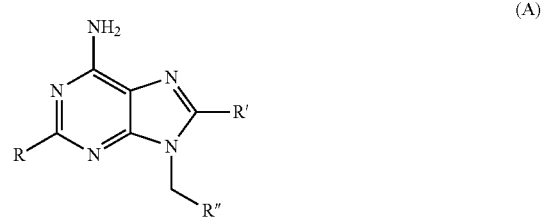

where R, R', and R" are structural variables, with R" typically containing an unsubstituted or substituted aromatic or heteroaromatic ring.

Disclosures of bioactive molecules having a purine-like scaffold and their uses in treating conditions such as fibrosis, inflammatory disorders, cancer, or pathogenic infections include: Akinbobuyi et al. 2015 and 2016; Barberis et al. 2012; Carson et al. 2014; Ding et al. 2016, 2017a, and 2017b; Graupe et al. 2015; Hashimoto et al. 2009; He et al. 2019a and 2019b; Holldack et al. 2012; Isobe et al. 2009a and 2012; Poudel et al. 2019a and 2019b; Pryde 2010; and Young et al. 2019.

The group R" can be pyridyl: Bonfanti et al. 2015a and 2015b; Halcomb et al. 2015; Hirota et al. 2000; Isobe et al. 2002, 2004, 2006, 2009a, 2009b, 2011, and 2012; Kasibhatla et al. 2007; Koga-Yamakawa et al. 2013; Musmuca et al. 2009; Nakamura 2012; Ogita et al. 2007; and Yu et al. 2013.

There are disclosures in which the 6,5-fused ring system of formula (A)—a pyrimidine six member ring fused to an imidazole five member ring—is modified. (a) Dellaria et al. 2007, Jones et al. 2010 and 2012, and Pilatte et al. 2017 disclose compounds in which the pyrimidine ring is replaced by a pyridine ring. (b) Coe et al. 2017 and Zhang et al. 2018 disclose compounds in which the imidazole ring is replaced by a pyrazole ring. (c) Cortez et al. 2017 and 2018; Li et al. 2018, and McGowan et al. 2016a, 2016b, and 2017 disclose compounds in which the imidazole ring is replaced by a pyrrole ring.

Bonfanti et al. 2015b and 2016 disclose TLR7 modulators in which the two rings of a purine moiety are spanned by a macrocycle:

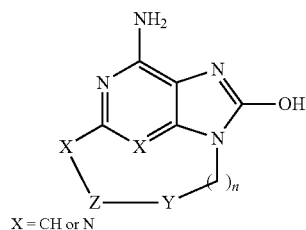

X = CH or N

A TLR7 agonist can be conjugated to a partner molecule, which can be, for example, a phospholipid, a poly(ethylene glycol) ("PEG"), or another TLR (commonly TLR2). Exemplary disclosures include: Carson et al. 2013, 2015, and 2016, Chan et al. 2009 and 2011, Lioux et al. 2016, Maj et al. 2015, Vernejoul et al. 2014, and Zurawski et al. 2012. Conjugation to an antibody has also been disclosed: Gadd et al. 2015. A frequent conjugation site is at the R″ group of formula (A).

Jensen et al. 2015 discloses the use of cationic lipid vehicles for the delivery of TLR7 agonists.

Some TLR7 agonists, including resiquimod are dual TLR7/TLR8 agonists. See, for example, Beesu et al. 2017, Embrechts et al. 2018, Lioux et al. 2016, and Vernejoul et al. 2014.

Full citations for the documents cited herein by first author or inventor and year are listed at the end of this specification.

BRIEF SUMMARY OF THE INVENTION

In one aspect, this specification provides a compound having a structure represented by formula (I)

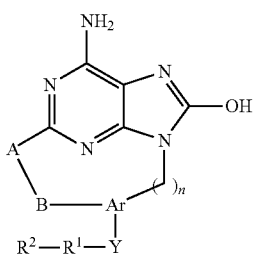

(I)

wherein
A is O, NH, N($C_1$-$C_3$ alkyl), or S;
B is a $C_1$-$C_{10}$ unsaturated or saturated alkyl, ($C_2$-$C_6$ alkyl)NHC(=O)($C_1$-$C_6$ alkyl), ($C_2$-$C_6$ alkyl)NHC(=O)($C_1$-$C_6$ alkyl)O, ($C_2$-$C_{10}$ unsaturated or saturated alkyl)O, ($C_2$-$C_6$ alkyl)O($C_2$-$C_6$ alkyl), ($C_2$-$C_6$ alkyl)O($C_2$-$C_6$ alkyl)O; each optionally substituted with $C_1$-$C_3$ alkyl or ($C_1$-$C_3$ alkyl)O;
Ar is a 6-membered aromatic, a 5- to 6-membered heteroaromatic, a 4- to 7-membered cycloaliphatic, or a 4- to 7-membered heterocycloaliphatic moiety;
Y is a bond, O, S, NH, N($C_1$-$C_3$ alkyl), $(CH_2)_{1-2}$, C(=O)NH, or C(=O)N($C_1$-$C_3$ alkyl);
$R^1$ is a 6-membered aromatic, a 5- to 6-membered heteroaromatic, a 4- to 7-membered cycloaliphatic, or a 4- to 7-membered heterocycloaliphatic moiety, or $R^1$ can be absent if Y is other than a bond;
$R^2$ is H, $C_1$-$C_3$ alkyl, halo, O($C_1$-$C_3$ alkyl), CN, $NO_2$, $(CH_2)_{1-4}R^3$,

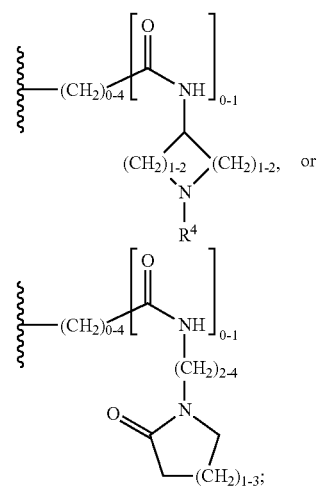

with the proviso that $R^2$ is other than halo, O($C_1$-$C_3$ alkyl), CN, or $NO_2$ when $R^1$ is absent;
$R^3$ is halo, OH, CN, $NH_2$, NH($C_1$-$C_5$ alkyl), $NH(CH_2)N(C_1$-$C_5$ alkyl$)_2$, NH($C_3$-$C_6$ cycloaliphatic), NH($C_4$-$C_8$ bicycloaliphatic), NH($C_6$-$C_{10}$ spirocycloaliphatic), N($C_3$-$C_6$ cycloaliphatic$)_2$, $NH(CH_2)_{1-3}$(aryl), $N((CH_2)_{1-3}$(aryl)$)_2$, $NH(CH_2)_{1-3}CO_2(C_1$-$C_3$ alkyl), $N((CH_2)_{1-3}CO_2(C_1$-$C_3$ alkyl)$)_2$, or a cyclic amine moiety having the structure

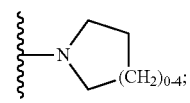

$R^4$ is H, $C_1$-$C_3$ alkyl, or C(=O)($C_1$-$C_3$ alkyl); and
n is 1, 2, or 3;
wherein
an alkyl, cycloaliphatic, bicycloaliphatic, spirocycloaliphatic, cyclic amine, 6-membered aromatic or heteroaromatic, or 5-membered heteroaromatic moiety is optionally substituted with one or more substituents selected from OH, halo, CN, ($C_1$-$C_3$ alkyl), O($C_1$-$C_3$ alkyl), C(=O)($C_1$-$C_3$ alkyl), $SO_2$($C_1$-$C_3$ alkyl), $CO_2$($C_1$-$C_3$ alkyl), $NH_2$, NH($C_1$-$C_3$ alkyl), and N($C_1$-$C_3$ alkyl$)_2$;
a cycloaliphatic, bicycloaliphatic, spirocycloaliphatic, or cyclic amine moiety may have a $CH_2$ group replaced by O, S, NH, C(=O), N($C_1$-$C_3$ alkyl), NC(=O)($C_1$-$C_3$ alkyl), or N(Boc); and
a cycloaliphatic, heterocycloaliphatic, aromatic, or heteroaromatic moiety may be fused to another cycloaliphatic, heterocycloaliphatic, aromatic, or heteroaromatic moiety.

Compounds according to formula (I) have activity as TLR7 agonists and some of them can be conjugated to a targeting agent such as an antibody, for targeted delivery to a target tissue or organ of intended action. They can also be PEGylated, to modulate their pharmaceutical properties.

BRIEF DESCRIPTION OF THE DRAWING(S)

FIGS. 1A-1B, 2A-2B, 3, 4, 5, 6, 7, 8, 9, and 10 show different schemes for the synthesis of compounds disclosed herein.

DETAILED DESCRIPTION OF THE INVENTION

Definitions

Figure 1A:
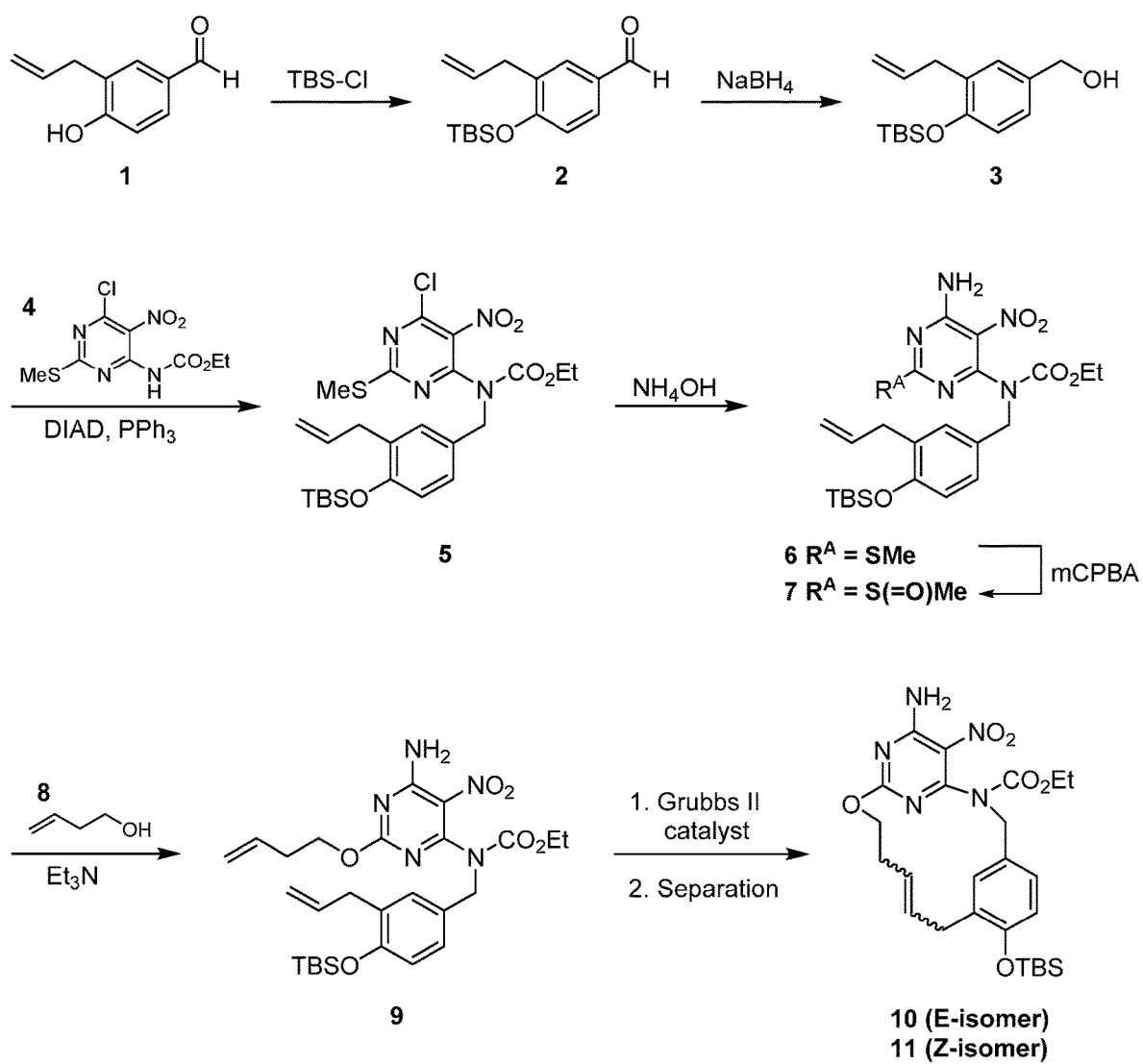

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et a. (1988) *Proc. Nat. Acad. Sci. USA* 85:5879-5883). Such single chain antibodies are also encompassed within the term "antigen-binding portion" of an antibody.

Unless indicated otherwise—for example by reference to the linear numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $C_{H3}$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like.

Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyloxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~ ) transverse to a bond or an asterisk (*) at the end of the bond denotes a covalent attachment site. For instance, a statement that R is

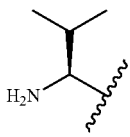

or that R is

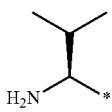

in the formula

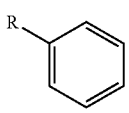

means

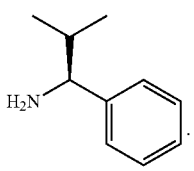

In the formulae of this specification, a bond traversing an aromatic or heteroaromatic ring between two carbons thereof means that the group attached to the bond may be located at any of the positions of the aromatic or heteroaromatic ring made available by removal of a hydrogen that is explicitly or implicitly there. By way of illustration, the formula

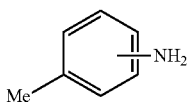

represents

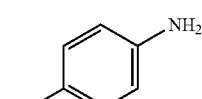

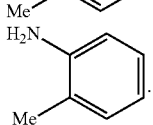

In other illustrations,

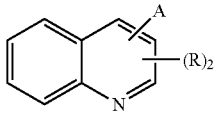

represents

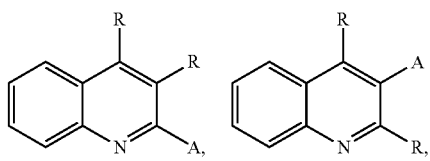

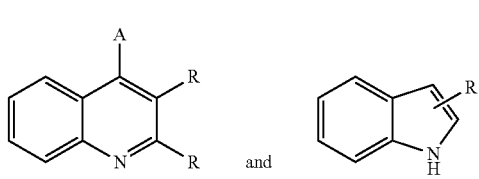

represents

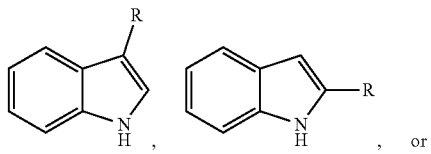

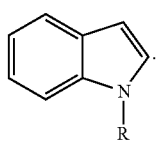

Generally, tautomeric structures have been rendered herein in the enol form, as a matter of consistency and convenience.

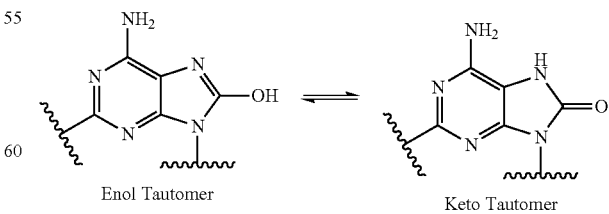

Enol Tautomer    Keto Tautomer

Those skilled in the art will appreciate that they could also have be rendered in the equivalent keto form and that the two tautomers equivalent.

Compounds

In one embodiment, compounds according to formula (I) have a structure represented by formula (II)

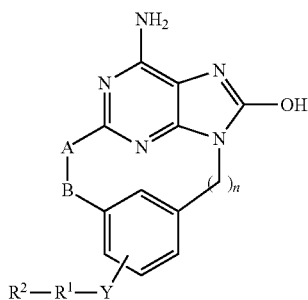
(II)

where A, B, Y, $R^1$, $R^2$ and n are as defined in respect of formula (I).

In one embodiment, compounds according to formula (I) have a structure represented by formula (IIa) where A, B, and $R^2$ are as defined in respect of formula (I):

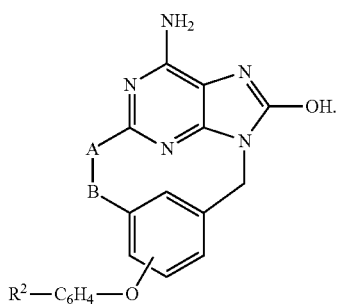
(IIa)

Examples of compounds according to formula (IIa) include:

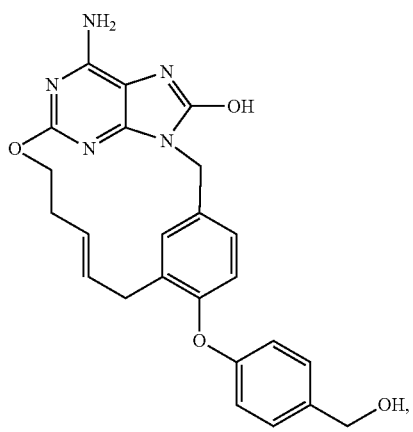
(IIa-01)

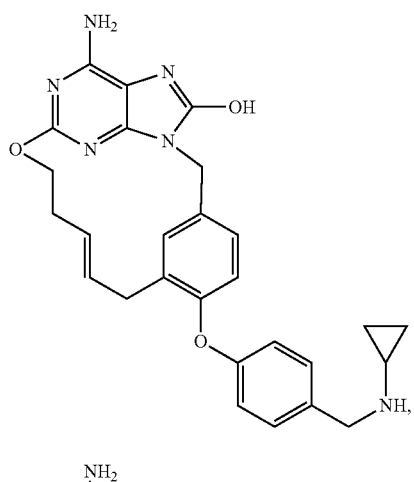
(IIa-02)

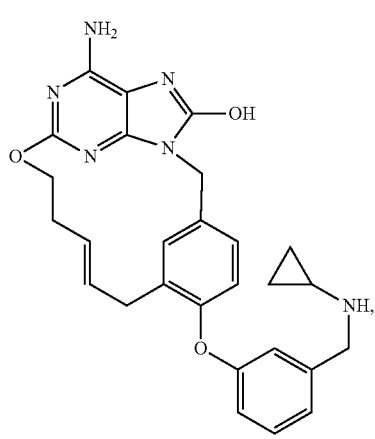
(IIa-03)

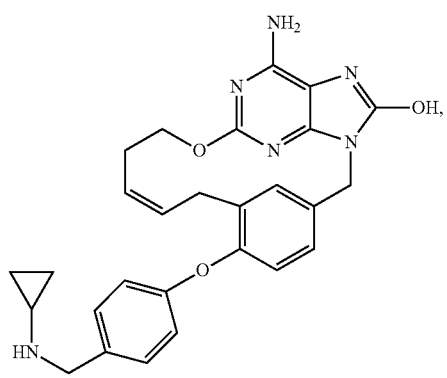
(IIa-04)

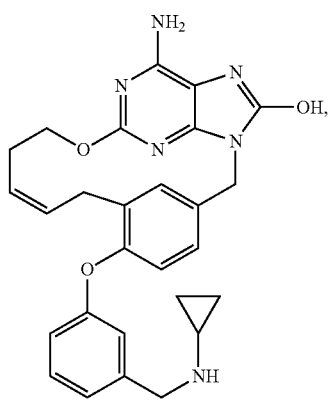
(IIa-05)

(IIa-06)
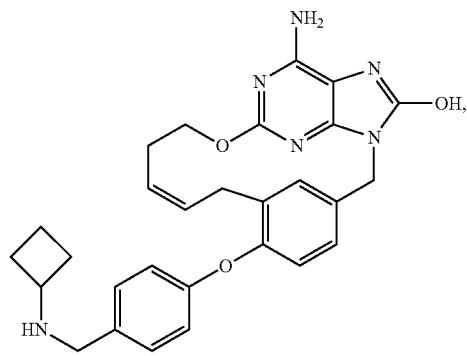
(IIa-07)
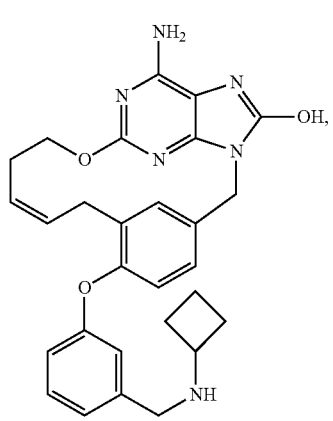
(IIa-08)
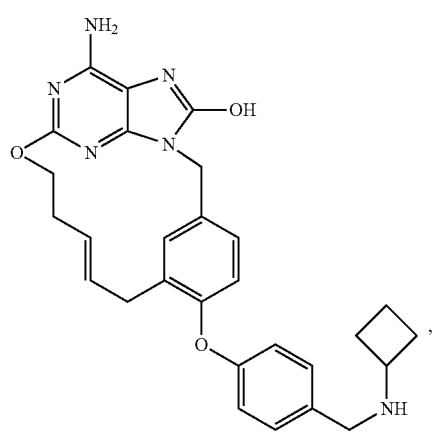
(IIa-09)
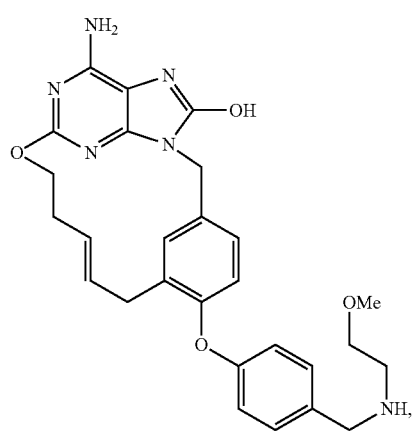
(IIa-10)
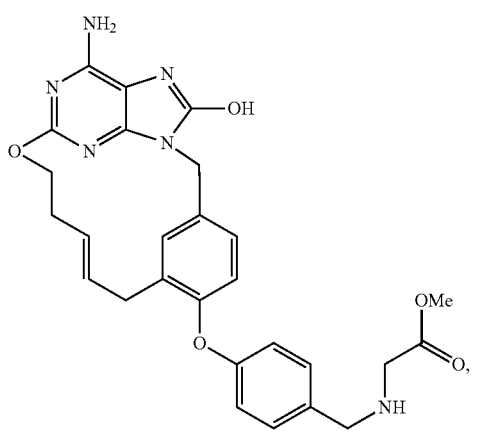
(IIa-11)
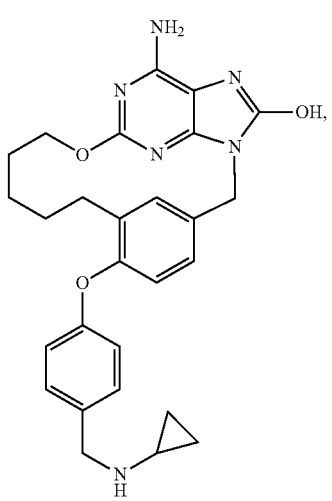
(IIa-12)

(IIa-13)
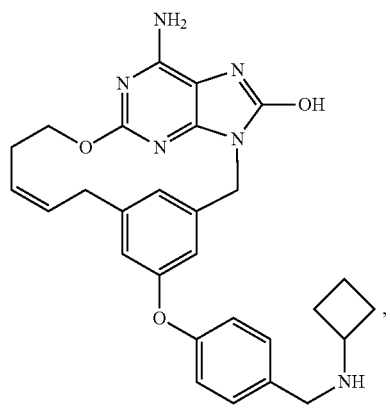
(IIa-14)
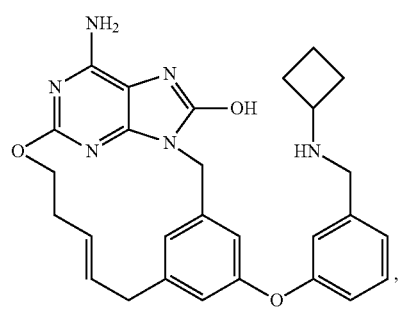
(IIa-15)
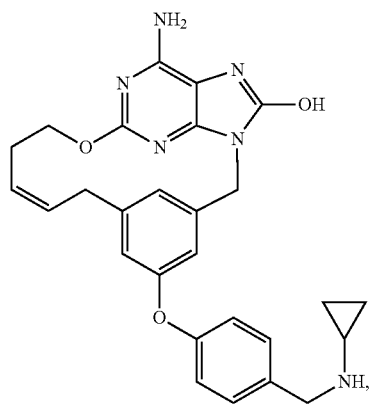
(IIa-16)
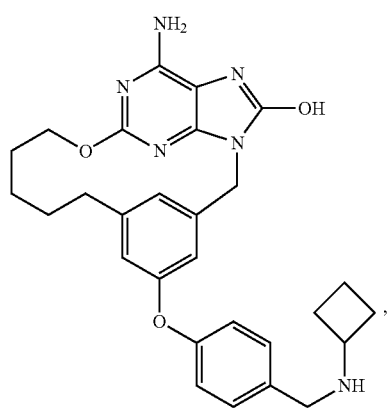
(IIa-17)
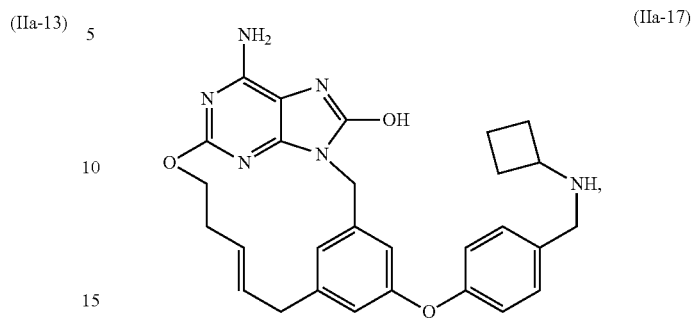
(IIa-18)
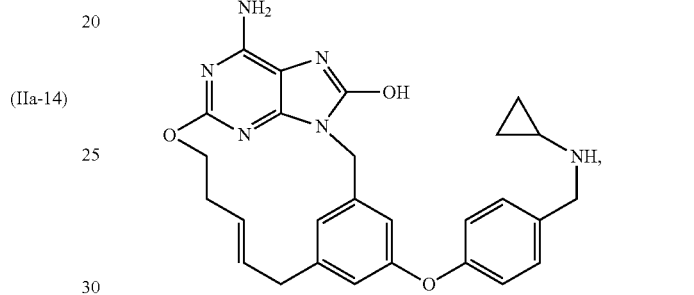
(IIa-19)
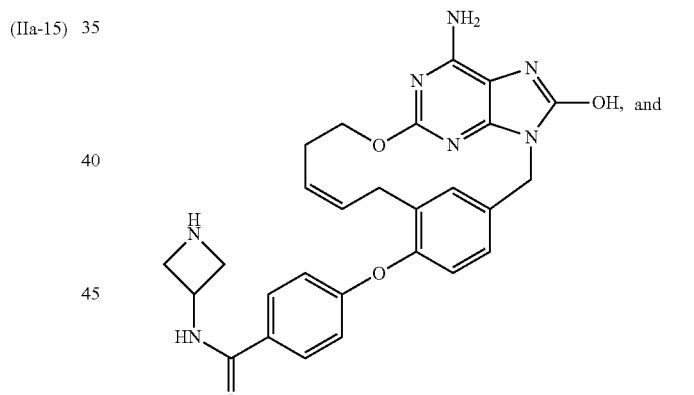
(IIa-20)
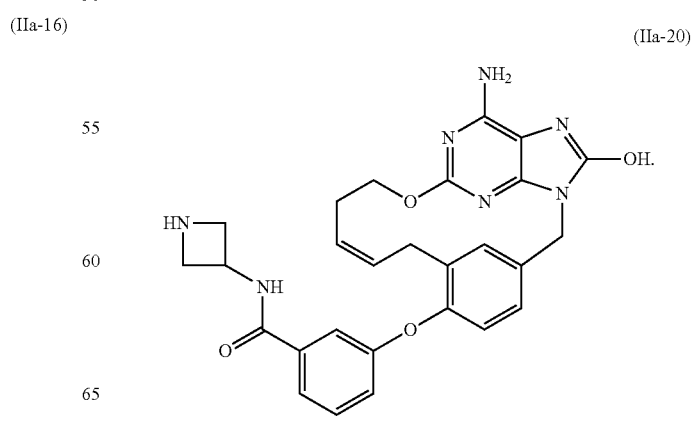

In one embodiment, compounds according to formula (I) have a structure represented by formula (IIb)

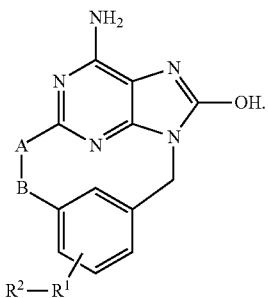
(IIb)

where A, B, and R² are as defined in respect of formula (I) and R¹ is a phenyl, 6-membered heteroaromatic, or 5-membered heteroaromatic moiety. Where R¹ is a 6-membered heteroaromatic moiety, it can be selected from selected a pyridine, pyrazine, or pyridazine moiety. Where R¹ is a 5-membered heteroaromatic moiety, it can be selected from pyrrolyl, furanyl, thiophenyl, pyrazolyl, imidazolyl, oxazolyl, isoxazolyl, 1,2,3-triazolyl, 1,2,4-triazolyl, tetrazolyl, 1,2,4-oxadiazolyl, 1,2,4-thiadiazolyl, 1,3,4-oxadiazolyl, 1,3,4-thiadiazolyl, 1,2,5-oxadiazolyl, 1,2,5-thiadiazolyl, 1,2,3,4-oxatiazolyl, and 1,2,3,4-thiatriazolyl.

Preferably, R¹ is

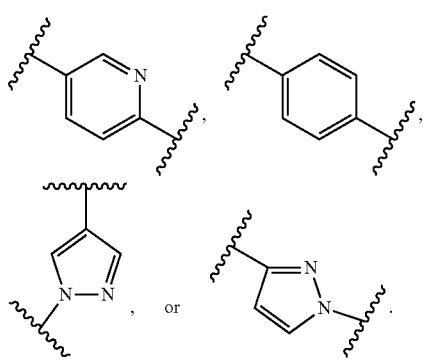

Examples of compounds according to formula (IIb) include:

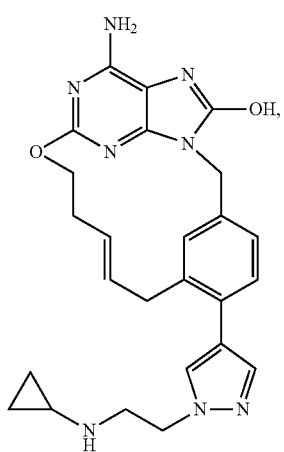
(IIb-01)

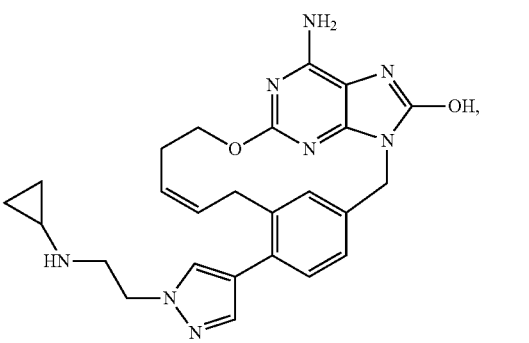
(IIb-02)

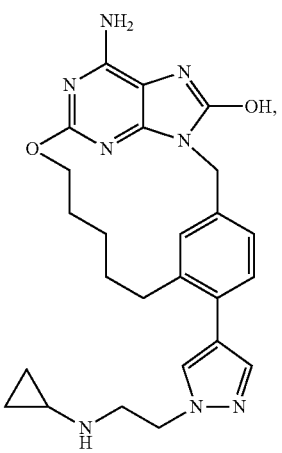
(IIb-03)

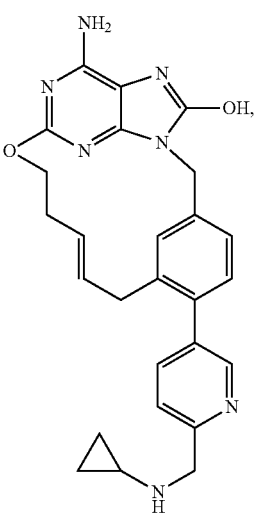
(IIb-04)

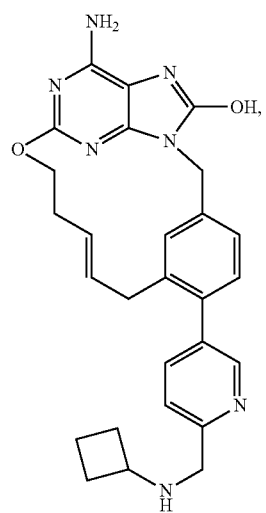
(IIb-05)
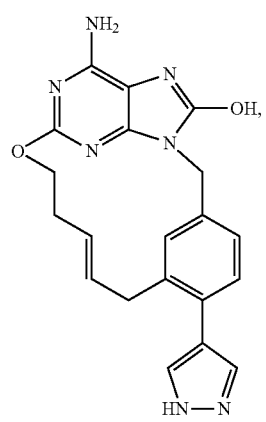
(IIb-06)
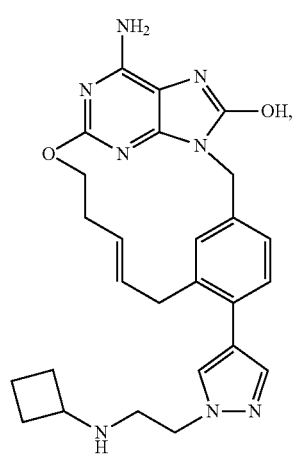
(IIb-07)
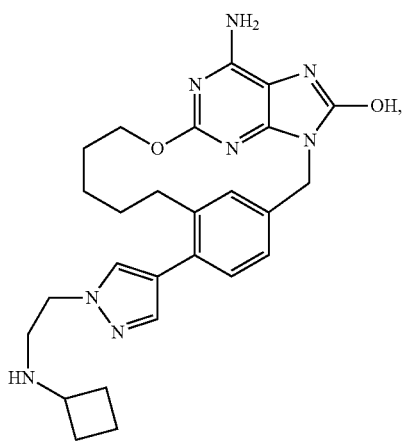
(IIb-08)
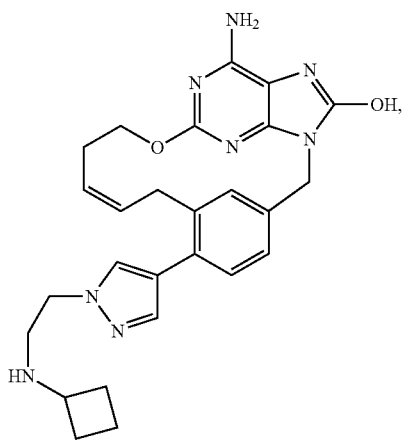
(IIb-09)
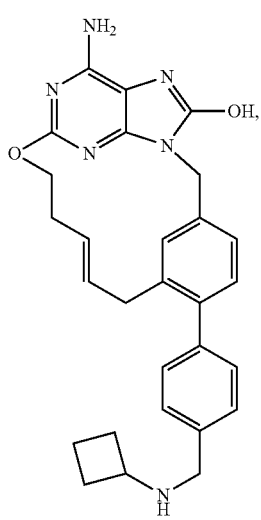
(IIb-10)

23
-continued
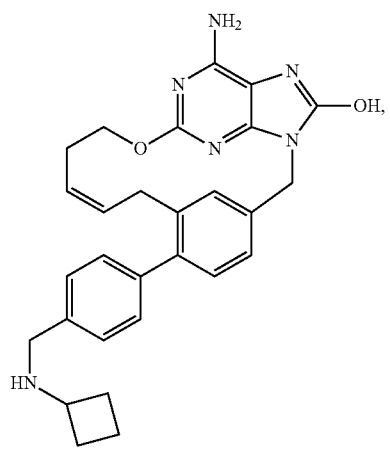
(IIb-11)
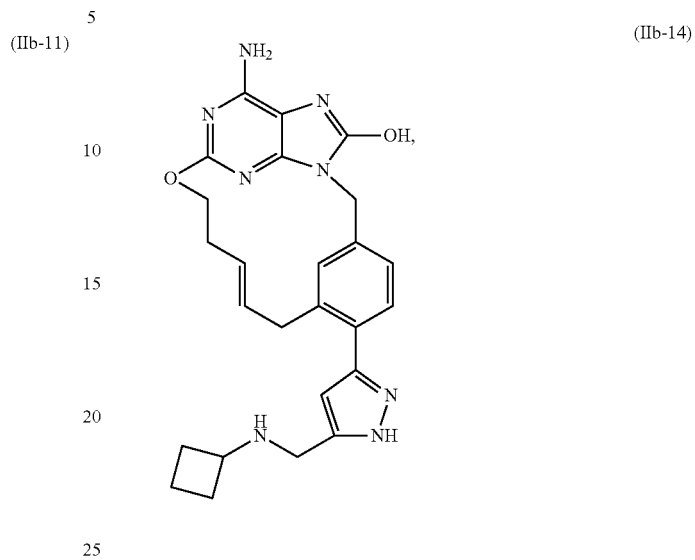
(IIb-14)
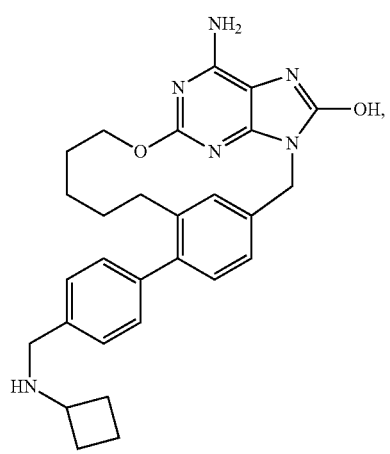
(IIb-12)
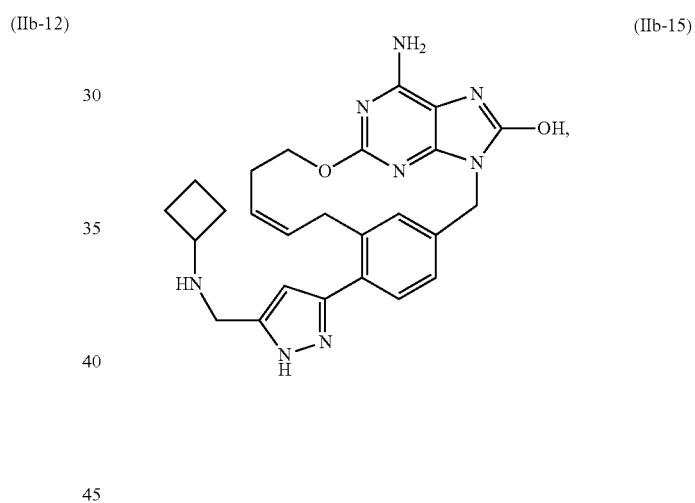
(IIb-15)
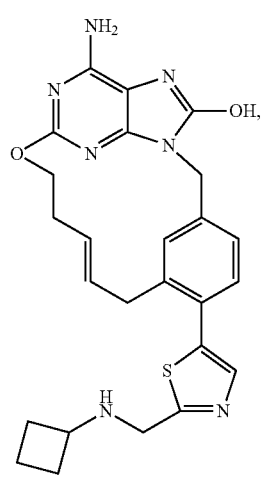
(IIb-13)
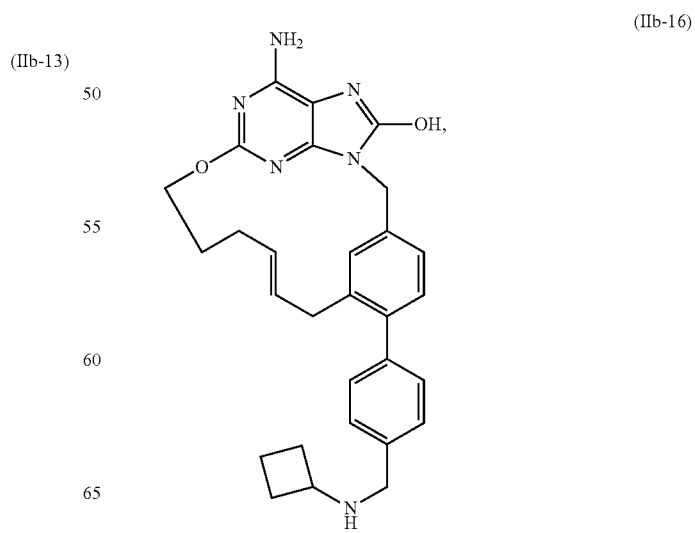
(IIb-16)

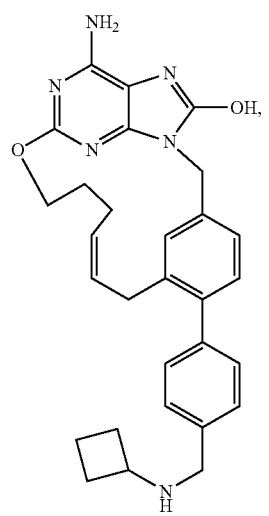
(IIb-17)
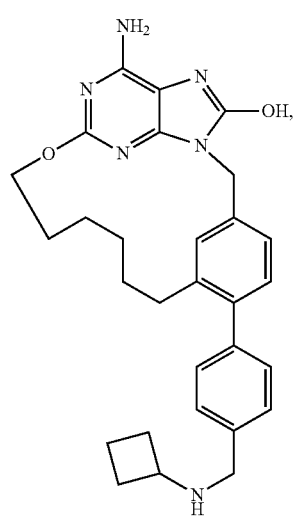
(IIb-18)
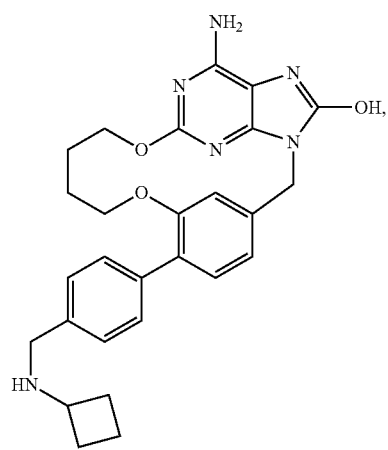
(IIb-19)
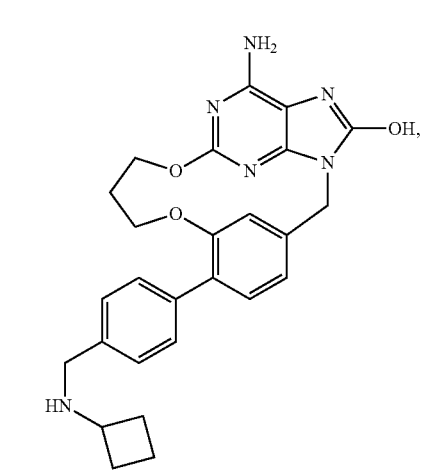
(IIb-20)
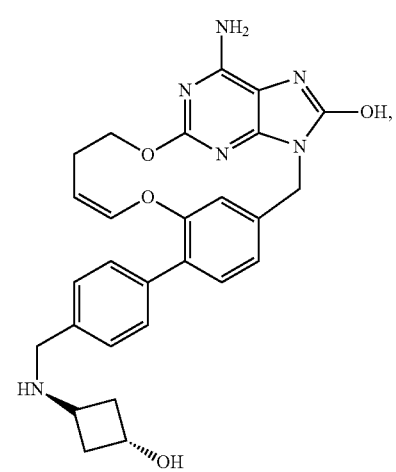
(IIb-21)
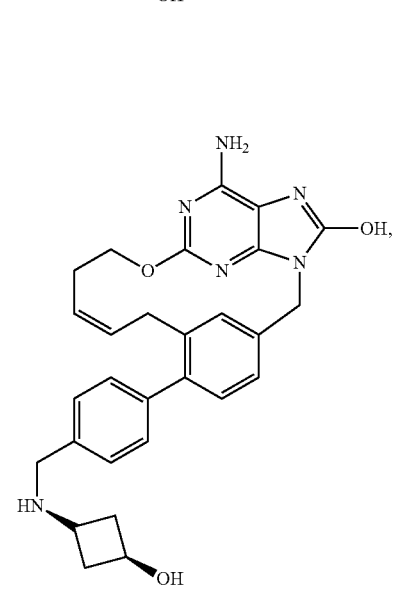
(IIb-22)

27
-continued
(IIb-23)
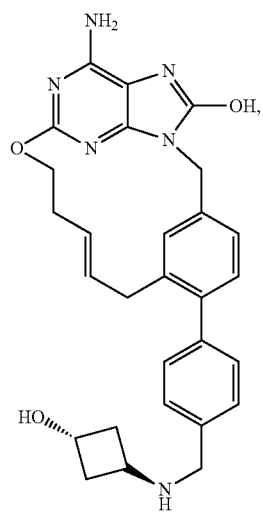
(IIb-24)
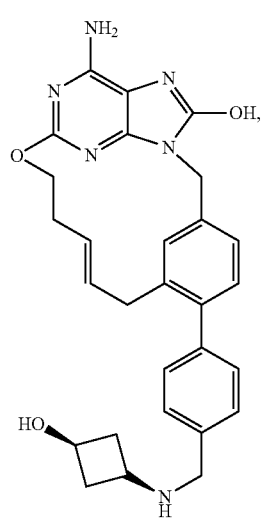
(IIb-25)
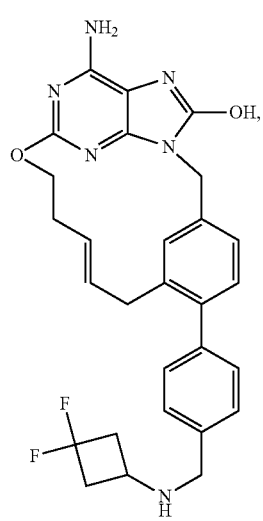
28
-continued
(IIb-26)
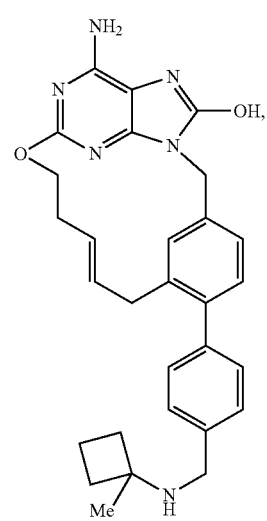
(IIb-27)
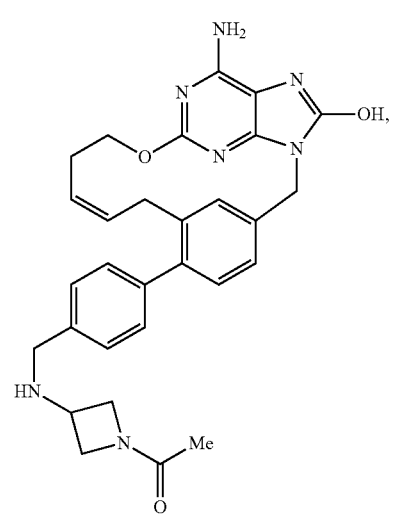
(IIb-28)
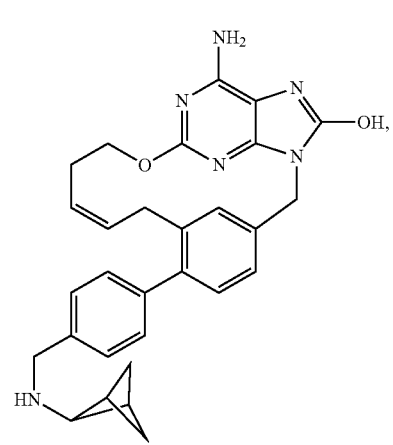

-continued
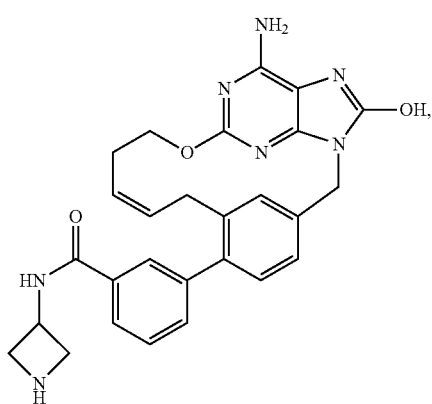
(IIb-29)
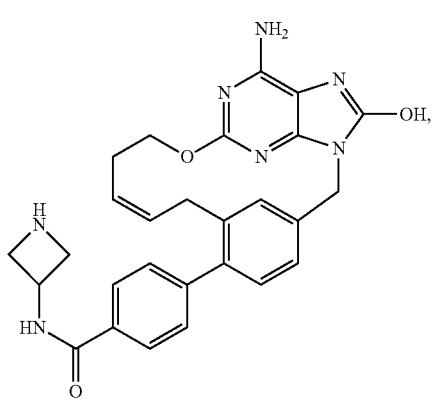
(IIb-30)
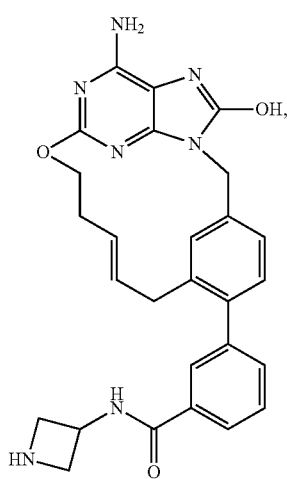
(IIb-31)
-continued
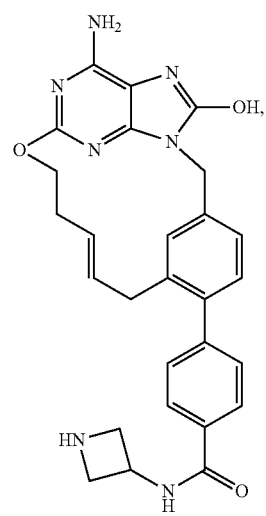
(IIb-32)
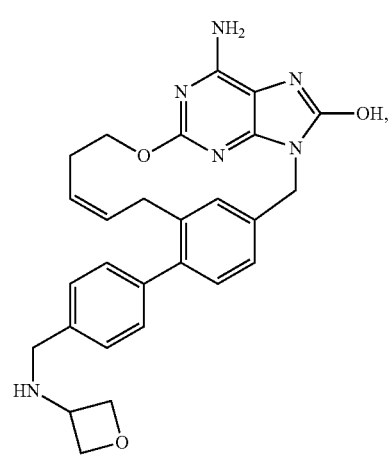
(IIb-33)
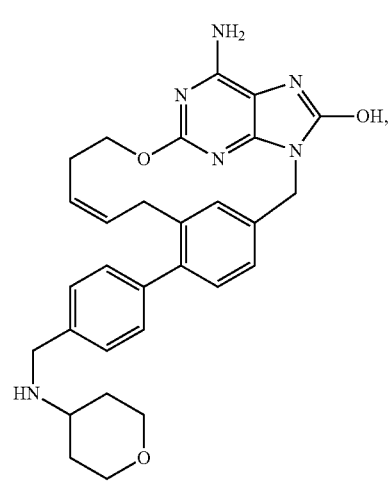
(IIb-34)

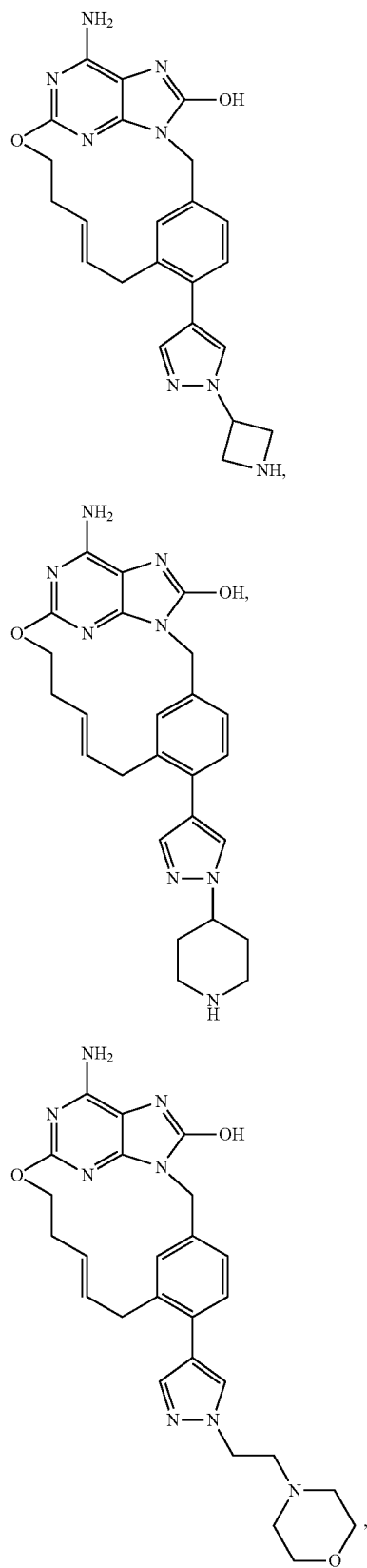
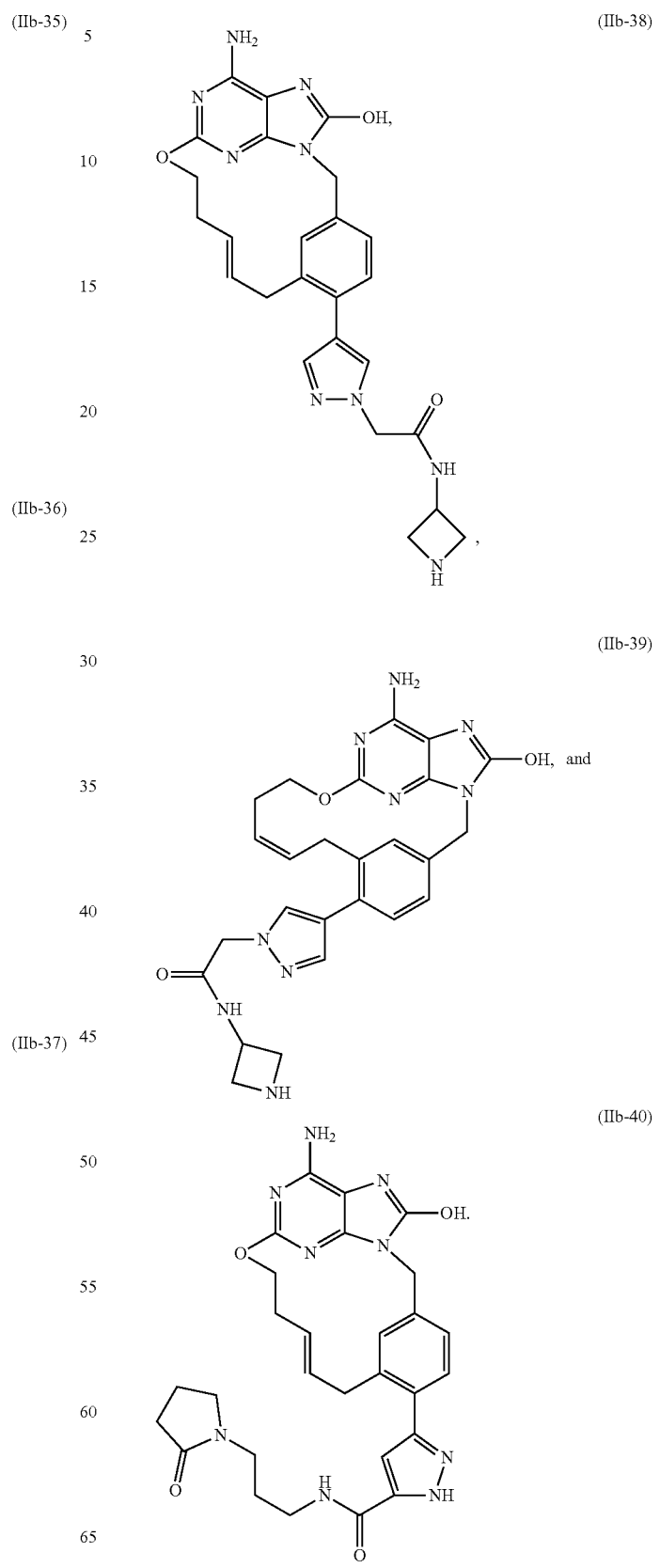

In one embodiment, compounds according to formula (I) have a structure represented by formula (IIc)

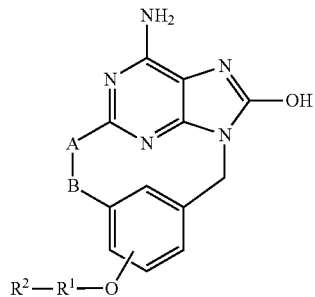
(IIc)

where A, B, and R² are as defined in respect of formula (I) and R¹ is a 4- to 7-membered heterocycloaliphatic moiety. Examples compounds according to formula (IIc) are (IIc-01) and (IIc-02):

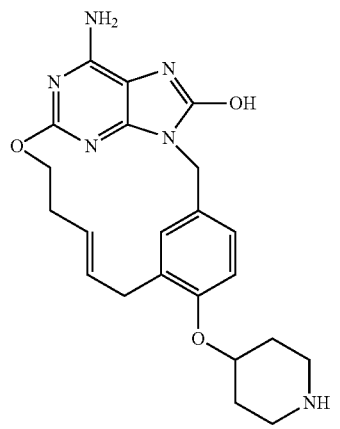
(IIc-01)

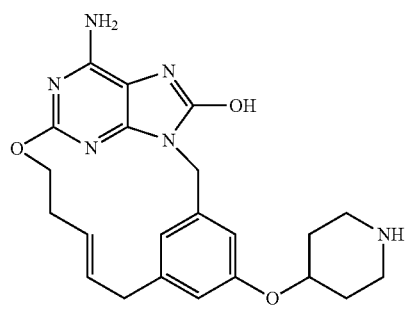
(IIc-02)

In one embodiment, compounds according to formula (I) have a structure represented by formula (IId)

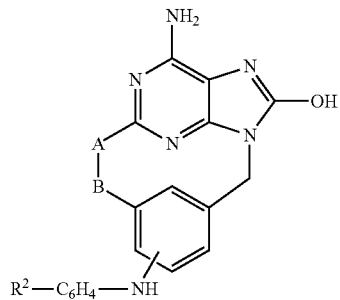
(IId)

where A, B, and R² are as defined in respect of formula (I). An example of a compound according to formula (IId) is (IId-01).

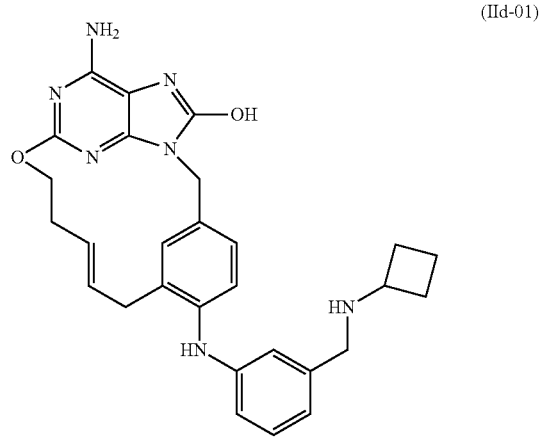 [SMILES: Nc1nc2nc3c1nc(O)n3Cc1ccc(Nc3cccc(CNC4CCC4)c3)c(c1)C/C=C/CCO2]
(IId-01)

An embodiment in which R¹ is absent is represented by formula (IIe)

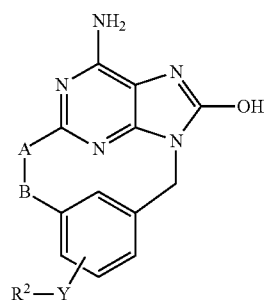
(IIe)

where A, B, Y, and R² are as defined in respect of formula (I), with Y preferably being O. Examples of compounds according to formula (IIe) are compounds (IIe-01) and (IIe-02):

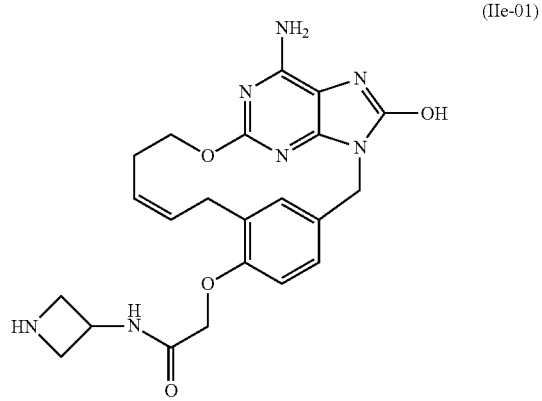
(IIe-01)

-continued (IIe-02)

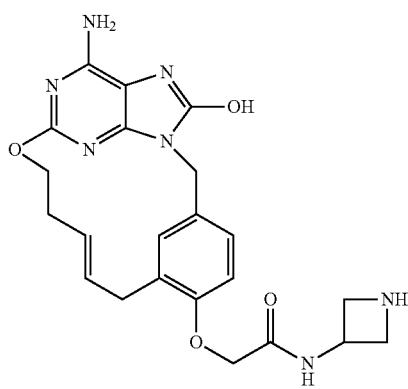

In formula (I), Ar preferably is phenyl, pyridine, pyrazine, or pyridazine moiety.

In formulae (I) and (II), preferably n is 1.

In formulae (I), (II), (IIa), (IIb), (IIc), (IId), and (IIe), preferably -A-B— is

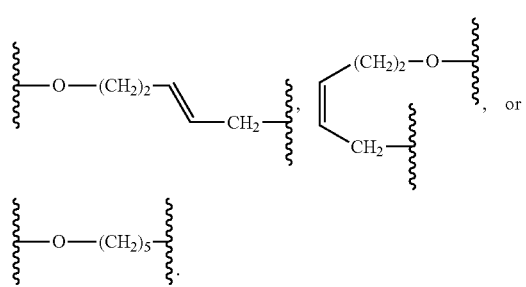

In formulae (I) and (II), preferably $R^2$—$R^1$—Y—Ar is

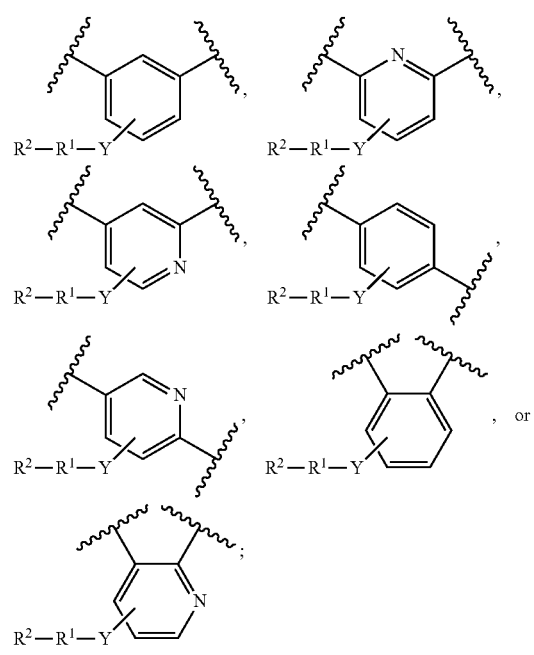

with the first being more preferred.

In formulae (I) and (II), Y preferably is O, NH, or a bond (more preferably O or a bond), especially when combined with n equals 1.

In one embodiment, $R^1$ is a 6-membered aromatic, a 5- to 6-membered heteroaromatic, a 4- to 7-membered cycloaliphatic, or a 4- to 7-membered heterocycloaliphatic moiety;

and $R^2$ is H, $C_1$-$C_3$ alkyl, halo, O($C_1$-$C_3$ alkyl), CN, $NO_2$, or $(CH_2)_{1-4}R^3$.

Where $R^1$ is a cycloaliphatic or heterocycloaliphatic moiety, preferably such moiety comprises a 5- or 6-membered ring.

Where $R^1$ is a 6-membered aromatic or a 5- to 6-membered heteroaromatic, it preferably is

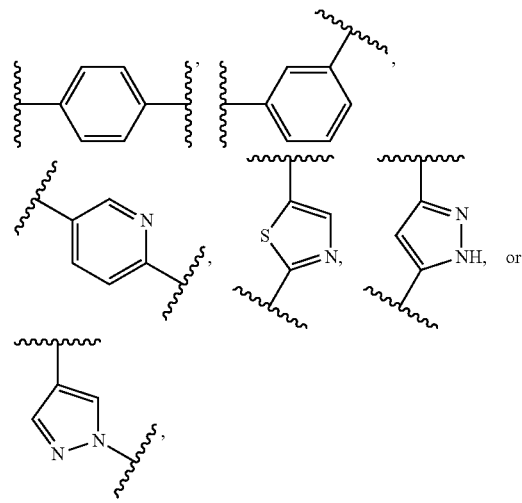

and more preferably is

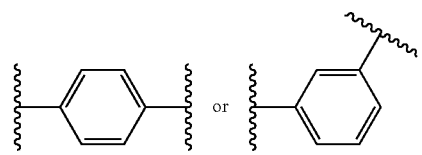

In formulae (I), (II), (IIa) (IIb) and (IId), preferably $R^1$ is not absent and $R^2$ is $(CH_2)_{1-2}NHR^3$, where $R^3$ is OH, Cl,

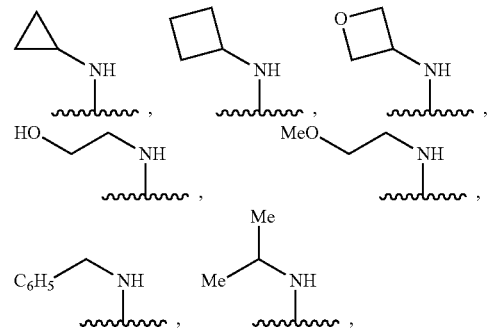

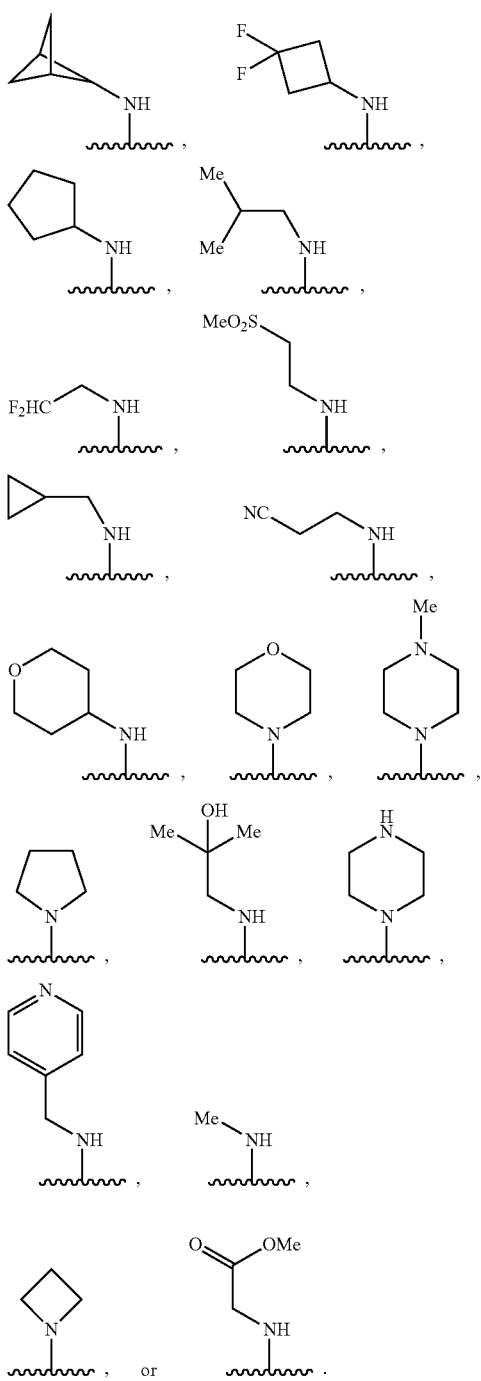

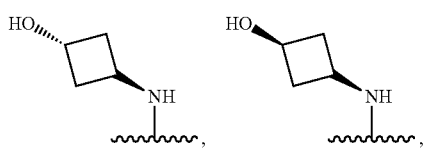

Further, R³ can be selected from the group consisting of the moieties listed in the preceding paragraph and the following moieties:

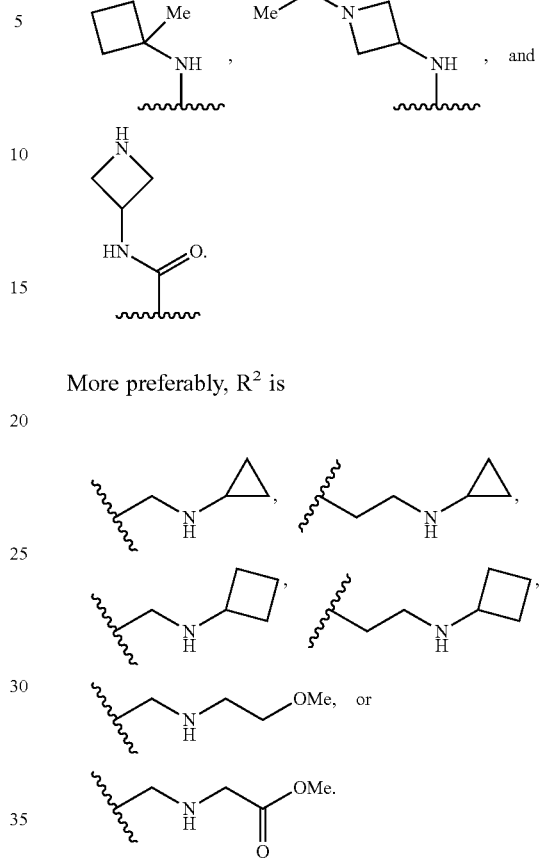

More preferably, R² is

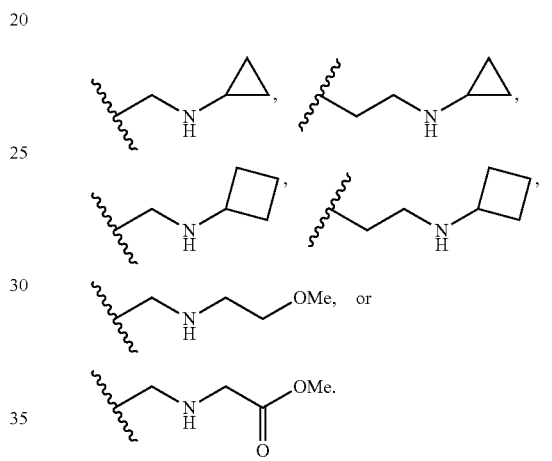

Figure 11:
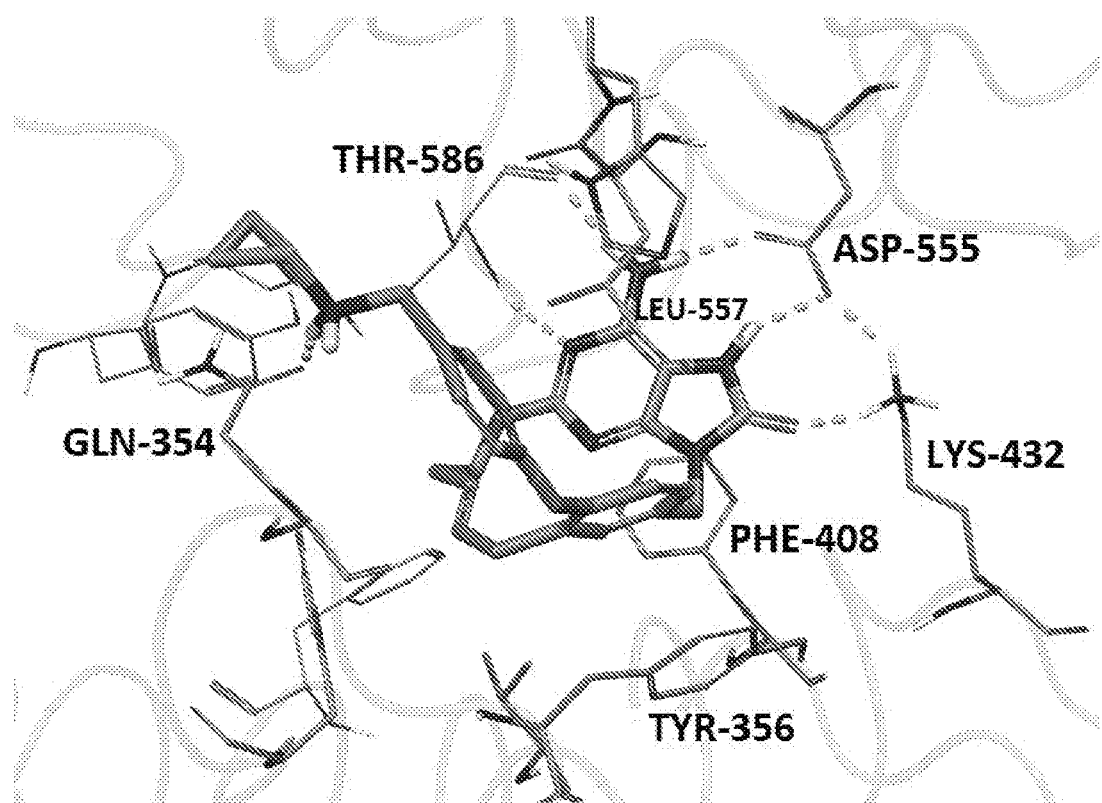
FIG. 11 is a computer model diagram showing the fit of a compound disclosed herein in its TLR7 binding site.

It is believed that the combination of a secondary amine and a small capping moiety attached to the amine nitrogen is advantageous for enhancing potency of the compounds disclosed herein. The secondary amine makes a hydrogen bond with a glutamine residue at the entrance of the TLR7 binding site. FIG. 11 is a computer model showing compound IIa-02, where the capping moiety is a cyclopropyl group, docked in the small molecule binding site of monkey TLR7 crystal structure (Zhang et al. 2016; Berman et al., *Nucleic Acids Res.* 2000, 28: 235). The aforementioned secondary amine interactions are visible in the upper left quadrant.

Table A presents biological activity data for compounds disclosed herein. One set of data relates TLR7 agonism activity using the HEK-Blue™ TLR7 reporter assay, as described in Example 11 hereinbelow. Another set of data relates to the induction of interleukin 6 (IL-6), a cytokine that plays an important role in the TLR7 pathway. As noted in Example 12 hereinbelow, the IL-6 data are normalized against a resiquimod reference at the highest test concentration of 10 μM. In some instances, more that one TLR7 agonism or IL-6 induction assay was made; if so, the reported value is an average.

For comparison, the activities of resiquimod, vesatolimod, gardiquimod, and Compounds B1-B5 (see Bonfanti et al. 2015b) are also presented.

(B1) 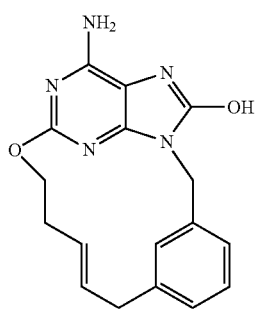

(B2) 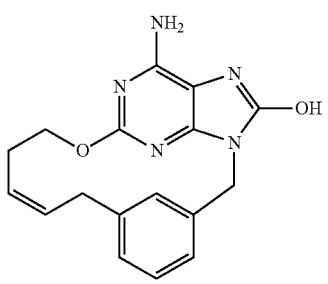

(B3) 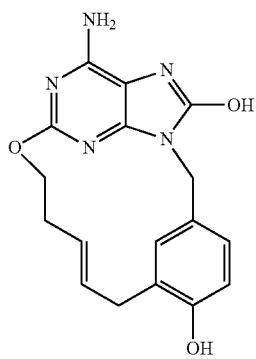

(B4) 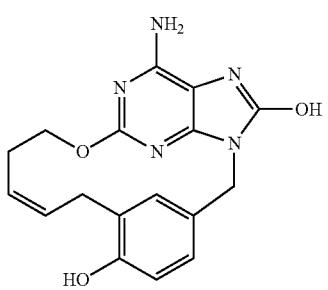

(B5) 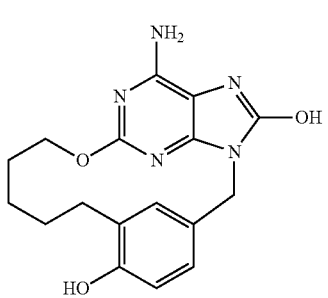

TABLE A

| Compound | TLR7 Agonism HEK Blue ™ Assay $EC_{50}$ (nM) | IL-6 Induction $EC_{50}$ (nM) (normalized 10 μM) |
|---|---|---|
| Resiquimod | 420 | 350 |
| Vesatolimod | 1,200 | — |
| Gardiquimod | 3,300 | — |
| B1 | 210 | — |
| B2 | 33 | — |
| B3 | 68 | 400 |
| B4 | 17 | 960 |
| B5 | 580 | — |
| IIa-01 | 51 | — |
| IIa-02 | 4.0 | 5.2 |
| IIa-03 | 5.3 | 47 |
| IIa-04 | 0.91 | 4.4 |
| IIa-05 | 7.2 | 18 |
| IIa-06 | 1.0 | 2.2 |
| IIa-07 | 4.2 | 2.9 |
| IIa-08 | 8.9 | 6.6 |
| IIa-09 | 2.2 | 1.9 |
| IIa-10 | 4.3 | 50 |
| IIa-11 | 6.6 | 5.5 |
| IIa-12 | 29 | 110 |
| IIa-13 | 0.94 | 13 |
| IIa-14 | 19 | 140 |
| IIa-15 | 9.2 | 57 |
| IIa-16 | 42 | 250 |
| IIa-17 | 8.5 | 44 |
| IIa-18 | 10 | 32 |
| IIa-19 | 25 | 95 |
| IIa-20 | 15 | 91 |
| IIb-01 | 0.67 | 42 |
| IIb-02 | 0.35 | 1.3 |
| IIb-03 | 2.9 | 65 |
| IIb-04 | 0.28 | 10 |
| IIb-05 | 0.22 | 0.62 |
| IIb-06 | 21 | 570 |
| IIb-07 | 0.22 | 1.6 |
| IIb-08 | 1.7 | 6.2 |
| IIb-09 | 0.35 | 2.1 |
| IIb-10 | 1.1 | 0.41 |
| IIb-11 | 0.33 | 0.68 |
| IIb-12 | 4.2 | 13 |
| IIb-13 | 0.24 | 4.3 |
| IIb-14 | 3.0 | 5.3 |
| IIb-15 | 0.65 | 4.7 |
| IIb-16 | 1.2 | 3.6 |
| IIb-17 | 0.91 | 0.99 |
| IIb-18 | 3.8 | 34 |
| IIb-19 | 1.0 | 1.4 |
| IIb-20 | 56 | 150 |
| IIb-21 | 0.32 | 1.5 |
| IIb-22 | 0.42 | 1.4 |
| IIb-23 | 0.81 | 2.0 |
| IIb-24 | 0.68 | 2.7 |
| IIb-25 | 1.5 | 0.81 |
| IIb-26 | 0.26 | 1.0 |
| IIb-27 | 0.62 | 4.0 |
| IIb-28 | 0.76 | 1.3 |
| IIb-29 | 3.2 | 24 |
| IIb-30 | 1.6 | 36 |
| IIb-31 | 6.8 | 28 |
| IIb-32 | 4.1 | 32 |
| IIb-33 | 0.42 | — |
| IIb-34 | 0.12 | 0.76 |
| IIb-35 | 1.5 | — |
| IIb-36 | 1.0 | — |
| IIb-37 | 3.8 | 180 |
| IIb-38 | 22 | 1,000 |
| IIb-39 | 1.6 | — |
| IIb-40 | 14 | 160 |
| IIc-01 | 3.7 | 5.0 |
| IIc-02 | 23 | 200 |
| IId-01 | 15 | 60 |
| IIe-01 | 5.3 | 40 |
| IIe-02 | 70 | 1,100 |

Preferably, compounds of this disclosure have an EC$_{50}$ of 50 nM or less in the HEK-Blue TLR7 Reporter Assay and an EC$_{50}$ of 50 nM or less in the IL-6 Induction assay.

Conjugation for Site-Specific Delivery

General

TLR7 agonists disclosed herein can be delivered to the site of intended action by localized administration or by targeted delivery in a conjugate with a targeting moiety. Preferably, the targeting moiety is an antibody or antigen binding portion thereof and its antigen is found at the locality of intended action, for example a tumor associated antigen if the intended site of action is at a tumor (cancer). Preferably, the tumor associated antigen is uniquely expressed or overexpressed by the cancer cell, compared to a normal cell. The tumor associated antigen can be located on the surface of the cancer cell or secreted by the cancer cell into its environs.

In one aspect, there is provided a conjugate comprising compound of this invention and a ligand, represented by formula (IV)

$$[D(X^D)_a(C)_c(X^Z)_b]_m Z \qquad (IV)$$

where Z is a targeting moiety, D is an agonist of this invention, and —$(X^D)_a C(X^Z)_b$— are collectively referred to as a "linker moiety" or "linker" because they link Z and D. Within the linker, C is a cleavable group designed to be cleaved at or near the site of intended biological action of D; $X^D$ and $X^Z$ are spacer moieties (or "spacers") that space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

By binding to a target tissue or cell where its antigen or receptor is located, Z directs the conjugate there. Cleavage of group C at the target tissue or cell releases D to exert its effect locally. In this manner, precise delivery of D is achieved at the site of intended action, reducing the dosage needed. Also, D is normally biologically inactive (or significantly less active) in its conjugated state, thereby reducing off-target effects.

As reflected by the subscript m, each Z can conjugate with more than one D, depending on the number of sites Z has available for conjugation and the experimental conditions employed. Those skilled in the art will appreciate that, while each individual Z is conjugated to an integer number of Ds, a preparation of the conjugate may analyze for a non-integer ratio of D to Z, reflecting a statistical average. This ratio is referred to as the substitution ratio ("SR") or the drug-antibody ratio ("DAR").

Targeting Moiety Z

Preferably, targeting moiety Z is an antibody. For convenience and brevity and not by way of limitation, the detailed discussion in this specification about Z and its conjugates is written in the context of its being an antibody, but those skilled in the art will understand that other types of Z can be conjugated, mutatis mutandis. For example, conjugates with folic acid as the targeting moiety can target cells having the folate receptor on their surfaces (Leamon et al., Cancer Res. 2008, 68 (23), 9839). For the same reasons, the detailed discussion in this specification is primarily written in terms of a 1:1 ratio of Z to D (m=1).

Antibodies that can be used in conjugates of this invention include those recognizing the following antigens: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Preferably, the antibody is an anti-mesothelin antibody.

In addition to being an antibody, Z can also be an antibody fragment (such as Fab, Fab', F(ab')$_2$, Fd, or Fv) or antibody mimetic, such as an affibody, a domain antibody (dAb), a nanobody, a unibody, a DARPin, an anticalin, a versabody, a duocalin, a lipocalin, or an avimer.

Any one of several different reactive groups on Z can be a conjugation site, including ε-amino groups in lysine residues, pendant carbohydrate moieties, carboxylic acid groups on aspartic or glutamic acid side chains, cysteine-cysteine disulfide groups, and cysteine thiol groups. For reviews on antibody reactive groups suitable for conjugation, see, e.g., Garnett, Adv. Drug Delivery Rev. 2001, 53, 171-216 and Dubowchik and Walker, Pharmacology & Therapeutics 1999, 83, 67-123, the disclosures of which are incorporated herein by reference.

Most antibodies have multiple lysine residues, which can be conjugated via their ε-amino groups via amide, urea, thiourea, or carbamate bonds.

A thiol (—SH) group in the side chain of a cysteine can be used to form a conjugate by several methods. It can be used to form a disulfide bond between it and a thiol group on the linker. Another method is via its Michael addition to a maleimide group on the linker.

Typically, although antibodies have cysteine residues, they lack free thiol groups because all their cysteines are engaged in intra- or inter-chain disulfide bonds. To generate a free thiol group, a native disulfide group can be reduced. See, e.g., Packard et al., *Biochemistry* 1986, 25, 3548; King et al., *Cancer Res.* 1994, 54, 6176; and Doronina et al., *Nature Biotechnol.* 2003, 21, 778. Alternatively, a cysteine having a free —SH group can be introduced by mutating the antibody, substituting a cysteine for another amino acid or inserting one into the polypeptide chain. See, for example, Eigenbrot et al., U.S. Pat. No. 7,521,541B2 (2009); Chilkoti et al., *Bioconjugate Chem.* 1994, 5, 504; Urnovitz et al., U.S. Pat. No. 4,698,420 (1987); Stimmel et al., *J. Biol. Chem.* 2000, 275, 30445; Bam et al., U.S. Pat. No. 7,311,902 B2 (2007); Kuan et al., *J. Biol. Chem.* 1994, 269, 7610; Poon et al., *J. Biol. Chem.* 1995, 270, 8571; Junutula et al., *Nature Biotechnology* 2008, 26, 925 and Rajpal et al., US 2018/0362619 (2018). In yet another approach, a cysteine is added to the C-terminus of the heavy of light chain. See, e.g., Liu et al., U.S. Pat. No. 8,865,875 B2 (2014); Cumber et al., *J. Immunol.* 1992, 149, 120; King et al, *Cancer Res.* 1994, 54, 6176; Li et al., *Bioconjugate Chem.* 2002, 13, 985; Yang et al., *Protein Engineering* 2003, 16, 761; and Olafson et al., *Protein Engineering Design & Selection* 2004, 17, 21. The disclosures of the documents cited in this paragraph are incorporated herein by reference.

Linkers and their Components

As noted above, the linker comprises up to three elements: a cleavable group C and optional spacers $X^Z$ and $X^D$.

Group C is cleavable under physiological conditions. Preferably it is relatively stable while the conjugate is in circulation in the blood, but is readily cleaved once the conjugate reaches its site of intended action.

A preferred group C is a peptide that is cleaved selectively by a protease inside the target cell, as opposed to by a protease in the serum. Typically, the peptide comprises from 1 to amino acids, preferably from 1 to 6 amino acids, more preferably from 2 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this specification, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

A group C can be chosen such that it is cleaved by a protease present in the extracellular matrix in the vicinity of a cancer, e.g., a protease released by nearby dying cancer cells or a tumor-associated protease secreted by cancer cells. Exemplary extracellular tumor-associated proteases are plasmin, matrix metalloproteases (MMP), thimet oligopeptidase (TOP) and CD10. See, e.g., Trouet et al., U.S. Pat. No. 7,402,556 B2 (2008); Dubois et al., U.S. Pat. No. 7,425,541 B2 (2008); and Bebbington et al., U.S. Pat. No. 6,897,034 B2 (2005). Cathepsin D, normally lysosomal enzyme found inside cells, is sometimes found in the environs of a tumor, possibly released by dying cancer cells.

For conjugates designed to be by an enzyme, C preferably comprises an amino acid sequence selected for cleavage by proteases such cathepsins B, C, D, H, L and S, especially cathepsin B. Exemplary cathepsin B cleavable peptides include Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit. (Herein, amino acid sequences are written in the N-to-C direction, as in $H_2N$-$AA^2$-$AA^1$-$CO_2H$, unless the context clearly indicates otherwise.) See Dubowchik et al., *Biorg. Med. Chem. Lett.* 1998, 8, 3341; Dubowchik et al., *Bioorg. Med. Chem. Lett.* 1998, 8, 3347; and Dubowchik et al., *Bioconjugate Chem.* 2002, 13, 855; the disclosures of which are incorporated by reference.

Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu. More preferably, it is a two to three amino acid peptide from the foregoing group.

The preparation and design of cleavable groups C consisting of a single amino acid is disclosed in Chen et al., U.S. Pat. No. 8,664,407 B2 (2014), the disclosure of which is incorporated herein by reference.

Group C can be bonded directly to Z or D; i.e. spacers $X^Z$ or $X^D$, as the case may be, can be absent.

When present, spacer $X^Z$ provides spatial separation between C and Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

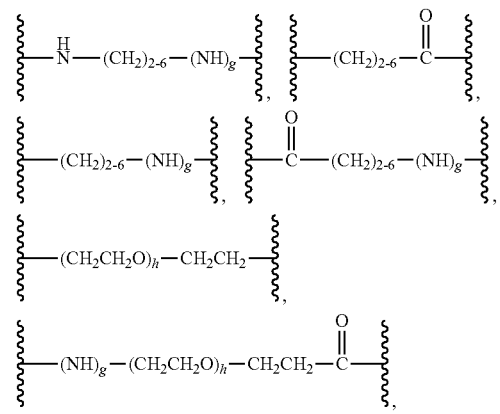

and combinations thereof, where the subscript g is 0 or 1 and the subscript h is 1 to 24, preferably 2 to 4. These segments can be combined, such as illustrated below:

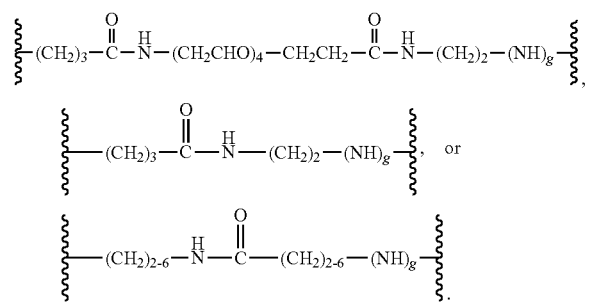

Spacer $X^D$, if present, provides spatial separation between C and D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, analogously to the description above for spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain a poly(ethylene glycol) ("PEG") group. Since the conjugation step typically involves coupling a drug-linker to an antibody in an aqueous medium, a PEG group many enhance the aqueous solubility of the drug-linker. Also, a PEG group may enhance the solubility or reduce aggregation in the resulting ADC. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to C and either Z or D and (2) has a structure such that cleavage from group C initiates a reaction sequence resulting in the self-immolating moiety disbonding itself from Z or D, as the case may be. In other words, reaction at a site distal from Z or D (cleavage from group C) causes the $X^Z$-Z or the $X^D$-D bond to rupture as well. The presence of a self-immolating moiety is desirable in the case of spacer $X^D$ because, if, after cleavage of the conjugate, spacer $X^D$ or a portion thereof were to remain attached to D, the biological activity of D may be impaired. The use of a self-immolating moiety is especially desirable where cleavable group C is a polypeptide, in which instance the self-immolating moiety typically is located adjacent thereto, in order to prevent D from sterically or electronically interfering with peptide cleavage.

Exemplary self-immolating moieties (i)-(v) bonded to a hydroxyl or amino group of D are shown below:

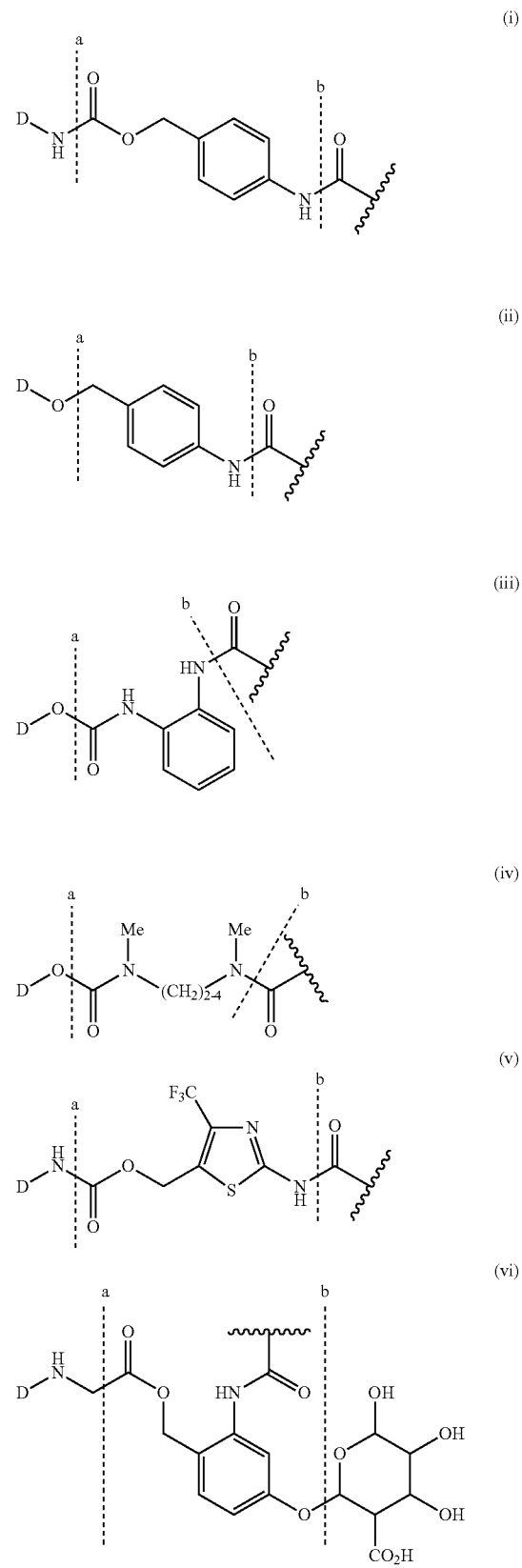

(vii)

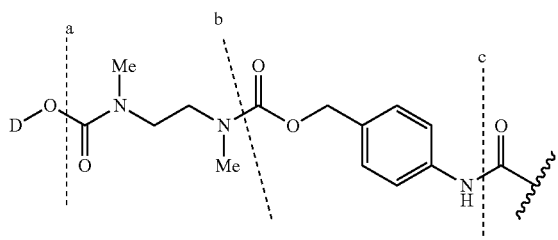

The self-immolating moiety is the structure between dotted lines a and b (or dotted lines b and c), with adjacent structural features shown to provide context. Self-immolating moieties (i) and (v) are bonded to a D-NH$_2$ (i.e., conjugation is via an amino group), while self-immolating moieties (ii), (iii), and (iv) are bonded to a D-OH (i.e., conjugation is via a hydroxyl or carboxyl group). Cleavage of the bond at dotted line b by an enzyme—a peptidase in the instance of structures (i)-(v) and a β-glucuronidase in the instance of structure (vi)—initiates a self-immolating reaction sequence that results in the cleavage of the bond at dotted line a and the consequent release of D-OH or D-NH$_2$, as the case may be. By way of illustration, self-immolating mechanisms for structures (i) and (iv) are shown below:

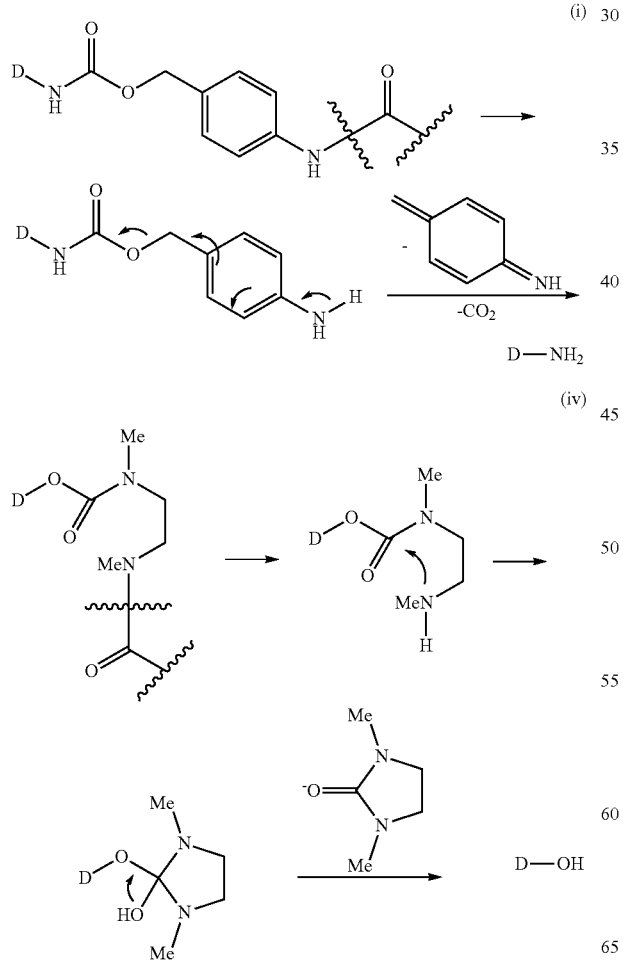

In other words, cleavage of a first chemical bond at one part of a self-immolating group initiates a sequence of steps that results in the cleavage of a second chemical bond—the one connecting the self-immolating group to the drug—at a different part of the self-immolating group, thereby releasing the drug.

In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.* 1981, 24, 479; Carl et al., WO 81/01145 (1981); Dubowchik et al., *Pharmacology & Therapeutics* 1999, 83, 67; Firestone et al., U.S. Pat. No. 6,214,345 B1 (2001); Toki et al., *J. Org. Chem.* 2002, 67, 1866; Doronina et al., *Nature Biotechnology* 2003, 21, 778 (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference.

In another embodiment, Z and D are linked by a non-cleavable linker, i.e., C is absent. Metabolism of D eventually reduces the linker to a small appended moiety that does not interfere with the biological activity of D.

Conjugation Techniques

Conjugates of TLR7 agonists disclosed herein preferably are made by first preparing a compound comprising D and linker $(X^D)_a(C)_c(X^Z)_b$ (where $X^D$, C, $X^Z$, a, b, and c are as defined for formula (II)) to form drug-linker compound represented by formula (V):

$$D\text{-}(X^D)_a(C)_c(X^Z)_b\text{—}R^{31} \qquad (V)$$

where $R^{31}$ is a functional group suitable for reacting with a complementary functional group on Z to form the conjugate. Examples of suitable groups $R^{31}$ include amino, azide, thiol, cyclooctyne,

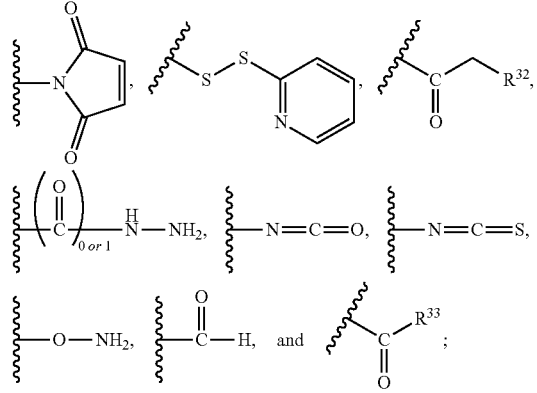

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties D-$(X^D)_a$C$(X^Z)_b$—$R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2

(2011); Sufi et al., U.S. Pat. No. 8,461,117 B2 (2013); and Chen et al., U.S. Pat. No. 8,664,407 B2 (2014); the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are:

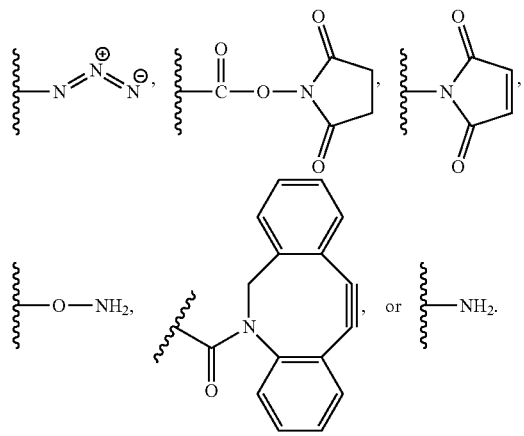

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Where an antibody does not have a cysteine —SH available for conjugation, an ε-amino group in the side chain of a lysine residue can be reacted with 2-iminothiolane or N-succinimidyl-3-(2-pyridyldithio)propionate ("SPDP") to introduce a free thiol (—SH) group—creating a cysteine surrogate, as it were. The thiol group can react with a maleimide or other nucleophile acceptor group to effect conjugation. The mechanism if illustrated below with 2-iminothiolane.

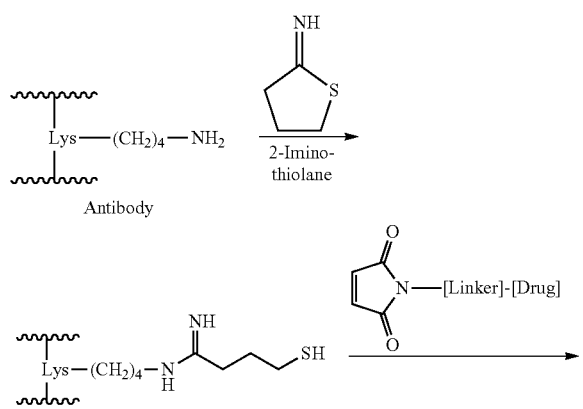

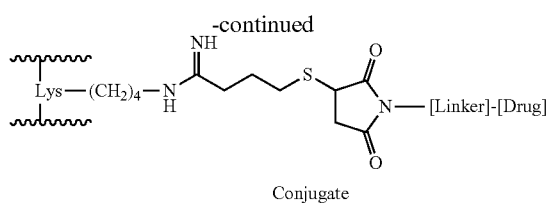

Conjugate

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody Z can be modified with N-succinimidyl 4-(maleimidomethyl)-cyclohexanecarboxylate ("SMCC") or its sulfonated variant sulfo-SMCC, both of which are available from Sigma-Aldrich, to introduce a maleimide group thereto. Then, conjugation can be effected with a drug-linker compound having an —SH group on the linker.

An alternative conjugation method employs copper-free "click chemistry," in which an azide group adds across a strained cyclooctyne to form an 1,2,3-triazole ring. See, e.g., Agard et al., J. Amer. Chem. Soc. 2004, 126, 15046; Best, Biochemistry 2009, 48, 6571, the disclosures of which are incorporated herein by reference. The azide can be located on the antibody and the cyclooctyne on the drug-linker moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

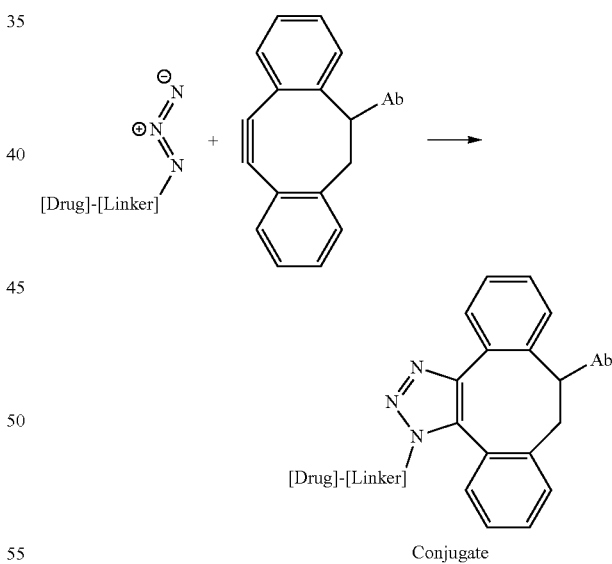

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase from *Streptomyces mobaraensis* or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

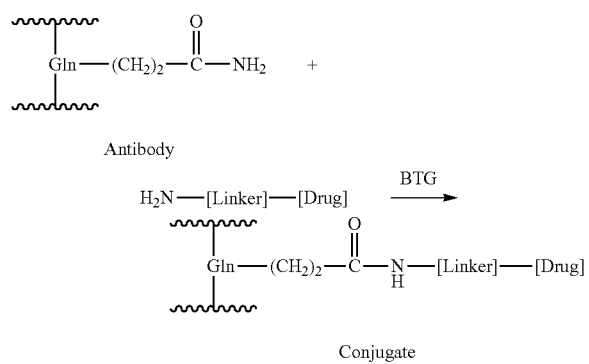

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an unmodified antibody, as taught in Rao-Naik et al., WO 2017/059158 A1 (2017).

While the most commonly available bacterial transglutaminase is that from *S. mobaraensis*, transglutaminase from other bacteria, having somewhat different substrate specificities, can be considered, such as transglutaminase from *Streptoverticillium ladakanum* (Hu et al., US 2009/0318349 A1 (2009), US 2010/0099610 A1 (2010), and US 2010/0087371 A1 (2010)).

Figure 12:
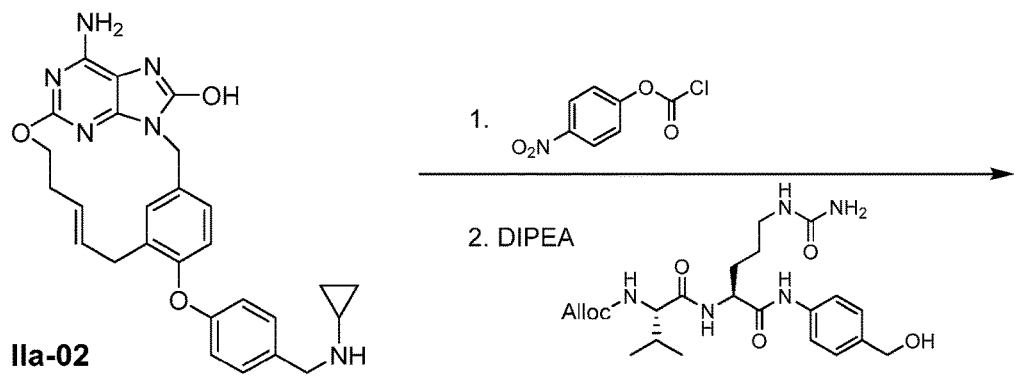
FIGS. 12 and 13 show exemplary schemes for the attachment of linkers to compounds disclosed herein, rendering them suitable for conjugation.
Figure 12:
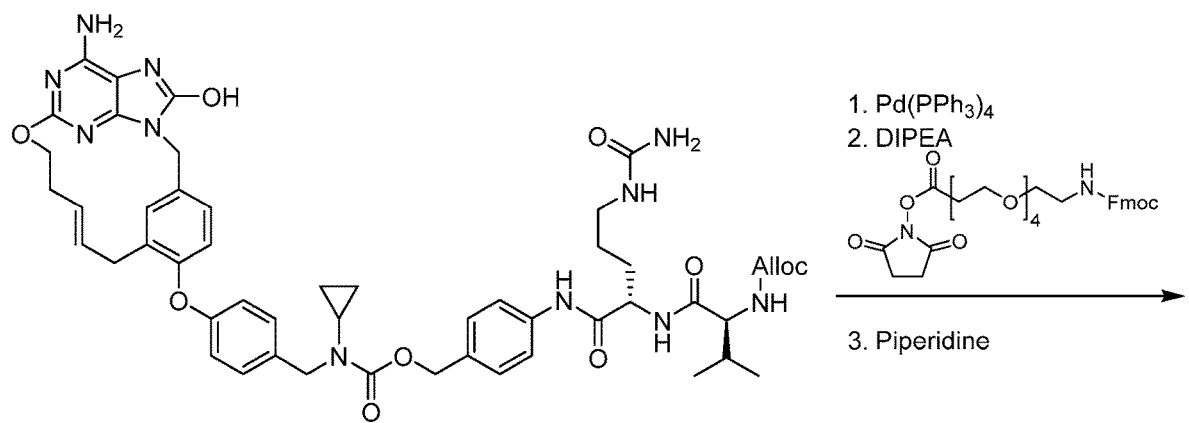
Figure 12:
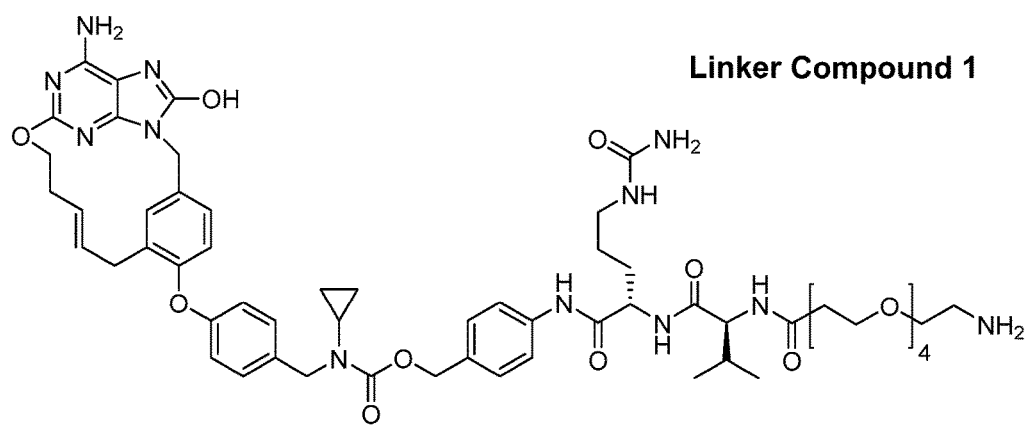

TLR7 agonists of this disclosure having a primary or secondary alkyl amine are particularly suitable for use in conjugates, as the secondary amine provides a functional group for attachment of the linker. An example of such a TLR7 agonist-linker compound is Linker Compound 1, which contains an enzymatically cleavable linker. FIG. 12 shows a scheme according to which it can be prepared.

Linker Compound 1

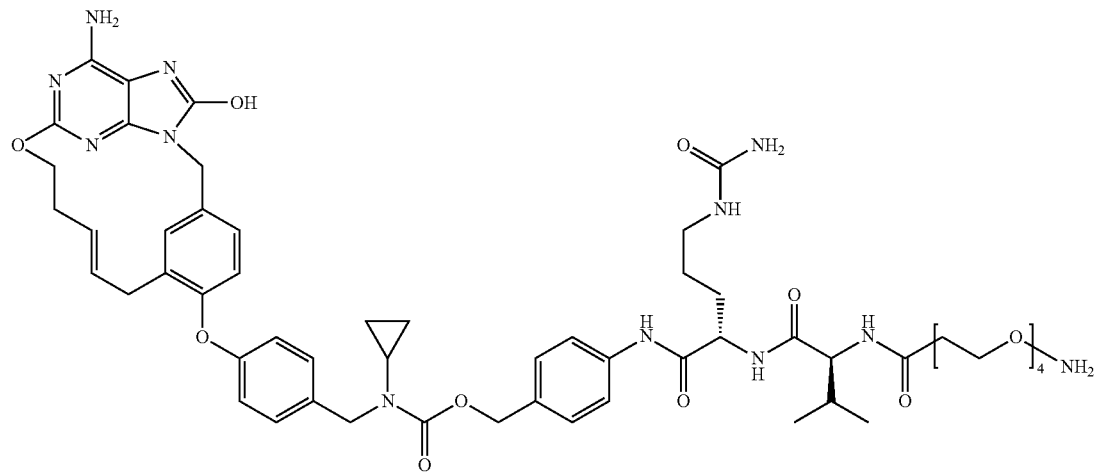

Figure 13:
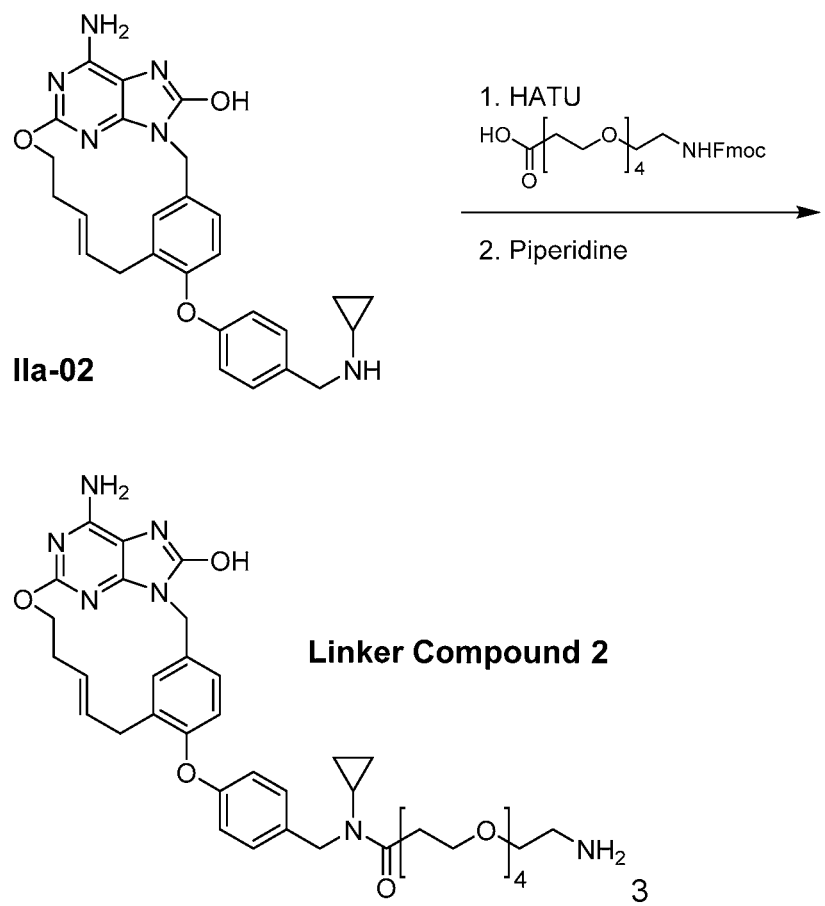

An example of a TLR7 agonist-linker compound that contains a non-enzymatically cleavable linker is Linker Compound 2. FIG. 13 shows a scheme for synthesizing it.

Both (AL-1) and (AL-2) contain a primary alkylamino group, rendering them amenable to conjugation with transglutaminase. A suitable conjugation procedure is described in the Examples hereinbelow.

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

TLR7 Agonist Conjugates

Applying the fore-described techniques, TLR7 agonist conjugates such as the ones shown below can be prepared:

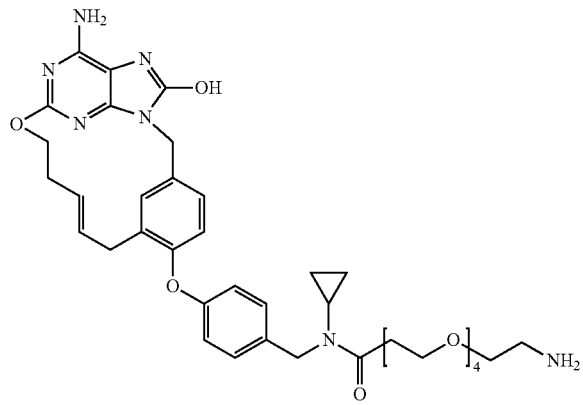

Linker Compound 2

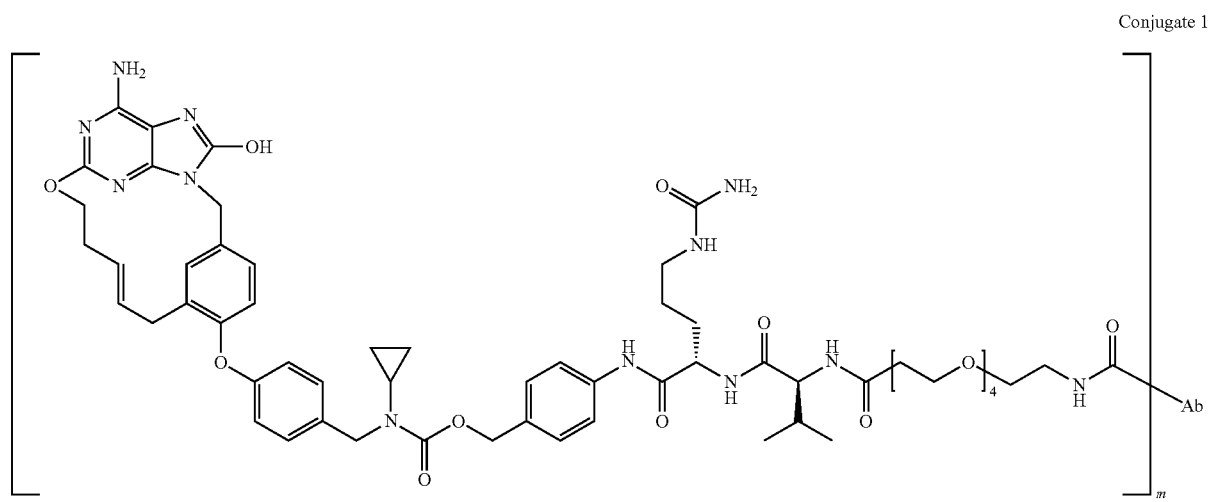

Conjugate 1

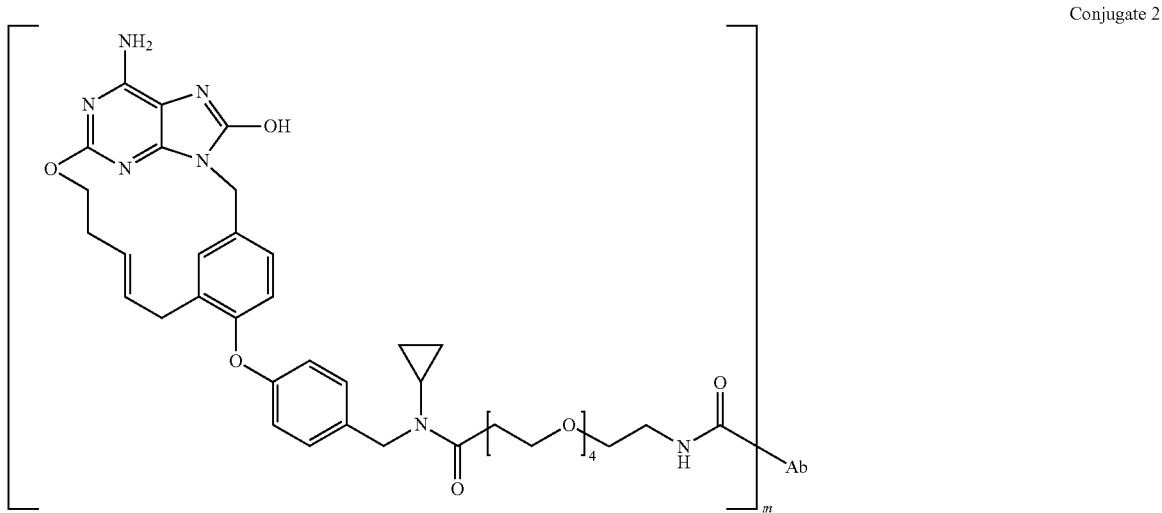

Conjugate 2 where m is 1, 2, 3, or 4 and Ab is an antibody.

Conjugation for Property Modulation

Attachment of a poly(ethylene glycol) (PEG) chain to a drug ("PEGylation") can improve the latter's pharmacokinetic properties. The circulation half-life of the drug is increased, sometimes by over an order of magnitude, concomitantly reducing the dosage needed to achieve a desired therapeutic effect. PEGylation can also decrease metabolic degradation of a drug and reduce its immunogenicity. For a review, see Kolate et al., *J. Controlled Release* 2014, 192, 167.

Initially, PEGylation was applied to biologic drugs. As of 2016, over ten PEGylated biologics had been approved. Turecek et al., *J. Pharmaceutical Sci.* 2016, 105, 460; Alconcel et al., *Polymer Chem.* 2011, 2, 1442. More recently, stimulated by the successful application of the concept to biologics, attention has turned towards its application to small molecule drugs. In addition to the aforementioned benefits, PEGylated small molecule drugs may have increased solubility and cause fewer toxic effects. Li et al. *Prog. Polymer Sci.* 2013, 38, 421. Small molecule drugs that have been PEGylated include the auristatins (Lyon et al., US 2016/0310612 A1 (2016)) and resiquimod (Zarraga, US 2007/0166384 A1 (2007)).

The TLR7 agonists disclosed herein can be PEGylated. Two illustrative structures, using compound (IIa-02) as an exemplar, are shown below. They can be prepared by methods analogous to those shown in FIGS. 12 and 13.

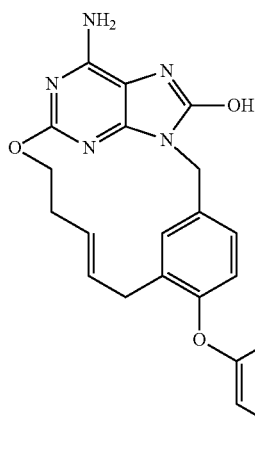
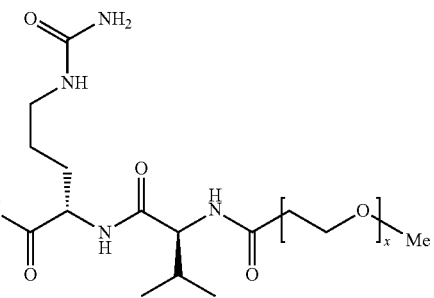

(1)

PEGylated IIa-02

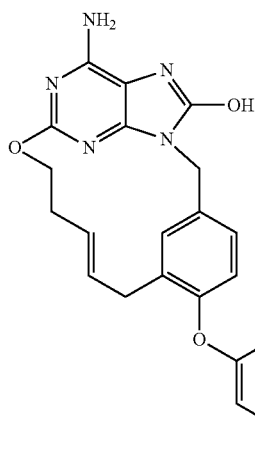

(2)

PEGylated IIa-02

Generally it is preferred that the PEG moiety have a formula weight of between about 2 kDa (corresponding to about 45 —(CH$_2$CH$_2$O)— repeating units) and between about 40 kDa (corresponding to about 910 —(CH$_2$CH$_2$O)— repeating units), more preferably between about 5 kDa and about 20 kDa. That is, the range of the subscript x in the above formulae is from about 45 to about 910. It is to be understood that PEG compositions are not 100% homogeneous but, rather, exhibit a distribution of molecular weights. Thus, a reference to, for example, "20 kDa PEG" means PEG having an average molecular weight of 20 kDa.

Those skilled in the art will appreciate that, addition to the chemistry shown in FIGS. 12 and 13, other synthetic methodologies can be employed, for instance as shown below:

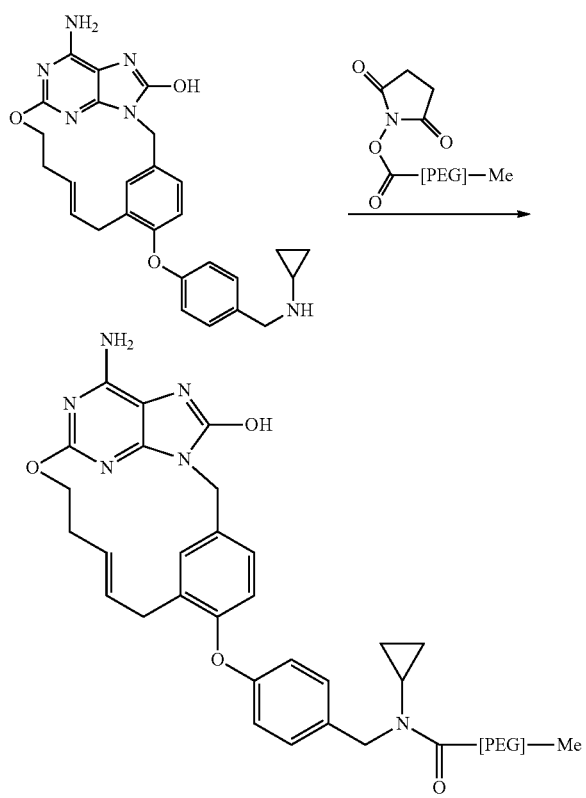

EXAMPLES

The practice of this invention can be further understood by reference to the following examples, which are provided by way of illustration and not of limitation.

A table after the Examples lists acronyms and abbreviations used herein and their meanings.

Figure 1B:
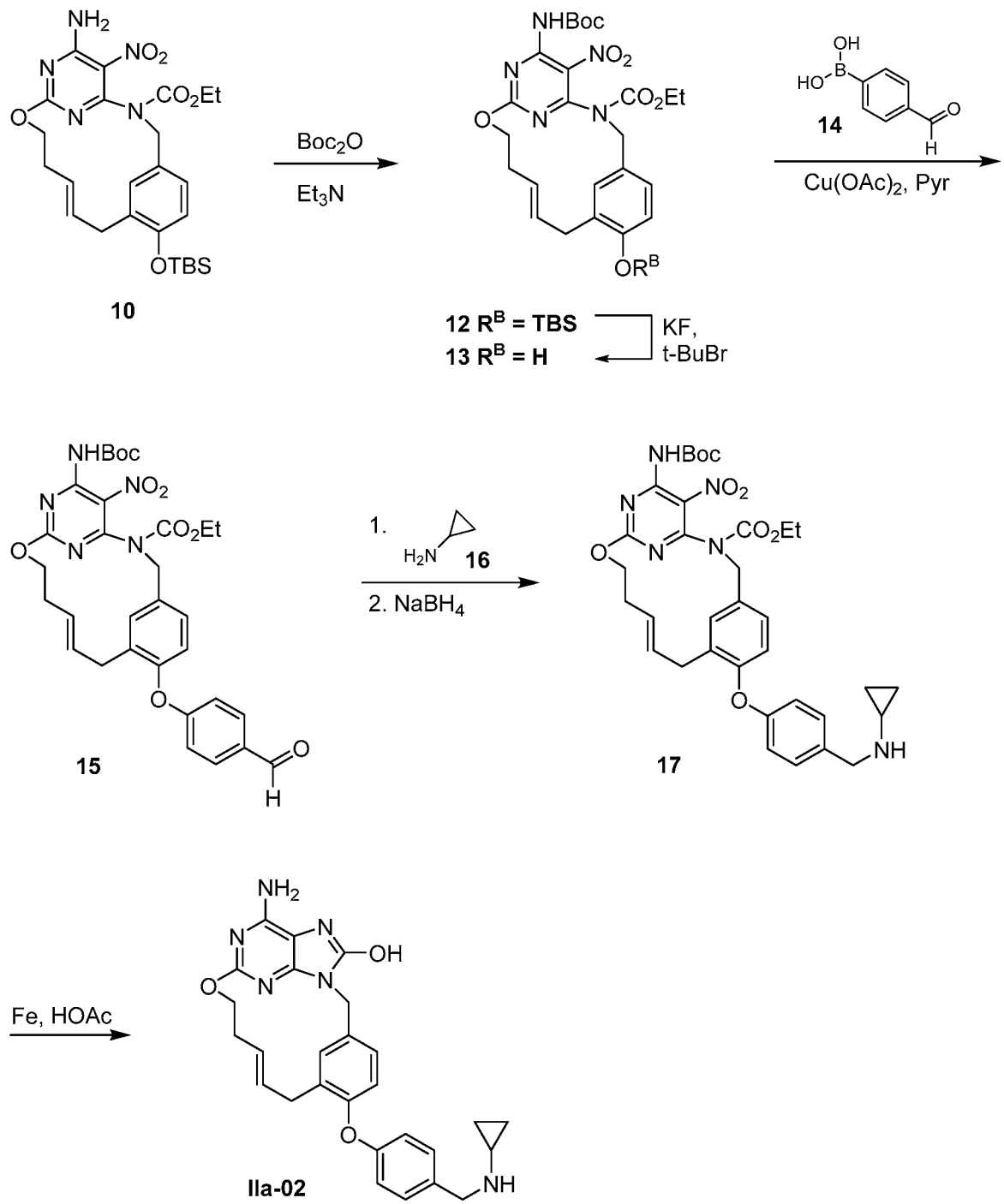

Example 1—Synthesis of Compounds According to FIGS. 1A and 1B

This example relates to the synthesis of compounds according to the scheme of FIGS. 1A-1B, with compound (IIa-02) being used as an exemplar.

ALDEHYDE 2. TBS-Cl (3.96 g, 26.3 mmol) was added to a solution of 3-allyl-4-hydroxybenzaldehyde 1 (Gu and Silverman, *Org. Lett.* 2003, 5(4), 415; 3.55 g, 21.89 mmol) and imidazole (2.235 g, 32.8 mmol) in DMF (44 mL) at RT. The reaction mixture was stirred at RT for 3 h, diluted with EtOAc, and washed with water and brine. The crude product was purified by flash chromatography on silica gel using an automated ISCO system (220 g column, eluting with 0-20% EtOAc/hexanes). Aldehyde 2 (4.67 g, 16.89 mmol, 77% yield) was obtained as a colorless oil. MS (ESI) m/z 277.1 (M+H); $^1$H NMR (400 MHz, chloroform-d) δ 9.89 (s, 1H), 7.72 (d, J=2.1 Hz, 1H), 7.67 (dd, J=8.3, 2.1 Hz, 1H), 6.92 (d, J=8.3 Hz, 1H), 6.00 (ddt, J=16.9, 10.2, 6.5 Hz, 1H), 5.16-5.04 (m, 2H), 3.43 (d, J=6.4 Hz, 2H), 1.05 (s, 9H), 0.31 (s, 6H).

ALCOHOL 3. Sodium borohydride (0.868 g, 22.93 mmol) was added to a solution of aldehyde 2 (3.17 g, 11.47 mmol) in MeOH (38 mL) at 0° C. The reaction mixture was stirred at 0° C. for 2 h, quenched with water, and partitioned between EtOAc and water. The layers were separated and the aqueous layer was extracted with EtOAc two more times. The combined organic layers were dried over MgSO$_4$ and concentrated in vacuo to give alcohol 3 (2.9 g, 10.41 mmol, 91% yield) as a colorless oil. $^1$H NMR (400 MHz, chloroform-d) δ 7.15 (d, J=2.0 Hz, 1H), 7.10 (dd, J=8.2, 2.3 Hz, 1H), 6.79 (d, J=8.1 Hz, 1H), 6.05-5.90 (m, 1H), 5.11-5.00 (m, 2H), 4.60 (s, 2H), 3.38 (d, J=6.5 Hz, 2H), 1.02 (s, 9H), 0.24 (s, 6H).

COMPOUND 5. DIAD (2.62 mL, 12.81 mmol) was added dropwise to a solution of ester 4 (Kettle et al., *J. Med. Chem.* 2016, 59(6), 2346; 2.5 g, 8.54 mmol), alcohol 3 (2.85 g, 10.25 mmol) and triphenylphosphine (3.36 g, 12.81 mmol) in THF (42 mL) at RT with a water cooling bath. The reaction mixture was stirred at RT for 2 h. The solvent was evaporated in vacuo and the crude product was purified by flash chromatography on silica gel using an automated ISCO system (80 g gold column, eluting with 0-25% EtOAc/hexanes). Compound 5 (3.0 g, 5.42 mmol, 63.5% yield) was obtained as a light yellow oil. MS (ESI) m/z 553.2 (M+H).

COMPOUND 6. 30% Aqueous ammonia (19.56 mL, 271 mmol) was added to a solution of compound 5 (3 g, 5.42 mmol) in THF (14 mL) at RT. The reaction mixture was stirred for 2 h. The reaction mixture was concentrated in vacuo to give crude compound 6 (2.9 g, 5.42 mmol, 100% yield) as a yellow solid. MS (ESI) m/z 534.2 (M+H).

COMPOUND 7. mCPBA (1.295 g, 5.71 mmol) was added to a solution of compound 6 (2.9 g, 5.42 mmol) in DCM (54 mL) at 0° C. The reaction mixture was stirred at RT for 3 h. Sodium thiosulfate (1.72 g, 10.87 mmol) in water (20 mL) was added. The layers were separated and the aqueous layer was extracted with DCM (2×20 mL). The organic layer was dried over MgSO$_4$ and concentrated in vacuo to give 2.98 g of crude compound 7, which was used without purification. MS (ESI) m/z 534.2 (M+H).

COMPOUND 9. A mixture of compound 7 (2.98 g, 5.43 mmol), but-3-en-1-ol 8 (11.75 g, 163 mmol) and TEA (1.1 mL, 8.15 mmol) was heated at 85° C. for 1 h. Excess but-3-en-1-ol 8 was removed in vacuo and the crude product was purified by flash chromatography on silica gel using an automated ISCO system (120 g gold column, eluting with 5-35% EtOAc/hexanes). Compound 9 (1.417 g, 2.54 mmol, 46.8% yield) was obtained as a colorless oil. MS (ESI) m/z 558.2 (M+H).

COMPOUNDS 10 AND 11. Grubbs II catalyst (0.216 g, 0.254 mmol) was added to a solution of compound 9 (1.417 g, 2.54 mmol) in DCM (730 mL), degassed by bubbling nitrogen gas for 30 min. The reaction mixture was evacuated and back filled with nitrogen three times, followed by stirring at 40° C. for 24 h. More Grubbs II catalyst (0.216 g, 0.254 mmol) was added and stirring was continued for another 24 h. SiliaMetS® Dimercaptotriazine (DMT) (0.886 g, 3.81 mmol) was added to the reaction mixture, which was then stirred at RT overnight. The reaction mixture was filtered through CELITE™ and the filtrate was concentrated in vacuo. The crude product was purified by flash chromatography on silica gel using an automated ISCO system (120 g gold column, eluting with 5-35% EtOAc/hexanes) to give 900 mg of a mixture of compounds 10 (E-isomer) and 11 (Z-isomer).

The mixture of compounds 10 and 11 was separated by chiral SFC (Berger SFC MGII, Column: Whelkol KMS 30×250 mm ID, 5 µm; Flow rate: 85.0 mL/min; Mobile Phase: 60/40 CO$_2$/MeOH; Detector Wavelength: 220 nm) to give compound 10 (0.505 g, 37.5% yield) as a white solid and compound 11 (309 mg, 23% yield) also as a white solid. The structures were confirmed by $^1$H, $^{13}$C, HH-decoupling NMR, COSY, HSQC and HMBC NMRs.

COMPOUND 10. MS (ESI) m/z 530.2 (M+H); $^1$H NMR (400 MHz, chloroform-d) δ 7.31-7.29 (m, 1H), 7.21 (dd, J=8.2, 2.2 Hz, 1H), 6.68 (d, J=8.2 Hz, 1H), 5.53 (dt, J=15.0, 7.4 Hz, 1H), 5.46-5.34 (m, 1H), 5.12 (br s, 1H), 4.62 (br s, 2H), 4.20 (q, J=7.1 Hz, 2H), 3.21 (br d, J=6.8 Hz, 2H), 2.56 (q, J=6.0 Hz, 2H), 1.24 (t, J=7.1 Hz, 3H), 0.99 (s, 9H), 0.19 (s, 6H); HH-decoupling NMR showed vinyl proton at 5.53 ppm with a coupling constant J=15.12 Hz which is consistent with trans double bond configuration.

COMPOUND 11. MS (ESI) m/z 530.2 (M+H); $^1$H NMR (400 MHz, chloroform-d) δ 7.72 (br s, 1H), 7.57 (br s, 1H), 7.13 (dd, J=8.2, 2.0 Hz, 1H), 6.70 (d, J=8.2 Hz, 1H), 5.97-5.67 (m, 2H), 5.42 (dt, J=10.7, 7.8 Hz, 1H), 4.99 (s, 2H), 4.56-4.44 (m, 2H), 4.18 (q, J=7.1 Hz, 2H), 3.33 (d, J=7.9 Hz, 2H), 2.56 (br s, 2H), 1.22 (t, J=7.1 Hz, 3H), 1.02 (s, 9H), 0.23 (s, 6H); HH-decoupling NMR showed vinyl proton at 5.88 ppm with a coupling constant J=10.85 Hz which is consistent with cis double bond configuration.

COMPOUND 12. A solution of compound 10 (0.5 g, 0.944 mmol), Boc-anhydride (0.24 mL, 1.038 mmol), DIEA (0.33 mL, 1.888 mmol) and DMAP (0.012 g, 0.094 mmol) in DCM (20 mL) was stirred at RT for 2 h. Solvent was evaporated in vacuo and the crude product was purified by flash chromatography on silica gel using an automated ISCO system (80 g gold column, eluting with 5-30% EtOAc/hexanes) to give compound 12 (408 mg, 0.648 mmol, 68.6% yield) as a foaming solid. MS (ESI) m/z 630.3 (M+H).

COMPOUND 13. A mixture compound 12 (0.408 g, 0.648 mmol), potassium fluoride (0.075 g, 1.296 mmol) and 2-bromo-2-methylpropane (0.087 mL, 0.777 mmol) in DMF (13 mL) was stirred at RT for 2 hours. The reaction mixture was diluted with EtOAc and washed with water and brine. The organic layer was dried over MgSO$_4$ and concentrated in vacuo. The crude product was purified by flash chromatography on silica gel using an automated ISCO system (40 g column, eluting with 5-60% EtOAc/hexanes). Compound 13 (331 mg, 0.642 mmol, 99% yield) was obtained as a foaming solid. MS (ESI) m/z 516.1 (M+H); $^1$H NMR (400 MHz, chloroform-d) δ 9.21 (s, 1H), 7.25 (br s, 1H), 7.21 (dd, J=8.1, 2.0 Hz, 1H), 6.65 (d, J=8.1 Hz, 1H), 5.67-5.55 (m, 1H), 5.40 (dt, J=15.0, 7.3 Hz, 1H), 5.16 (s, 2H), 4.77 (br s, 3H), 4.24-4.15 (m, 2H), 3.19 (d, J=7.4 Hz, 2H), 2.63 (q, J=6.0 Hz, 2H), 1.52 (s, 9H), 1.29-1.25 (m, 3H).

COMPOUND 15. A mixture of compound 13 (331 mg, 0.642 mmol), (4-formylphenyl)boronic acid 14 (289 mg, 1.926 mmol), copper (II) acetate (175 mg, 0.963 mmol), pyridine (260 μL, 3.21 mmol) and molecular sieves (4 Å, 150 mg) in DCM (6 mL) was stirred at 35° C. overnight. LCMS showed about 50% conversion. More (4-formylphenyl)boronic acid 14 (96 mg, 0.64 mmol), copper (II) acetate (58 mg, 0.32 mmol), pyridine (87 μl, 1.07 mmol) and molecular sieves (4 Å, 100 mg) were added and heating continued over the weekend. CELITE™ was added and the reaction mixture was filtered through a plug of silica gel and rinsed with EtOAc. The filtrate was concentrated and the crude product was purified by flash chromatography on silica gel using an automated ISCO system (120 g gold column, eluting with 0-45% EtOAc/hexanes). Partial separation was achieved; the impure fractions were purified three more time (80 g gold column, eluting with 10-30% EtOAc/hexanes). Pure fractions were combined and concentrated to give compound 15 (270 mg, 0.436 mmol, 67.9% yield) as a yellow solid. MS (ESI) m/z 620.2 (M+H); $^1$H NMR (400 MHz, chloroform-d) δ 9.89 (s, 1H), 9.20 (s, 1H), 7.84-7.77 (m, 2H), 7.46 (br s, 1H), 7.37 (dd, J=8.2, 2.1 Hz, 1H), 6.94-6.86 (m, 3H), 5.54-5.44 (m, 1H), 5.44-5.35 (m, 1H), 5.22 (s, 2H), 4.74 (br s, 2H), 4.20 (q, J=6.7 Hz, 2H), 3.12 (br d, J=7.0 Hz, 2H), 2.61 (q, J=5.9 Hz, 2H), 1.53 (s, 9H).

COMPOUND 17. A mixture of compound 15 (165 mg, 0.266 mmol) and cyclopropanamine 16 (37 μL, 0.533 mmol) in MeOH (3 mL)/DCM (3 mL) was stirred at RT overnight. NaBH$_4$ (20.2 mg, 0.533 mmol) was added to the reaction mixture and the reaction mixture was stirred at RT for 0.5 h. The reaction mixture was diluted with EtOAc and washed with water and brine. The organic layer was dried over MgSO$_4$ and concentrated in vacuo. The crude product was purified by flash chromatography on silica gel using an automated ISCO system (80 g gold column, eluting with 1-6% 2 N ammonia in MeOH/DCM). Compound 17 (99 mg, 0.150 mmol, 56.3% yield) was obtained as a yellow foaming solid. MS (ESI) m/z 661.2 (M+H); $^1$H NMR (400 MHz, chloroform-d) δ 7.41 (br s, 1H), 7.32-7.19 (m, 3H), 6.85-6.80 (m, 2H), 6.78 (d, J=8.2 Hz, 1H), 5.62-5.51 (m, 1H), 5.48-5.37 (m, 1H), 5.32 (s, 1H), 5.21 (s, 2H), 4.77 (br s, 2H), 4.21 (q, J=6.8 Hz, 2H), 3.80 (s, 2H), 3.23 (br d, J=7.2 Hz, 2H), 2.64 (q, J=5.9 Hz, 2H), 2.21-2.10 (m, 1H), 1.55 (s, 9H), 1.30-1.22 (m, 3H), 0.49-0.43 (m, 2H), 0.42-0.37 (m, 2H).

COMPOUND IIa-02. A mixture of compound 17 (99 mg, 0.150 mmol) and iron (50.2 mg, 0.899 mmol) in acetic acid (2.5 mL)/water (0.5 mL) was heated at 85° C. for 45 min. LCMS showed completion of the reaction. Solvent was evaporated in vacuo. The residue was suspended in 25% MeOH/DCM (5 mL) and the contents were filtered. The filtrate was concentrated and the crude product was re-dissolved in 25% MeOH/DCM (3 mL) and loaded onto a 12 g dry column, then purified by flash chromatography on silica gel using an automated ISCO system (80 g gold column, eluting with 1-16% 2 N ammonia in MeOH/DCM). Fractions containing pure product were concentrated to give compound IIa-02 (45 mg, 0.091 mmol, 60.7% yield) as a white solid. The structure was confirmed by $^1$H, $^{13}$C, COSY, ROESY, dept-H-$^{13}$C HSQC and $^1$H-$^{13}$C HMBC NMRs. MS (ESI) m/z 485.1 (M+H); $^1$H NMR (500 MHz, DMSO-d$_6$) δ 9.90 (br s, 1H), 8.25 (d, J=2.1 Hz, 1H), 7.26 (d, J=8.7 Hz, 2H), 7.14 (dd, J=8.1, 2.2 Hz, 1H), 6.82 (d, J=8.5 Hz, 2H), 6.72 (d, J=8.1 Hz, 1H), 6.43 (br s, 2H), 5.70-5.62 (m, 1H), 5.52-5.44 (m, 1H), 4.82 (s, 2H), 4.74-4.68 (m, 2H), 3.66 (s, 2H), 3.13 (br d, J=7.1 Hz, 2H), 2.45-2.38 (m, 2H), 2.01 (tt, J=6.7, 3.5 Hz, 1H), 0.36-0.29 (m, 2H), 0.26-0.17 (m, 2H).

Additional compounds were prepared by methods analogous to those described above, mutatis mutandis.

COMPOUND IIa-01. Prepared by sodium borohydride in MeOH reduction of compound 15, followed by the same sequence as used for converting compound 17 to compound IIa-02. MS (ESI) m/z 446.2 (M+H).

COMPOUND IIa-03. MS (ESI) m/z 485.3 (M+H); $^1$H NMR (500 MHz, DMSO-d$_6$) δ 8.23 (s, 1H), 7.25 (t, J=7.8 Hz, 1H), 7.15 (dd, J=8.1, 1.8 Hz, 1H), 7.03 (br d, J=7.5 Hz, 1H), 6.88 (br s, 1H), 6.77-6.69 (m, 2H), 6.31 (s, 2H), 5.71-5.59 (m, 1H), 5.52-5.42 (m, 1H), 4.83 (s, 2H), 4.73-4.66 (m, 2H), 3.71 (s, 2H), 3.43-3.29 (m, 3H), 3.13 (br d, J=6.7 Hz, 2H), 2.45-2.37 (m, 2H), 0.33 (br d, J=4.6 Hz, 2H), 0.25 (br d, J=2.9 Hz, 2H).

COMPOUND IIa-04. MS (ESI) m/z 485.2 (M+H); $^1$H NMR (500 MHz, DMSO-d$_6$) δ 8.04 (s, 1H), 7.30 (br d, J=7.9 Hz, 2H), 7.15 (br d, J=7.9 Hz, 1H), 6.85 (br d, J=8.2 Hz, 2H), 6.76 (br d, J=7.9 Hz, 1H), 6.45 (br s, 2H), 5.70-5.61 (m, 1H), 5.60-5.52 (m, 1H), 4.82 (s, 2H), 4.53-4.41 (m, 2H), 3.74 (br s, 1H), 3.26 (br d, J=7.3 Hz, 1H), 2.42-2.32 (m, 2H), 2.12 (br s, 1H), 0.39 (br d, J=5.5 Hz, 2H), 0.31 (br s, 2H).

COMPOUND IIa-05. MS (ESI) m/z 485.1 (M+H); $^1$H NMR (500 MHz, DMSO-d$_6$) δ 8.04 (s, 1H), 7.32-7.25 (m, 1H), 7.16 (br d, J=7.9 Hz, 1H), 7.07 (br d, J=7.6 Hz, 1H), 6.93 (br s, 1H), 6.79 (br d, J=7.9 Hz, 2H), 6.44 (br s, 2H), 5.69-5.61 (m, 1H), 5.60-5.51 (m, 1H), 4.83 (s, 2H), 4.52-4.43 (m, 2H), 3.78 (br s, 1H), 3.25 (br d, J=7.6 Hz, 2H), 2.36 (br s, 2H), 2.14 (br s, 1H), 0.38 (br s, 2H), 0.35-0.27 (m, 2H).

COMPOUND IIa-06. MS (ESI) m/z 499.1 (M+H); $^1$H NMR (500 MHz, DMSO-$d_6$) δ 8.04 (s, 1H), 7.27 (br d, J=8.2 Hz, 2H), 7.15 (br d, J=7.6 Hz, 1H), 6.82 (br d, J=8.2 Hz, 2H), 6.75 (br d, J=7.9 Hz, 1H), 6.45 (br s, 2H), 5.70-5.61 (m, 1H), 5.60-5.53 (m, 1H), 4.82 (s, 2H), 4.52-4.43 (m, 2H), 3.90 (s, 3H), 3.55 (s, 1H), 3.26 (br d, J=7.3 Hz, 2H), 2.37 (br d, J=7.0 Hz, 2H), 2.10-2.00 (m, 3H), 1.72-1.46 (m, 4H).

COMPOUND IIa-07. MS (ESI) m/z 499.2 (M+H); $^1$H NMR (500 MHz, DMSO-$d_6$) δ 8.05 (s, 1H), 7.29-7.22 (m, 1H), 7.16 (br d, J=8.2 Hz, 1H), 7.03 (br d, J=7.3 Hz, 1H), 6.89 (br s, 1H), 6.76 (br dd, J=17.5, 8.1 Hz, 2H), 6.44 (br s, 2H), 5.71-5.61 (m, 1H), 5.60-5.52 (m, 1H), 4.82 (s, 2H), 4.52-4.43 (m, 2H), 3.59 (s, 1H), 3.25 (br d, J=7.3 Hz, 2H), 3.17-3.08 (m, 1H), 2.38 (br d, J=7.6 Hz, 2H), 2.00 (br d, J=7.6 Hz, 2H), 1.91 (s, 1H), 1.73-1.44 (m, 4H).

COMPOUND IIa-08. MS (ESI) m/z 499.1 (M+H); $^1$H NMR (500 MHz, DMSO-$d_6$) δ 8.24 (s, 1H), 7.26 (br d, J=8.2 Hz, 2H), 7.14 (br d, J=7.9 Hz, 1H), 6.81 (br d, J=8.2 Hz, 2H), 6.71 (d, J=7.9 Hz, 1H), 6.43 (br s, 2H), 5.71-5.57 (m, 1H), 5.53-5.39 (m, 1H), 4.81 (s, 2H), 4.70 (br s, 2H), 3.57 (s, 1H), 3.11 (br d, J=7.0 Hz, 2H), 2.40 (br s, 2H), 2.04 (br d, J=7.6 Hz, 2H), 1.78-1.46 (m, 4H).

COMPOUND IIa-09. MS (ESI) m/z 503.4 (M+H); $^1$H NMR (500 MHz, DMSO-$d_6$) δ 9.99 (s, 1H), 8.93-8.71 (m, 2H), 8.28 (d, J=1.4 Hz, 1H), 7.44 (br d, J=8.3 Hz, 2H), 7.20 (br d, J=8.0 Hz, 1H), 6.92 (br d, J=8.5 Hz, 2H), 6.81 (d, J=8.3 Hz, 1H), 6.46 (br s, 2H), 5.70-5.57 (m, 1H), 5.54-5.41 (m, 1H), 4.84 (s, 2H), 4.71 (br s, 2H), 4.09 (s, 2H), 3.89 (s, 1H), 3.60-3.53 (m, 2H), 3.29 (s, 3H), 3.12-3.03 (m, 4H), 2.43-2.37 (m, 2H).

COMPOUND IIa-10. MS (ESI) m/z 517.3 (M+H); $^1$H NMR (500 MHz, DMSO-$d_6$) δ 9.94 (br s, 1H), 8.25 (s, 1H), 7.28 (br d, J=8.3 Hz, 2H), 7.15 (br d, J=7.7 Hz, 1H), 6.83 (br d, J=8.3 Hz, 2H), 6.74 (d, J=8.0 Hz, 1H), 6.43 (br s, 2H), 5.71-5.60 (m, 1H), 5.47 (dt, J=15.1, 7.6 Hz, 1H), 4.82 (s, 2H), 4.71 (br s, 2H), 3.70 (s, 2H), 3.62 (s, 3H), 3.12 (br d, J=6.9 Hz, 2H), 2.40 (br s, 2H).

COMPOUND IIa-11. A mixture of compounds 10 and 11 (118 mg, 0.223 mmol) and platinum (IV) oxide (7.6 mg, 0.033 mmol) in THF (5 mL)/MeOH (5 mL) was hydrogenated with a balloon of hydrogen for 7 h. The reaction mixture was filtered through CELITE™ and the filtrate was concentrated in vacuo. The crude product was purified by flash chromatography on silica gel using an automated ISCO system (40 g gold column, eluting with 5-50% EtOAc/hexanes). Intermediate A (77 mg, 0.145 mmol, 65.0% yield) was obtained as a white solid. MS (ESI) m/z 532.2 (M+H).

Intermediate A was converted to compound IIa-11 using procedures analogous to those described above. MS (ESI) m/z 487.2 (M+H); $^1$H NMR (500 MHz, DMSO-$d_6$) δ 7.49 (br s, 1H), 7.03 (br d, J=8.2 Hz, 2H), 6.75 (br d, J=7.0 Hz, 1H), 6.60-6.48 (m, 3H), 6.24 (br s, 2H), 4.63 (br s, 2H), 3.98 (br s, 2H), 3.43 (s, 2H), 2.42 (br s, 2H), 1.79 (br d, J=3.1 Hz, 1H), 1.61 (br s, 1H), 1.43 (br s, 2H), 1.22-1.03 (m, 4H), 0.11 (br d, J=4.0 Hz, 2H), 0.00 (br s, 2H).

COMPOUND IIa-12. MS (ESI) m/z 487.2 (M+H); $^1$H NMR (500 MHz, DMSO-$d_6$) δ 10.07 (s, 1H), 7.74 (br s, 1H), 7.42-7.34 (m, 1H), 7.19 (br d, J=7.6 Hz, 1H), 7.08 (br s, 1H), 7.01 (br d, J=8.2 Hz, 1H), 6.85 (br d, J=8.2 Hz, 1H), 6.78 (br d, J=8.2 Hz, 1H), 6.43 (br s, 1H), 4.86 (s, 2H), 4.24-4.13 (m, 4H), 2.63 (br s, 3H), 1.66 (br s, 2H), 1.44-1.27 (m, 4H), 0.78 (br s, 2H), 0.71 (br d, J=6.4 Hz, 2H).

COMPOUND IIa-13. MS (ESI) m/z 499.2 (M+H).

COMPOUND IIa-14. MS (ESI) m/z 499.2 (M+H).

COMPOUND IIa-15. MS (ESI) m/z 485.2 (M+H).

COMPOUND IIa-16. MS (ESI) m/z 501.2 (M+H).

COMPOUND IIa-17. MS (ESI) m/z 499.3 (M+H); $^1$H NMR (500 MHz, DMSO-$d_6$) δ 7.84 (s, 1H), 7.33 (d, J=8.3 Hz, 2H), 6.93 (d, J=8.5 Hz, 2H), 6.75 (s, 1H), 6.70 (s, 1H), 6.47 (br s, 2H), 5.65 (dt, J=15.0, 7.4 Hz, 1H), 5.43 (dt, J=15.3, 7.6 Hz, 1H), 4.79 (s, 2H), 4.67 (br s, 2H), 3.61 (s, 2H), 3.21-3.14 (m, 3H), 2.43-2.36 (m, 2H), 2.12-2.03 (m, 2H), 1.91 (s, 2H), 1.76-1.51 (m, 4H).

COMPOUND IIa-18. MS (ESI) m/z 485.2 (M+H); $^1$H NMR (500 MHz, DMSO-$d_6$) δ 9.98 (br s, 1H), 7.83 (s, 1H), 7.33 (d, J=8.3 Hz, 2H), 6.93 (d, J=8.5 Hz, 2H), 6.74 (s, 1H), 6.69 (s, 1H), 6.45 (br s, 2H), 5.70-5.60 (m, 1H), 5.47-5.37 (m, 1H), 4.79 (s, 2H), 4.67 (br s, 2H), 3.72 (s, 2H), 3.21-3.11 (m, 3H), 2.39 (br d, J=4.1 Hz, 1H), 2.11-2.04 (m, 1H), 0.42-0.34 (m, 2H), 0.31-0.24 (m, 2H).

COMPOUND IIc-01. This compound was prepared using a slightly modified reaction sequence, wherein the Chan-Lamb coupling between compounds 13 and 14 (FIG. 1B) was replaced by a Mitsunobu reaction of tert-butyl 4-hydroxypiperidine-1-carboxylate with compound 13.

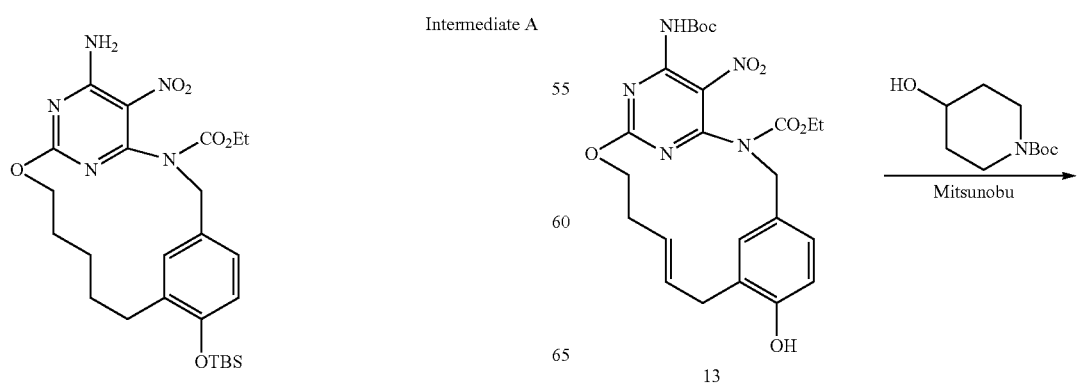

13

63

-continued

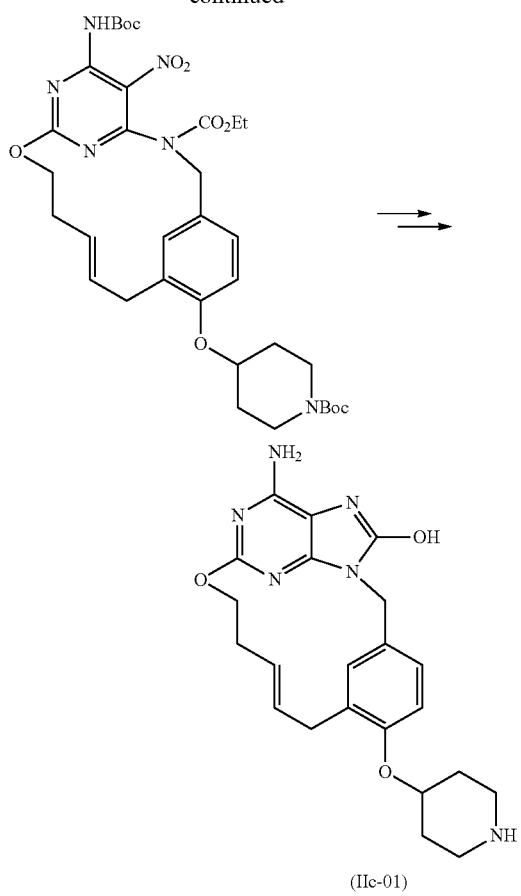

(IIc-01)

MS (ESI) m/z 423.2 (M+H); $^1$H NMR (400 MHz, DMSO-$d_6$) δ 10.22 (br s, 1H), 8.13 (s, 1H), 7.11 (dd, J=8.1, 1.7 Hz, 1H), 6.90 (d, J=8.3 Hz, 1H), 6.58 (s, 2H), 5.78-5.63 (m, 1H), 5.45 (dt, J=15.3, 7.5 Hz, 1H), 4.81-4.68 (m, 4H), 4.68-4.56 (m, 1H), 3.40 (br s, 1H), 3.21-3.11 (m, 4H), 3.11-3.01 (m, 2H), 2.43 (br d, J=4.2 Hz, 2H), 2.12-1.96 (m, 2H), 1.83 (td, J=6.8, 3.5 Hz, 2H).

COMPOUND IIc-02. This compound was prepared in analogous manner as compound IIc-01. MS (ESI) m/z 423.2 (M+H); $^1$H NMR (500 MHz, DMSO-$d_6$) δ 7.62 (s, 1H), 6.70 (br d, J=13.0 Hz, 2H), 6.48 (br s, 2H), 5.67-5.58 (m, 1H), 5.44-5.34 (m, 1H), 4.78 (s, 2H), 4.65 (br s, 2H), 4.47-4.40 (m, 1H), 3.15 (br d, J=6.8 Hz, 2H), 3.06-2.98 (m, 2H), 2.77-2.68 (m, 2H), 2.38-2.38 (m, 1H), 2.38 (br d, J=2.6 Hz, 1H), 1.98-1.90 (m, 2H), 1.87 (br s, 2H), 1.62-1.48 (m, 2H).

COMPOUND B3. MS (ESI) m/z 340.1 (M+H); $^1$H NMR (500 MHz, DMSO-$d_6$) δ 7.97 (s, 1H), 6.94 (br d, J=7.9 Hz, 1H), 6.61 (d, J=7.9 Hz, 1H), 6.34 (br s, 1H), 5.65 (dt, J=15.3, 7.3 Hz, 1H), 5.37 (dt, J=15.2, 7.5 Hz, 1H), 4.70 (s, 4H), 3.83 (br s, 2H), 3.02 (br d, J=6.7 Hz, 2H), 2.39 (br d, J=4.0 Hz, 2H).

COMPOUND B4. MS (ESI) m/z 340.1 (M+H); $^1$H NMR (500 MHz, DMSO-$d_6$) δ 9.85 (s, 1H), 9.44 (s, 1H), 7.74 (s, 1H), 6.94 (br d, J=7.9 Hz, 1H), 6.69 (d, J=7.9 Hz, 1H), 6.37 (br s, 2H), 5.71-5.63 (m, 1H), 5.59-5.51 (m, 1H), 4.70 (s, 2H), 4.51-4.41 (m, 2H), 3.18 (br d, J=7.6 Hz, 2H), 2.38-2.27 (m, 2H).

COMPOUND B5. MS (ESI) m/z 342.1 (M+H).

64

Figure 2A:
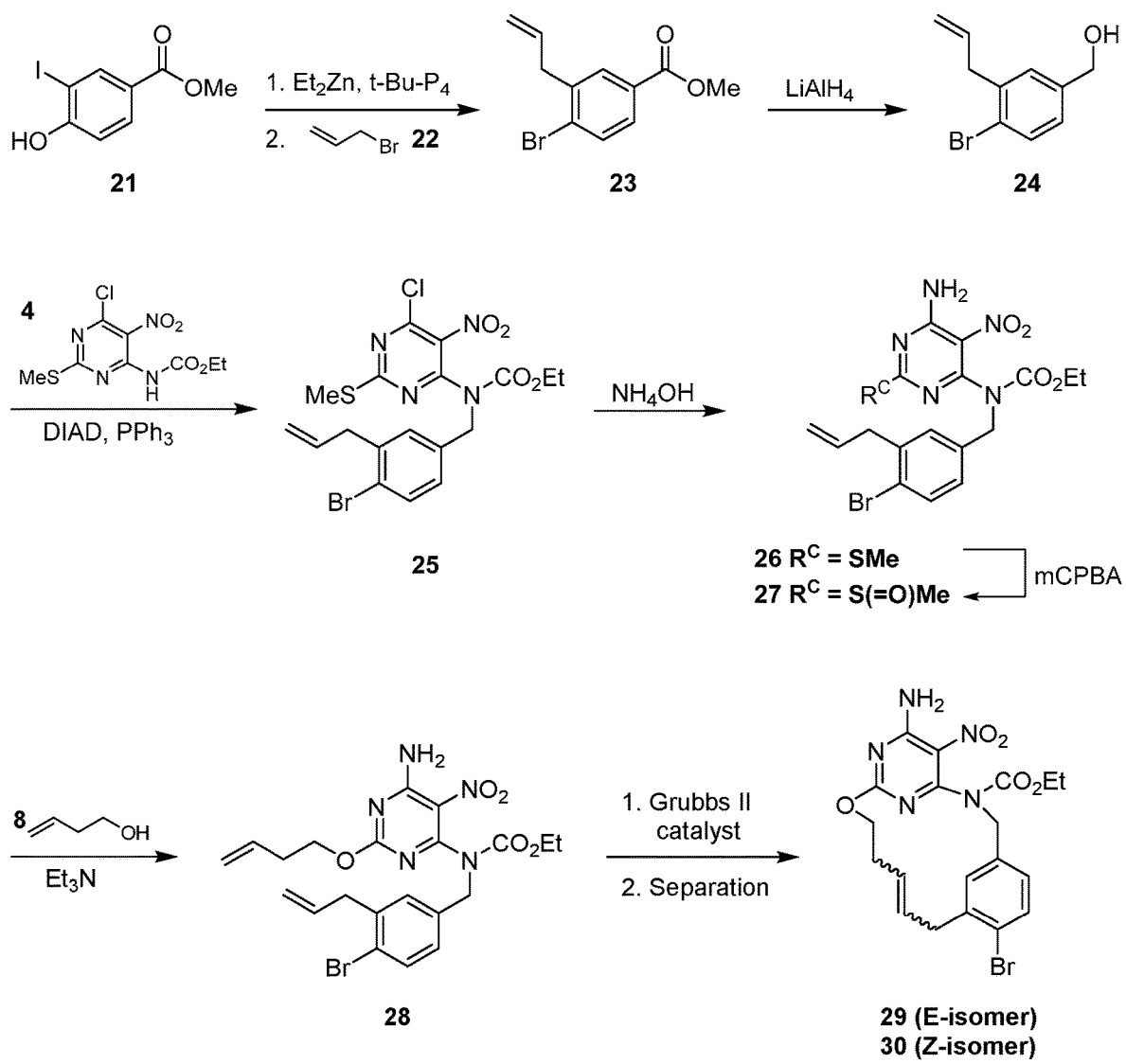
Figure 2B:
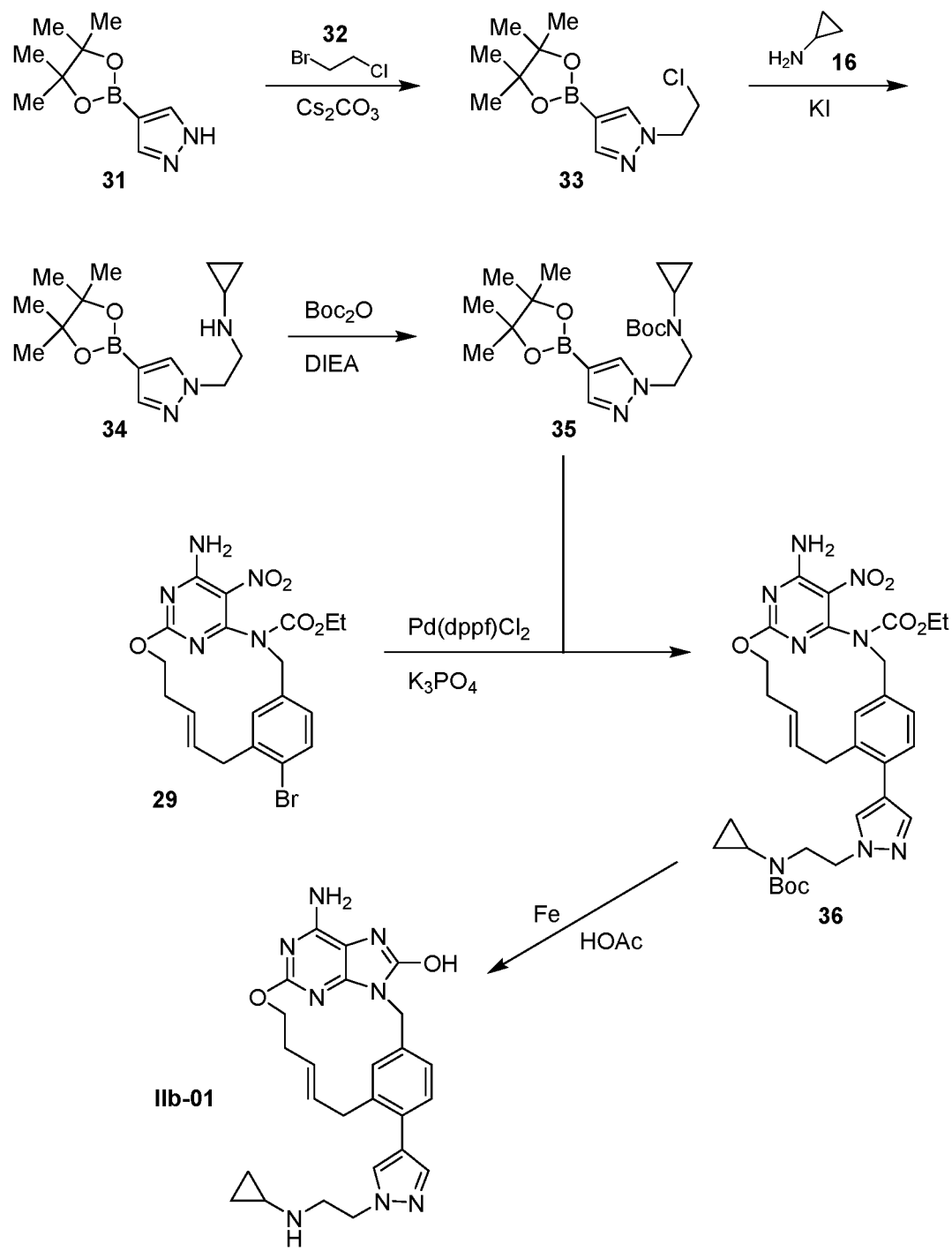

Example 2—Synthesis of Compounds According to FIGS. 2A and 2B

This example relates to the synthesis of compounds according to the scheme of FIGS. 2A-2B, with compound (IIb-01) being used as an exemplar.

COMPOUND 23. 1M Phosphazene base P4-T-BU in hexane (0.500 mL, 0.500 mmol) was added to a solution of methyl 4-bromo-3-iodobenzoate 21 (3.41 g, 10 mmol) and 1M diethylzinc in hexane (12.00 mL, 12.00 mmol) in dry DMA (10 mL) at RT. The reaction mixture was stirred at RT for 24 h. 3-Bromoprop-1-ene 22 (1.0 mL, 12.00 mmol) was added and stirring was continued over the weekend. The reaction was quenched by the careful addition of saturated NH$_4$Cl and extracted with EtOAc. The organic layer was washed with brine, dried over MgSO$_4$, and concentrated in vacuo. The crude product was purified by flash chromatography on silica gel using an automated ISCO system (80 g column, eluting with 10-70% CHCl$_3$/hexanes). Compound 23 (2.258 g, 8.85 mmol, 89% yield) was obtained as a colorless oil. $^1$H NMR (400 MHz, chloroform-d) δ 7.92 (d, J=2.1 Hz, 1H), 7.76 (dd, J=8.3, 2.1 Hz, 1H), 7.65 (d, J=8.3 Hz, 1H), 6.00 (ddt, J=16.9, 10.2, 6.5 Hz, 1H), 5.21-5.08 (m, 2H), 3.93 (s, 3H), 3.57 (d, J=6.5 Hz, 2H).

COMPOUND 24. Compound 23 (2.25 g, 8.82 mmol) in THF (1 mL) was added to a solution of LiAlH$_4$ (10.58 mL, 10.58 mmol) in THF (18 mL) at 0° C. The reaction mixture was stirred at 0° C. for 1 h and quenched with water (0.25 mL, 14.11 mmol), 20% aqueous NaOH (0.25 mL) and water (0.25 mL). To the resulting suspension was added CELITE™ and the mixture was filtered. The filtrate was concentrated to give crude compound 24 (1.61 g, 7.09 mmol, 80% yield) as a colorless oil, which was used without purification. $^1$H NMR (400 MHz, chloroform-d) δ 7.52 (d, J=8.1 Hz, 1H), 7.22 (d, J=2.0 Hz, 1H), 7.06 (dd, J=8.1, 2.2 Hz, 1H), 5.98 (ddt, J=16.9, 10.3, 6.5 Hz, 1H), 5.18-5.06 (m, 2H), 4.60 (d, J=4.9 Hz, 2H), 3.52 (d, J=6.5 Hz, 2H), 2.63 (br t, J=5.4 Hz, 1H).

COMPOUNDS 29 and 30. Compounds 29 (E-isomer) and 30 (Z-isomer) were synthesized from compound 24 per the scheme shown in FIG. 2A and separated, using procedures analogous to those described above.

COMPOUND 29. MS (ESI) m/z 480.0 (M+H); $^1$H NMR (400 MHz, chloroform-d) δ 7.44 (d, J=8.1 Hz, 1H), 7.40 (d, J=1.6 Hz, 1H), 7.22 (dd, J=8.1, 2.1 Hz, 1H), 5.58 (dt, J=15.0, 7.4 Hz, 1H), 5.48-5.36 (m, 1H), 5.15 (br s, 2H), 4.63 (br s, 2H), 4.20 (q, J=7.1 Hz, 2H), 3.34 (d, J=7.2 Hz, 2H), 2.56 (q, J=6.0 Hz, 2H), 1.25 (t, J=7.0 Hz, 3H); HH-decoupling NMR showed vinyl proton at 5.58 ppm with a coupling constant J=15.12 Hz which is consistent with trans double bond configuration.

COMPOUND 30. MS (ESI) m/z 480.0 (M+H); $^1$H NMR (400 MHz, chloroform-d) δ 7.88 (br s, 1H), 7.48 (d, J=8.1 Hz, 1H), 7.13 (dd, J=8.1, 1.7 Hz, 1H), 6.02-5.94 (m, 1H), 5.48 (dt, J=10.7, 7.9 Hz, 1H), 4.99 (s, 2H), 4.49-4.40 (m, 2H), 4.19 (q, J=7.2 Hz, 2H), 3.49 (d, J=8.1 Hz, 2H), 2.59 (br s, 2H), 1.22 (t, J=7.1 Hz, 3H); HH-decoupling NMR showed vinyl proton at 5.96 ppm with a coupling constant J=10.85 Hz, which is consistent with cis double bond configuration.

COMPOUND 33. A mixture of compound 31 (0.388 g, 2 mmol), 1-bromo-2-chloroethane 32 (0.25 mL, 3.00 mmol) and Cs$_2$CO$_3$ (1.95 g, 6.00 mmol) in acetonitrile (10 mL) was heated at 70° C. for 6 h. LCMS showed completion of the reaction. The reaction mixture was diluted with EtOAc and washed with water and brine. The organic layer was dried over MgSO$_4$ and concentrated in vacuo. The crude product was purified by flash chromatography on silica gel using an automated ISCO system (80 g column, eluting with 5-25% acetone/hexanes, monitored at 220 nm). Compound 33 (0.51 g, 1.988 mmol, 99% yield) was obtained as a colorless oil. MS (ESI) m/z 257.0 (M+H); $^1$H NMR (400 MHz, chloroform-d) δ 7.85 (s, 1H), 7.79 (s, 1H), 4.46 (t, J=6.0 Hz, 2H), 3.91 (t, J=6.0 Hz, 2H), 1.34 (s, 12H).

COMPOUND 34. A mixture of compound 33 (0.51 g, 1.988 mmol), cyclopropanamine 16 (1.135 g, 19.88 mmol) and potassium iodide (0.330 g, 1.988 mmol) in DMF (10 mL) was heated at 80° C. overnight. The reaction mixture was diluted with EtOAc and washed with water and brine. The organic layer was dried over $MgSO_4$ and concentrated in vacuo. The crude product was purified by flash chromatography on silica gel using an automated ISCO system (80 g column, eluting with 1-8% 2 N ammonia in MeOH/DCM). Compound 34 (450 mg, 1.624 mmol, 82% yield) was obtained as a brown oil. MS (ESI) m/z 278.1 (M+H); $^1$H NMR (500 MHz, chloroform-d) δ 8.26 (d, J=12.0 Hz, 1H), 8.15 (s, 1H), 7.81 (s, 1H), 7.73 (s, 1H), 4.26 (t, J=5.9 Hz, 2H), 3.16 (t, J=5.9 Hz, 2H), 2.75 (tq, J=7.1, 3.5 Hz, 1H), 2.66 (tt, J=6.6, 3.5 Hz, 1H), 2.15 (tt, J=6.6, 3.5 Hz, 1H), 1.33 (s, 12H), 1.26 (s, 34H), 0.86-0.78 (m, 4H), 0.69-0.63 (m, 1H), 0.60-0.54 (m, 2H), 0.48-0.41 (m, 2H), 0.36-0.31 (m, 2H).

COMPOUND 35. A solution of compound 34 (0.45 g, 1.624 mmol), Boc-anhydride (0.354 g, 1.624 mmol) and DIEA (0.425 mL, 2.435 mmol) in DCM (16 mL) was stirred at RT for 1.5 h. LCMS showed completion of the reaction. Solvent was evaporated in vacuo. The crude product was purified by flash chromatography on silica gel using an automated ISCO system (40 g column, eluting with 0-40% EtOAc/hexanes). Compound 35 (263 mg, 0.697 mmol, 42.9% yield) was obtained as a colorless oil. MS (ESI) m/z 378.3 (M+H); $^1$H NMR (400 MHz, chloroform-d) δ 7.80 (s, 1H), 7.63 (s, 1H), 4.30 (t, J=6.0 Hz, 2H), 3.63 (t, J=6.1 Hz, 2H), 2.25 (br d, J=1.9 Hz, 1H), 1.45 (s, 9H), 1.32 (s, 6H), 1.25 (s, 6H), 0.62 (br d, J=5.2 Hz, 2H), 0.39 (br s, 2H).

COMPOUND 36. A mixture of compound 29 (40 mg, 0.084 mmol), compound 35 (34.7 mg, 0.092 mmol), $PdCl_2$(dppf)-$CH_2Cl_2$ adduct (6.83 mg, 8.36 μmol) and potassium phosphate (53.3 mg, 0.251 mmol) in 1,4-dioxane (2 mL) was evacuated and back filled with nitrogen three times and heated at 85° C. overnight. The reaction mixture was diluted with EtOAc and washed with water and brine. The organic layer was dried over $MgSO_4$ and concentrated in vacuo. The crude product was purified by flash chromatography on silica gel using an automated ISCO system (24 g column, eluting with 5-60% EtOAc/hexanes). Compound 36 (44 mg, 0.068 mmol, 81% yield) was obtained as a yellow oil. MS (ESI) m/z 649.2 (M+H).

COMPOUND IIb-01. A mixture of compound 36 (55 mg, 0.085 mmol) and iron (28.4 mg, 0.509 mmol) in acetic acid/water (1.8 mL, 5/1) was heated at 85° C. for 4 h. LCMS showed a mixture of the desired product and the mono-Boc product. Solvent was evaporated in vacuo. The reaction mixture was suspended in 25% MeOH/DCM (3 mL) and the solid was filtered. The filtrate was concentrated and was treated with 25% TFA in dichloroethane (1 mL) at RT for 1 h. Solvent was evaporated and the crude product was dissolved in 25% MeOH/DCM (3 mL) and loaded onto a 12 g dry column, purified by flash chromatography on silica gel using an automated ISCO system (40 g gold column, eluting with 2-16% 2 N $NH_3$ in MeOH/DCM). Pure fractions were pooled and concentrated to give compound IIb-01 (18 mg, 0.037 mmol, 44.0% yield) as a white solid. MS (ESI) m/z 473.4 (M+H); $^1$H NMR (400 MHz, DMSO-$d_6$) δ 9.86 (br s, 1H), 8.17 (s, 1H), 7.87 (s, 1H), 7.57 (s, 1H), 7.25 (d, J=7.7 Hz, 1H), 7.15 (br d, J=8.3 Hz, 1H), 6.40 (br s, 2H), 5.72-5.62 (m, 1H), 5.50-5.38 (m, 1H), 4.82 (s, 2H), 4.72 (br s, 2H), 4.16 (t, J=6.4 Hz, 2H), 3.27 (br d, J=6.8 Hz, 2H), 2.98 (t, J=6.3 Hz, 2H), 2.42 (br d, J=4.5 Hz, 2H), 2.45-2.38 (m, 2H), 2.07 (tt, J=6.5, 3.4 Hz, 1H), 0.37-0.30 (m, 2H), 0.19-0.13 (m, 2H).

Additional compounds were prepared by methods analogous to those described above, mutatis mutandis.

COMPOUND IIb-02. MS (ESI) m/z 475.4 (M+H); $^1$H NMR (400 MHz, DMSO-$d_6$) δ 9.88 (br s, 1H), 8.00 (d, J=1.4 Hz, 1H), 7.88 (s, 1H), 7.57 (s, 1H), 7.25 (d, J=7.8 Hz, 1H), 7.15 (dd, J=7.9, 1.6 Hz, 1H), 6.41 (br s, 2H), 5.72-5.63 (m, 1H), 5.60-5.51 (m, 1H), 4.82 (s, 2H), 4.55-4.44 (m, 2H), 4.17 (t, J=6.4 Hz, 2H), 3.37 (br d, J=7.9 Hz, 2H), 2.98 (t, J=6.3 Hz, 2H), 2.42-2.34 (m, 2H), 2.11-2.04 (m, 1H), 0.37-0.30 (m, 2H), 0.19-0.13 (m, 2H).

COMPOUND IIb-03. MS (ESI) m/z 473.4 (M+H); $^1$H NMR (500 MHz, DMSO-$d_6$) δ 7.75 (s, 1H), 7.70 (d, J=1.6 Hz, 1H), 7.49 (d, J=0.6 Hz, 1H), 7.21 (d, J=7.8 Hz, 1H), 7.02 (dd, J=7.9, 1.8 Hz, 1H), 6.08 (s, 2H), 4.87 (s, 2H), 4.29 (t, J=6.9 Hz, 2H), 4.18 (t, J=6.3 Hz, 2H), 3.03 (t, J=6.3 Hz, 2H), 2.80-2.75 (m, 2H), 2.11 (tt, J=6.7, 3.5 Hz, 1H), 1.71-1.64 (m, 2H), 1.50-1.42 (m, 2H), 1.32 (dt, J=13.5, 7.0 Hz, 2H), 0.38-0.33 (m, 2H), 0.22-0.17 (m, 2H).

COMPOUND IIb-04. MS (ESI) m/z 470.2 (M+H); $^1$H NMR (500 MHz, DMSO-$d_6$) δ 9.95 (br s, 1H), 8.42 (s, 1H), 8.21 (s, 1H), 7.70 (br d, J=7.7 Hz, 1H), 7.46 (d, J=7.7 Hz, 1H), 7.25 (br d, J=7.7 Hz, 1H), 7.16 (d, J=7.4 Hz, 1H), 6.45 (br s, 2H), 5.66-5.56 (m, 1H), 5.49-5.38 (m, 1H), 4.89 (s, 2H), 4.70 (br s, 2H), 3.91 (s, 2H), 3.13 (br d, J=6.9 Hz, 2H), 2.39 (br d, J=5.0 Hz, 2H), 2.21-2.13 (m, 1H), 0.43-0.37 (m, 2H), 0.31 (br s, 2H).

COMPOUND IIb-05. MS (ESI) m/z 484.4 (M+H); $^1$H NMR (500 MHz, DMSO-$d_6$) δ 9.95 (br. s, 1H), 8.40 (s, 1H), 8.21 (s, 1H), 7.69 (br d, J=8.0 Hz, 1H), 7.46 (br d, J=8.3 Hz, 1H), 7.25 (br d, J=7.7 Hz, 1H), 7.16 (d, J=7.7 Hz, 1H), 6.44 (br s, 2H), 5.67-5.55 (m, 1H), 5.50-5.38 (m, 1H), 4.89 (s, 2H), 4.69 (br s, 2H), 3.76 (s, 2H), 3.12 (br d, J=6.9 Hz, 2H), 2.42-2.35 (m, 2H), 2.12-1.99 (m, 2H), 1.77-1.47 (m, 4H).

COMPOUND IIb-06. MS (ESI) m/z 390.1 (M+H); $^1$H NMR (500 MHz, DMSO-$d_6$) δ 8.14 (s, 1H), 7.70 (br s, 2H), 7.24 (d, J=7.7 Hz, 1H), 7.16 (br d, J=7.5 Hz, 1H), 6.30 (br s, 1H), 5.73-5.62 (m, 1H), 5.44 (dt, J=15.2, 7.4 Hz, 1H), 4.85 (s, 2H), 4.76-4.67 (m, 2H), 3.27 (br d, J=6.8 Hz, 2H), 2.42 (br d, J=5.3 Hz, 2H).

COMPOUND IIb-07. MS (ESI) m/z 487.2 (M+H); $^1$H NMR (400 MHz, DMSO-$d_6$) δ 9.87 (br s, 1H), 8.17 (d, J=1.6 Hz, 1H), 7.87 (s, 1H), 7.57 (d, J=0.7 Hz, 1H), 7.25 (d, J=7.8 Hz, 1H), 7.15 (dd, J=7.8, 1.8 Hz, 1H), 6.40 (s, 2H), 5.73-5.62 (m, 1H), 5.44 (dt, J=15.3, 7.5 Hz, 1H), 4.82 (s, 2H), 4.76-4.68 (m, 2H), 4.12 (t, J=6.4 Hz, 2H), 3.27 (br d, J=7.1 Hz, 2H), 3.18-3.08 (m, 1H), 2.84 (t, J=6.4 Hz, 2H), 2.45-2.38 (m, 2H), 2.11-2.00 (m, 2H), 1.66-1.48 (m, 4H).

COMPOUND IIb-08. MS (ESI) m/z 489.3 (M+H); $^1$H NMR (400 MHz, DMSO-$d_6$) δ 9.97 (br s, 1H), 7.88 (s, 1H), 7.70 (d, J=1.5 Hz, 1H), 7.58 (s, 1H), 7.24 (d, J=7.8 Hz, 1H), 7.01 (dd, J=8.0, 1.7 Hz, 1H), 6.39 (s, 2H), 4.86-4.86 (m, 1H), 4.28 (br t, J=6.8 Hz, 2H), 4.20 (t, J=6.3 Hz, 2H), 3.43-3.23 (m, 3H), 2.96 (t, J=6.3 Hz, 2H), 2.78 (dt, J=5.3, 2.5 Hz, 2H), 2.16-2.03 (m, 2H), 1.78-1.54 (m, 6H), 1.46-1.37 (m, 2H), 1.33-1.26 (m, 2H).

COMPOUND IIb-09. MS (ESI) m/z 487.3 (M+H); $^1$H NMR (500 MHz, DMSO-$d_6$) δ 10.01 (s, 1H), 8.83 (br s, 1H), 8.03 (s, 1H), 7.97 (s, 1H), 7.72 (s, 1H), 7.28 (d, J=8.0 Hz, 1H), 7.19 (d, J=8.0 Hz, 1H), 6.46 (br s, 2H), 5.73-5.65 (m, 1H), 5.62-5.55 (m, 1H), 4.84 (s, 2H), 4.54-4.47 (m, 2H), 4.42 (t, J=6.2 Hz, 2H), 3.69 (br t, J=8.0 Hz, 1H), 3.32 (br t, J=6.2 Hz, 2H), 2.44-2.36 (m, 2H), 2.19-2.08 (m, 4H), 1.84-1.69 (m, 2H).

COMPOUND IIb-29. MS (ESI) m/z 498.2 (M+H); $^1$H NMR (500 MHz, DMSO-$d_6$) δ 8.13 (s, 1H), 7.84 (br t, J=6.9 Hz, 1H), 7.80-7.74 (m, 1H), 7.56-7.44 (m, 2H), 7.27 (br d, J=7.4 Hz, 1H), 7.19 (br d, J=7.7 Hz, 1H), 6.51 (br s, 2H), 5.65-5.49 (m, 2H), 4.89 (s, 2H), 4.55-4.48 (m, 2H), 3.22-3.16 (m, 2H), 2.46-2.36 (m, 2H), 1.77 (br s, 2H).

COMPOUND IIb-30. MS (ESI) m/z 498.1 (M+H); $^1$H NMR (500 MHz, DMSO-$d_6$) δ 8.15 (s, 1H), 7.93-7.85 (m, 2H), 7.45-7.37 (m, 2H), 7.26 (br d, J=7.7 Hz, 1H), 7.18 (br d, J=7.7 Hz, 1H), 6.50 (br s, 2H), 5.65-5.57 (m, 1H), 5.56-5.49 (m, 1H), 4.88 (s, 2H), 4.55-4.48 (m, 2H), 3.21 (br d, J=7.4 Hz, 2H), 2.46-2.36 (m, 2H), 1.81 (br s, 2H).

COMPOUND IIb-31. MS (ESI) m/z 498.2 (M+H); $^1$H NMR (500 MHz, DMSO-$d_6$) δ 10.04 (br s, 1H), 9.07 (br d, J=6.6 Hz, 1H), 8.20 (s, 1H), 7.86 (br d, J=7.4 Hz, 1H), 7.78 (s, 1H), 7.59-7.54 (m, 1H), 7.53-7.49 (m, 1H), 7.27 (br d, J=8.0 Hz, 1H), 7.18 (d, J=7.7 Hz, 1H), 6.48 (br s, 2H), 5.66-5.56 (m, 1H), 5.49-5.39 (m, 1H), 4.91 (s, 2H), 4.85-4.76 (m, 1H), 4.70 (br d, J=1.4 Hz, 2H), 4.22-4.15 (m, 2H), 4.14-4.06 (m, 2H), 3.11 (br d, J=6.6 Hz, 2H), 2.40 (br d, J=4.4 Hz, 2H).

COMPOUND IIb-32. MS (ESI) m/z 498.2 (M+H); $^1$H NMR (500 MHz, DMSO-$d_6$) δ 9.05 (br d, J=6.9 Hz, 1H), 8.17 (s, 1H), 7.89 (d, J=8.3 Hz, 2H), 7.39 (d, J=8.0 Hz, 2H), 7.25 (br d, J=8.0 Hz, 1H), 7.15 (d, J=7.7 Hz, 1H), 6.50 (br s, 2H), 5.64-5.55 (m, 1H), 5.42 (dt, J=15.2, 7.4 Hz, 1H), 4.89 (s, 2H), 4.80-4.73 (m, 1H), 4.68 (br s, 2H), 3.12 (br d, J=6.9 Hz, 2H), 2.38 (br d, J=5.5 Hz, 2H), 1.82 (s, 2H).

COMPOUND IIb-35. MS (ESI) m/z 445.1 (M+H); $^1$H NMR (500 MHz, DMSO-$d_6$) δ 8.19 (s, 1H), 8.05-8.00 (m, 1H), 7.67 (s, 1H), 7.27 (br d, J=7.7 Hz, 1H), 7.17 (br d, J=8.3 Hz, 1H), 6.53 (br s, 2H), 5.68 (dt, J=15.7, 7.0 Hz, 1H), 5.50-5.40 (m, 1H), 4.84 (s, 2H), 4.73 (br d, J=3.3 Hz, 2H), 4.01-3.92 (m, 1H), 3.78-3.69 (m, 2H), 3.29 (br d, J=6.6 Hz, 2H), 2.43 (br d, J=5.2 Hz, 2H).

COMPOUND IIb-36. MS (ESI) m/z 473.1 (M+H); $^1$H NMR (500 MHz, DMSO-$d_6$) δ 8.18 (s, 1H), 7.91 (s, 1H), 7.59 (s, 1H), 7.26 (d, J=7.7 Hz, 1H), 7.16 (br d, J=7.7 Hz, 1H), 6.46 (br s, 2H), 5.72-5.64 (m, 1H), 5.49-5.40 (m, 1H), 4.84 (s, 2H), 4.73 (br s, 2H), 4.28-4.20 (m, 1H), 3.08 (br d, J=11.6 Hz, 2H), 2.68-2.60 (m, 2H), 2.46-2.39 (m, 2H), 2.02-1.96 (m, 2H), 1.90 (s, 2H), 1.84 (br dd, J=12.0, 3.7 Hz, 2H).

COMPOUND IIb-37. MS (ESI) m/z 503.2 (M+H); $^1$H NMR (500 MHz, DMSO-$d_6$) δ 9.97 (s, 1H), 8.19 (s, 1H), 7.93 (s, 1H), 7.61 (br s, 1H), 7.26 (d, J=7.8 Hz, 1H), 7.17 (br d, J=7.9 Hz, 1H), 6.46 (br s, 2H), 5.74-5.64 (m, 1H), 5.45 (dt, J=15.3, 7.6 Hz, 1H), 4.84 (s, 2H), 4.73 (br s, 2H), 4.29 (br s, 2H), 3.64-3.53 (m, 4H), 3.28 (br d, J=6.9 Hz, 2H), 2.45-2.39 (m, 3H).

COMPOUND IIb-38. MS (ESI) m/z 502.2 (M+H); $^1$H NMR (500 MHz, DMSO-$d_6$) δ 8.19 (s, 1H), 7.86 (s, 1H), 7.61 (s, 1H), 7.26 (br d, J=7.7 Hz, 1H), 7.20-7.16 (m, 1H), 6.44 (br s, 2H), 5.71-5.65 (m, 1H), 5.47 (br dd, J=15.0, 7.8 Hz, 1H), 4.84 (s, 2H), 4.81 (s, 1H), 4.76-4.70 (m, 2H), 3.73-3.68 (m, 2H), 3.28 (br d, J=7.2 Hz, 2H), 2.45-2.40 (m, 2H), 1.91 (s, 2H).

COMPOUND IIb-39. MS (ESI) m/z 502.1 (M+H); $^1$H NMR (400 MHz, DMSO-$d_6$) δ 8.70 (br d, J=7.0 Hz, 1H), 8.02 (s, 1H), 7.85 (s, 1H), 7.59 (s, 1H), 7.26 (br d, J=7.9 Hz, 1H), 7.16 (br dd, J=8.1, 1.5 Hz, 1H), 6.57 (br s, 2H), 5.73-5.63 (m, 2H), 5.61-5.53 (m, 2H), 4.81 (br d, J=14.8 Hz, 4H), 4.54-4.46 (m, 3H), 3.56-3.50 (m, 3H), 2.67 (dt, J=3.7, 1.8 Hz, 1H), 2.44-2.36 (m, 2H), 2.35-2.32 (m, 1H).

Figure 3:
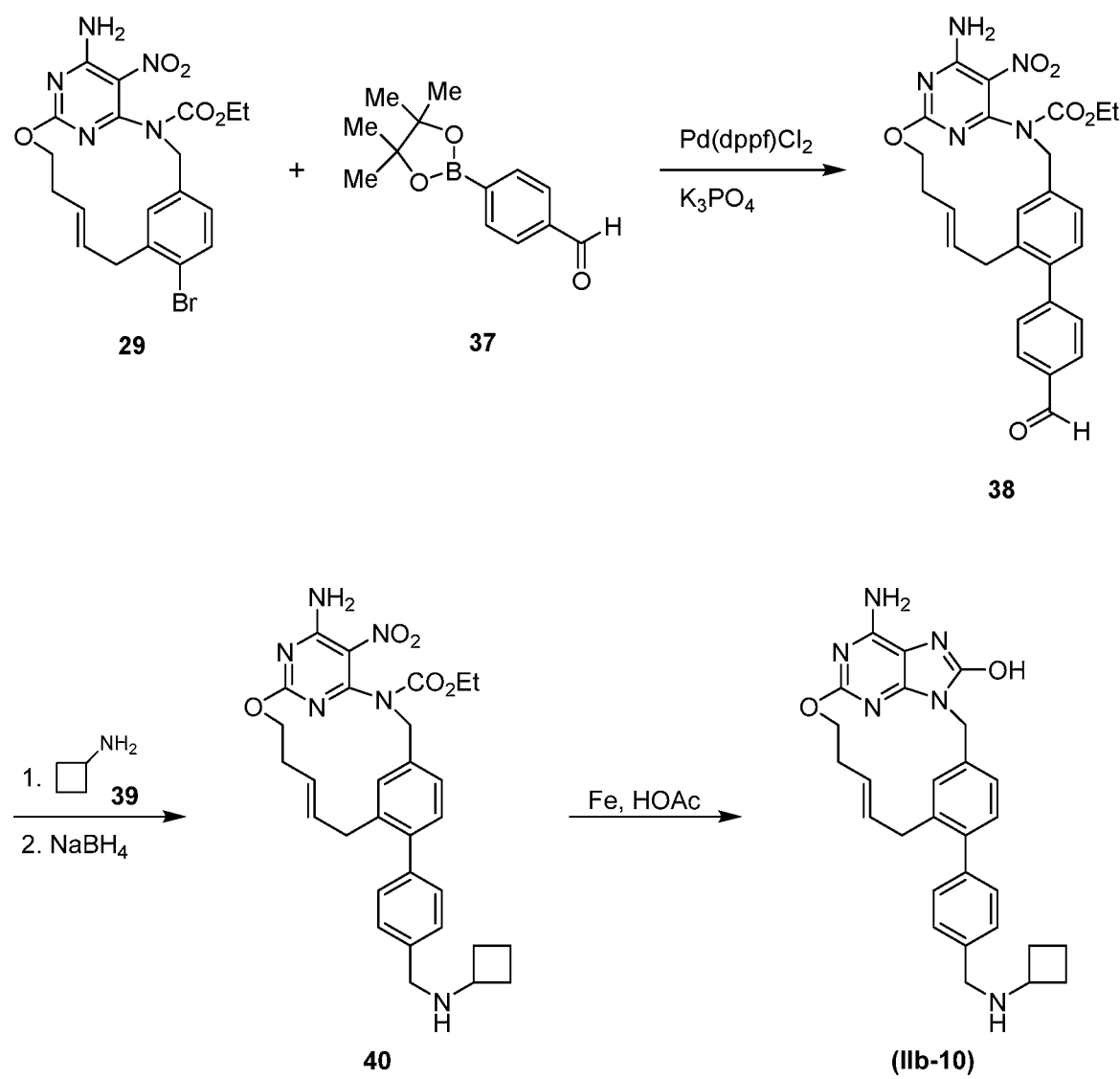

Example 3—Synthesis of Compounds According to FIG. 3

This example relates to the synthesis of compounds according to the scheme of FIG. 3, with compound (IIb-10) being used as an exemplar.

COMPOUND 38. A mixture of compound 29 (40 mg, 0.084 mmol), compound 37 (23.3 mg, 0.100 mmol), 1,1'-bis(diphenylphosphino)ferrocenedichloro palladium(II) DCM complex (Pd(dppf)Cl$_2$, 6.8 mg, 8.36 μmol) and K$_3$PO$_4$ (53.3 mg, 0.251 mmol) in 1,4-dioxane (2 mL) was evacuated, back filled with nitrogen three times and heated at 85° C. overnight. The reaction mixture was diluted with EtOAc and washed with water and brine. The organic layer was dried over MgSO$_4$ and concentrated in vacuo. The crude product was purified by flash chromatography on silica gel using an automated ISCO system (24 g column, eluting with 10-90% EtOAc/hexanes). Compound 38 (32 mg, 0.064 mmol, 76% yield) was obtained as a foaming solid. MS (ESI) m/z 504.1 (M+H).

COMPOUND 40. A solution of compound 38 (32 mg, 0.064 mmol) and cyclobutanamine 39 (7.0 μl, 0.083 mmol) in MeOH (0.6 mL)/DCM (0.6 mL) was stirred at RT overnight. NaBH$_4$ (3.6 mg, 0.095 mmol) was added to the reaction mixture, which was then stirred at RT for 15 min. The reaction mixture was diluted with EtOAc and washed with water and brine. The organic layer was dried over MgSO$_4$ and concentrated in vacuo. The crude product was purified by flash chromatography on silica gel using an automated ISCO system (24 g gold column, eluting with 1-6% 2 N NH$_3$ in MeOH/DCM) to give compound 40 (27 mg, 0.048 mmol, 76% yield) as a foaming solid. MS (ESI) m/z 559.5 (M+H).

COMPOUND IIb-10. A mixture of compound 40 (27 mg, 0.048 mmol) and iron (21.6 mg, 0.387 mmol) in HOAc (0.80 mL)/water (0.16 mL) was heated at 85° C. for 45 min. Solvent was evaporated in vacuo. The residue was suspended in 25% MeOH/DCM and filtered. The filtrate was concentrated and the crude product was dissolved in 25% MeOH/DCM and absorbed onto silica, purified by flash chromatography on silica gel using an automated ISCO system (24 g column, eluting with 2-18% 2 N NH$_3$ in MeOH/DCM) to afford compound IIb-10 (16 mg, 0.032 mmol, 66.5% yield) as a white solid. MS (ESI) m/z 483.2 (M+H); $^1$H NMR (500 MHz, DMSO-$d_6$) δ 8.16 (d, J=1.3 Hz, 1H), 7.34 (d, J=8.0 Hz, 2H), 7.20 (d, J=8.0 Hz, 3H), 7.10 (d, J=7.7 Hz, 1H), 6.48 (br s, 2H), 5.64-5.54 (m, 1H), 5.42 (dt, J=15.2, 7.5 Hz, 1H), 4.86 (s, 2H), 4.68 (br s, 2H), 3.62 (s, 3H), 3.20-3.14 (m, 1H), 3.12 (br d, J=6.9 Hz, 2H), 2.41-2.34 (m, 2H), 2.12-2.02 (m, 2H), 1.88 (s, 2H), 1.74-1.46 (m, 4H).

Additional compounds were prepared by methods analogous to those described above, mutatis mutandis.

COMPOUND IIb-11. MS (ESI) m/z 483.3 (M+H); $^1$H NMR (500 MHz, DMSO-$d_6$) δ 8.12 (s, 1H), 7.34 (d, J=7.7 Hz, 2H), 7.21 (br d, J=8.0 Hz, 3H), 7.12 (d, J=7.7 Hz, 1H), 6.49 (br s, 2H), 5.64-5.56 (m, 1H), 5.53-5.46 (m, 1H), 4.85 (s, 2H), 4.54-4.45 (m, 2H), 3.62 (s, 2H), 3.20 (br d, J=8.0 Hz, 2H), 3.18-3.13 (m, 1H), 2.45-2.37 (m, 2H), 2.10-2.02 (m, 2H), 1.86 (s, 2H), 1.75-1.65 (m, 2H), 1.64-1.57 (m, 1H), 1.56-1.49 (m, 1H).

COMPOUND IIb-12. MS (ESI) m/z 485.5 (M+H); $^1$H NMR (400 MHz, methanol-$d_4$) δ 7.73 (d, J=1.2 Hz, 1H), 7.32 (d, J=8.1 Hz, 2H), 7.19 (d, J=8.1 Hz, 2H), 7.13-7.04 (m, 2H), 5.01 (s, 2H), 4.37 (t, J=7.0 Hz, 2H), 3.72 (s, 2H), 3.40-3.34 (m, 1H), 2.74-2.60 (m, 2H), 2.28-2.18 (m, 2H), 1.87-1.67 (m, 4H), 1.65-1.56 (m, 2H), 1.49 (quin, J=7.0 Hz, 2H), 1.36-1.22 (m, 6H).

COMPOUND IIb-16. MS (ESI) m/z 497.4 (M+H); $^1$H NMR (500 MHz, DMSO-$d_6$) δ 7.90 (s, 1H), 7.37 (br d, J=8.0 Hz, 2H), 7.25 (br d, J=8.3 Hz, 1H), 7.21 (br d, J=8.0 Hz, 2H), 7.14 (d, J=7.7 Hz, 1H), 6.40 (br s, 2H), 5.51-5.42 (m, 1H), 5.33-5.25 (m, 1H), 4.84 (s, 2H), 4.62-4.55 (m, 2H), 3.67 (s, 2H), 3.23 (br d, J=6.9 Hz, 3H), 2.08 (br s, 4H), 1.91 (s, 2H), 1.79-1.69 (m, 4H), 1.68-1.52 (m, 2H).

COMPOUND IIb-17. MS (ESI) m/z 497.5 (M+H); $^1$H NMR (500 MHz, DMSO-$d_6$) δ 7.74 (s, 1H), 7.36 (d, J=7.7 Hz, 2H), 7.24 (d, J=8.0 Hz, 2H), 7.21 (br d, J=8.5 Hz, 1H), 7.11 (d, J=7.7 Hz, 1H), 6.63 (br s, 2H), 5.54-5.44 (m, 1H), 5.27-5.16 (m, 1H), 4.81 (s, 2H), 4.37-4.29 (m, 2H), 3.64 (s, 2H), 3.21-3.12 (m, 2H), 2.16-2.03 (m, 4H), 1.81 (br s, 3H), 1.72-1.59 (m, 3H), 1.57-1.47 (m, 3H).

COMPOUND IIb-18. MS (ESI) m/z 499.4 (M+H); $^1$H NMR (500 MHz, DMSO-$d_6$) δ 7.51 (s, 1H), 7.34 (d, J=8.0 Hz, 2H), 7.21 (br d, J=8.3 Hz, 1H), 7.16 (d, J=7.7 Hz, 2H), 7.09 (d, J=7.7 Hz, 1H), 6.44 (br s, 2H), 4.88 (s, 2H), 4.44 (br t, J=6.5 Hz, 2H), 3.63 (s, 2H), 3.18 (br t, J=7.6 Hz, 2H), 2.59-2.56 (m, 1H), 2.12-2.03 (m, 2H), 1.90 (s, 2H), 1.73-1.59 (m, 3H), 1.58-1.49 (m, 3H), 1.39-1.25 (m, 4H), 1.21-1.14 (m, 2H).

COMPOUND IIb-21. MS (ESI) m/z 499.4 (M+H); $^1$H NMR (500 MHz, DMSO-$d_6$) δ 10.05 (s, 1H), 9.08 (br d, J=2.5 Hz, 2H), 8.14 (s, 1H), 7.52 (br d, J=8.0 Hz, 2H), 7.38 (br d, J=8.0 Hz, 2H), 7.28-7.21 (m, 1H), 7.18-7.11 (m, 1H), 6.47 (br s, 1H), 5.64-5.57 (m, 1H), 5.56-5.49 (m, 1H), 4.87 (s, 2H), 4.56-4.46 (m, 2H), 4.35 (br d, J=6.6 Hz, 1H), 4.08 (br s, 2H), 3.80 (br d, J=5.8 Hz, 2H), 3.21 (br d, J=7.2 Hz, 2H), 2.45-2.38 (m, 4H), 2.20-2.11 (m, 2H).

COMPOUND IIb-22. MS (ESI) m/z 499.4 (M+H); $^1$H NMR (500 MHz, DMSO-$d_6$) δ 8.14 (s, 1H), 7.51 (br d, J=8.2 Hz, 2H), 7.37 (br d, J=7.9 Hz, 2H), 7.25 (d, J=8.2 Hz, 1H), 7.14 (d, J=7.6 Hz, 1H), 6.48 (br s, 2H), 5.65-5.57 (m, 1H), 5.56-5.47 (m, 2H), 4.88 (s, 2H), 4.56-4.48 (m, 2H), 4.05 (br s, 2H), 3.96-3.88 (m, 1H), 3.23-3.15 (m, 5H), 2.42 (br d, J=7.5 Hz, 2H), 2.01-1.92 (m, 2H).

COMPOUND IIb-23. MS (ESI) m/z 499.4 (M+H); $^1$H NMR (500 MHz, DMSO-$d_6$) δ 8.16 (s, 1H), 7.37 (br d, J=7.9 Hz, 2H), 7.26-7.19 (m, 3H), 7.11 (d, J=7.6 Hz, 1H), 6.47 (br s, 2H), 5.64-5.55 (m, 1H), 5.47-5.36 (m, 1H), 4.88 (s, 2H), 4.69 (br s, 2H), 4.32-4.22 (m, 1H), 3.39-3.33 (m, 2H), 3.12 (br d, J=6.8 Hz, 2H), 2.38 (br d, J=4.3 Hz, 2H), 2.11-2.04 (m, 2H), 1.96 (ddd, J=12.3, 7.5, 4.9 Hz, 2H), 1.91 (s, 2H).

COMPOUND IIb-24. MS (ESI) m/z 499.4 (M+H); $^1$H NMR (500 MHz, DMSO-$d_6$) δ 8.17 (br s, 1H), 7.37 (br d, J=6.8 Hz, 2H), 7.27-7.19 (m, 3H), 7.14-7.09 (m, 1H), 6.47 (br s, 2H), 5.65-5.55 (m, 1H), 5.47-5.36 (m, 1H), 4.88 (s, 2H), 4.69 (br s, 2H), 3.78-3.74 (m, 1H), 3.69 (br s, 3H), 3.12 (br s, 2H), 2.73 (br t, J=7.2 Hz, 2H), 2.46-2.33 (m, 4H), 1.91 (s, 2H), 1.68-1.56 (m, 2H).

COMPOUND IIb-25. MS (ESI) m/z 519.4 (M+H); $^1$H NMR (500 MHz, DMSO-$d_6$) δ 9.98 (br s, 1H), 8.16 (s, 1H), 7.37 (br d, J=7.7 Hz, 2H), 7.27-7.18 (m, 3H), 7.11 (d, J=7.7 Hz, 1H), 6.44 (br s, 2H), 5.64-5.54 (m, 1H), 5.42 (dt, J=15.0, 7.4 Hz, 1H), 4.87 (s, 2H), 4.68 (br s, 2H), 3.70 (s, 2H), 3.19 (br dd, J=9.8, 4.8 Hz, 2H), 3.12 (br d, J=6.9 Hz, 2H), 2.81-2.67 (m, 2H), 2.38 (br s, 4H).

COMPOUND IIb-26. MS (ESI) m/z 497.2 (M+H); $^1$H NMR (500 MHz, DMSO-$d_6$) δ 8.11 (s, 1H), 7.39 (d, J=7.9 Hz, 2H), 7.22 (d, J=7.9 Hz, 2H), 7.12 (d, J=7.8 Hz, 1H), 6.45 (br s, 2H), 5.64-5.55 (m, 1H), 5.55-5.48 (m, 1H), 4.86 (s, 2H), 4.51 (br t, J=8.4 Hz, 2H), 3.65 (br s, 6H), 3.20 (br d, J=7.7 Hz, 2H), 2.44-2.36 (m, 2H), 2.03-1.96 (m, 1H), 1.78-1.62 (m, 3H), 1.26 (s, 3H).

COMPOUND IIb-27. MS (ESI) m/z 526.3 (M+H); $^1$H NMR (500 MHz, DMSO-$d_6$) δ 10.04 (br s, 1H), 8.12 (s, 1H), 7.37 (br d, J=7.7 Hz, 2H), 7.27-7.20 (m, 3H), 7.13 (d, J=8.0 Hz, 1H), 6.44 (br s, 2H), 5.63-5.55 (m, 1H), 5.55-5.47 (m, 1H), 4.86 (s, 2H), 4.54-4.47 (m, 2H), 4.29 (br s, 1H), 4.17 (br t, J=7.4 Hz, 1H), 3.90 (br t, J=7.4 Hz, 2H), 3.80-3.76 (m, 3H), 3.20 (br d, J=7.7 Hz, 2H), 3.17 (br d, J=2.2 Hz, 2H), 2.40 (br d, J=8.3 Hz, 2H), 1.72 (s, 3H).

COMPOUND IIb-28. MS (ESI) m/z 495.1 (M+H); $^1$H NMR (500 MHz, DMSO-$d_6$) δ 10.02 (br s, 1H), 8.13 (s, 1H), 7.38 (br d, J=7.5 Hz, 2H), 7.23 (br d, J=7.5 Hz, 3H), 7.13 (d, J=7.6 Hz, 1H), 6.47 (br s, 2H), 5.64-5.56 (m, 1H), 5.56-5.48 (m, 1H), 4.86 (s, 2H), 4.56-4.48 (m, 2H), 3.75 (s, 2H), 3.21 (br d, J=7.0 Hz, 2H), 2.46-2.39 (m, 2H), 2.35 (s, 1H), 1.72 (s, 6H).

COMPOUND IIb-33. MS (ESI) m/z 485.3 (M+H); $^1$H NMR (500 MHz, DMSO-$d_6$) δ 9.99 (br s, 1H), 8.13 (s, 1H), 7.36 (d, J=8.0 Hz, 2H), 7.26-7.20 (m, 3H), 7.14 (d, J=7.7 Hz, 1H), 6.45 (br s, 2H), 5.65-5.57 (m, 1H), 5.55-5.48 (m, 1H), 4.87 (s, 2H), 4.56 (t, J=6.6 Hz, 2H), 4.54-4.49 (m, 2H), 4.31 (t, J=6.2 Hz, 2H), 3.93-3.86 (m, 1H), 3.66 (s, 2H), 3.21 (br d, J=7.7 Hz, 2H), 2.46-2.39 (m, 2H).

COMPOUND IIb-34. MS (ESI) m/z 513.3 (M+H); $^1$H NMR (500 MHz, DMSO-$d_6$) δ 8.14 (s, 1H), 7.40 (d, J=8.0 Hz, 2H), 7.27-7.20 (m, 3H), 7.14 (d, J=7.4 Hz, 1H), 6.47 (br s, 2H), 5.66-5.58 (m, 1H), 5.56-5.48 (m, 1H), 4.87 (s, 2H), 4.56-4.49 (m, 2H), 3.87-3.81 (m, 2H), 3.78 (s, 2H), 3.28 (td, J=11.3, 1.8 Hz, 2H), 3.23 (br d, J=7.7 Hz, 2H), 2.70-2.62 (m, 1H), 2.47-2.40 (m, 2H), 1.91 (s, 1H), 1.85-1.77 (m, 2H), 1.36-1.25 (m, 2H).

Figure 4:
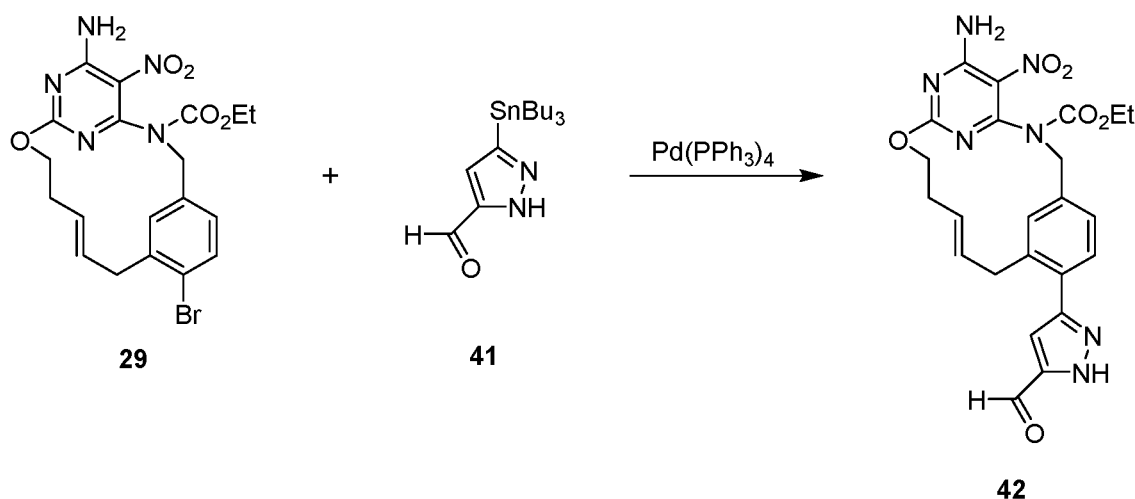
Figure 4:
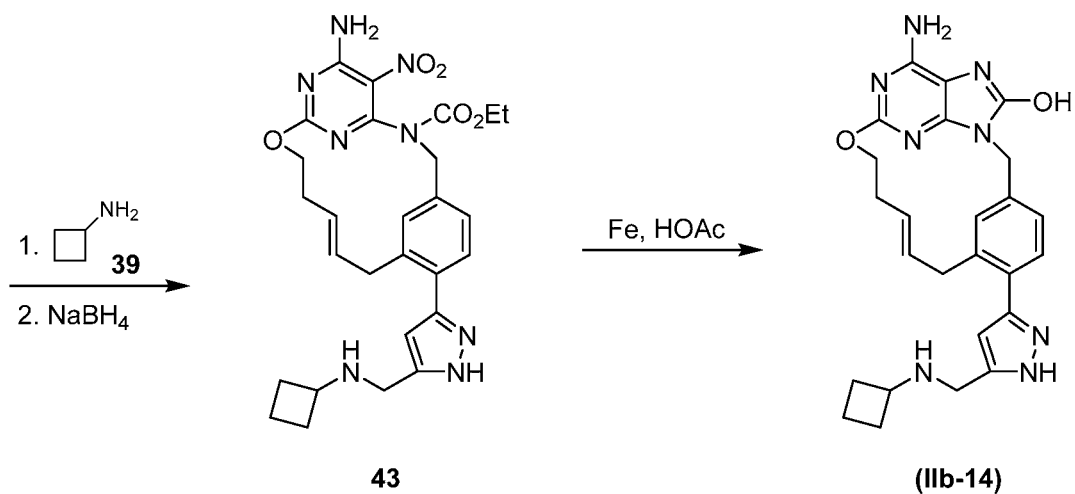

Example 4—Synthesis of Compounds According to FIG. 4

This example relates to the synthesis of compounds according to the scheme of FIG. 4, with compound (IIb-14) being used as an exemplar.

COMPOUND 42. A mixture of compound 29 (30 mg, 0.063 mmol), compound 41 (29.0 mg, 0.075 mmol) and tetrakis(triphenylphosphine)palladium(0) (P(PPh$_3$)$_4$, 7.3 mg, 6.27 μmol) in DMF (1 mL) was evacuated, back filled with nitrogen three times and heated at 85° C. overnight. The reaction mixture was diluted with EtOAc and washed with water and brine. The organic layer was dried over MgSO$_4$ and concentrated in vacuo. The crude product was purified by flash chromatography on silica gel using an automated ISCO system (24 g gold column, eluting with 5-60% EtOAc/hexanes). Compound 42 (25 mg, 0.051 mmol, 81% yield) was obtained as a colorless oil. MS (ESI) m/z 494.1 (M+H).

COMPOUND 43. A solution of compound 42 (33 mg, 0.067 mmol) and cyclobutanamine 39 (8.6 μl, 0.100 mmol) in DCM (1 mL)/MeOH (1 mL) was stirred at RT overnight. NaBH$_4$ (3.8 mg, 0.100 mmol) was added and the reaction mixture was stirred at RT for 10 min. The reaction mixture was diluted with EtOAc and washed with water and brine. The organic layer was dried over MgSO$_4$ and concentrated in vacuo. The crude product was purified by flash chromatography on silica gel using an automated ISCO system (24 g gold column, eluting with 1-6% 2 N NH$_3$ in MeOH/DCM). Compound 43 (26 mg, 0.047 mmol, 70.9% yield) was obtained as a foaming solid. MS (ESI) m/z 549.3 (M+H).

COMPOUND IIb-14. A mixture of compound 43 (26 mg, 0.047 mmol) and iron (21.2 mg, 0.379 mmol) in HOAc (2 mL)/water (0.4 mL) was heated at 85° C. for 45 min. The solvent was evaporated in vacuo. The residue was suspended in 25% MeOH/DCM and filtered. The filtrate was concentrated and the crude product was dissolved in 25% MeOH/DCM and absorbed onto silica, purified by flash chromatography on silica gel using an automated ISCO system (12 g gold column, eluting with 2-16% 2 N $NH_3$ in MeOH/DCM) to afford compound IIb-14 (16 mg, 0.033 mmol, 69.3% yield) as a white solid. MS (ESI) m/z 473.3 (M+H); $^1$H NMR (400 MHz, DMSO-$d_6$) δ 8.18 (s, 1H), 7.36 (d, J=7.7 Hz, 1H), 7.19 (br d, J=8.0 Hz, 1H), 6.56 (s, 2H), 6.28 (s, 1H), 5.73-5.61 (m, 1H), 5.44 (dt, J=15.2, 7.4 Hz, 1H), 4.85 (s, 2H), 4.71 (br s, 2H), 3.63 (s, 2H), 3.38 (br d, J=6.9 Hz, 2H), 3.26-3.14 (m, 2H), 2.41 (br d, J=4.9 Hz, 2H), 2.13-2.01 (m, 2H), 1.89 (s, 5H), 1.77-1.46 (m, 4H).

Additional compounds were prepared by methods analogous to those described above, mutatis mutandis.

COMPOUND IIb-15. MS (ESI) m/z 473.4 (M+H); $^1$H NMR (500 MHz, DMSO-$d_6$) δ 8.06 (s, 1H), 7.36 (br d, J=7.7 Hz, 1H), 7.20 (br d, J=8.3 Hz, 1H), 6.48 (br s, 2H), 6.29 (s, 1H), 5.72-5.63 (m, 1H), 5.57-5.48 (m, 1H), 4.85 (s, 2H), 4.54-4.45 (m, 2H), 3.61 (br s, 3H), 3.22-3.13 (m, 2H), 2.99 (s, 1H), 2.44-2.35 (m, 2H), 2.12-1.99 (m, 2H), 1.84 (br s, 1H), 1.73-1.48 (m, 4H).

COMPOUND IIb-40. MS (ESI) m/z 558.4 (M+H); $^1$H NMR (500 MHz, DMSO-$d_6$) δ 13.33 (br s, 1H), 10.00-9.87 (m, 1H), 8.29-8.13 (m, 2H), 7.38-7.31 (m, 1H), 7.31-7.19 (m, 1H), 6.69 (br s, 1H), 6.44 (br s, 2H), 5.72-5.61 (m, 1H), 5.51-5.41 (m, 1H), 4.88 (br s, 2H), 4.72 (br s, 2H), 3.29-3.25 (m, 2H), 3.24-3.17 (m, 5H), 2.45-2.39 (m, 2H), 2.25-2.18 (m, 2H), 1.95-1.89 (m, 2H), 1.75-1.64 (m, 2H).

Figure 5:
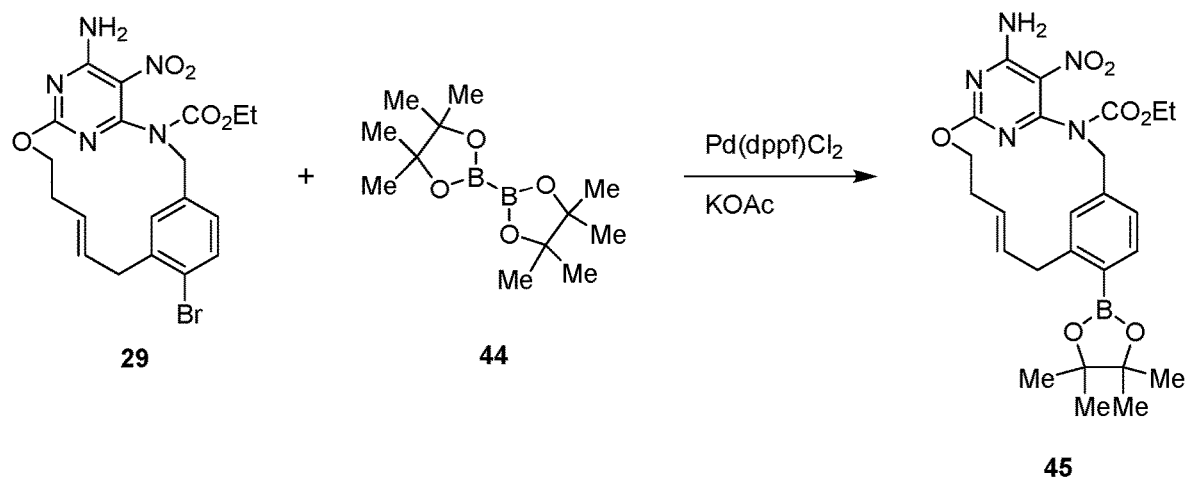
Figure 5:
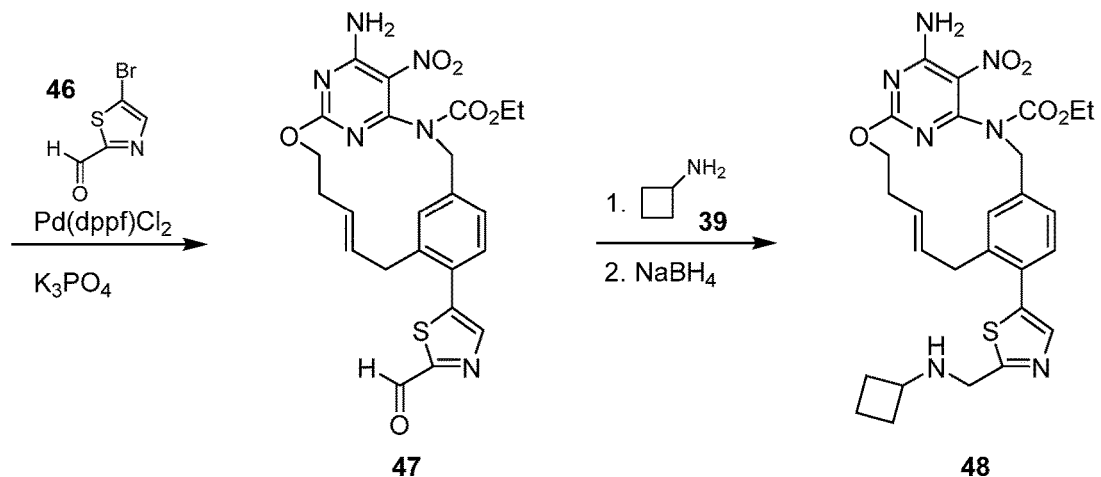
Figure 5:
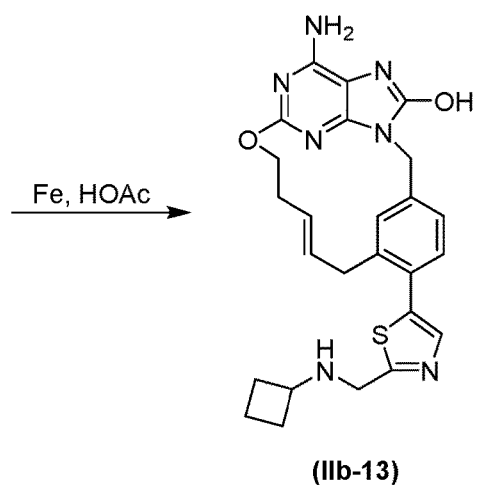

Example 5—Synthesis of Compounds According to FIG. 5

This example relates to the synthesis of compounds according to the scheme of FIG. 5, with compound (IIb-13) being used as an exemplar.

COMPOUND 45. A mixture of compound 29 (48 mg, 0.100 mmol), compound 44 (76 mg, 0.301 mmol), Pd(dppf)$Cl_2$ DCM complex (7.3 mg, 10.04 μmol) and KOAc (29.5 mg, 0.301 mmol) in DME (2 mL) was evacuated, back filled with nitrogen three times and then heated at 85° C. for 3 hours. The reaction mixture was diluted with EtOAc and washed with water and brine. The organic layer was dried over $MgSO_4$ and concentrated in vacuo. The crude product was purified by flash chromatography on silica gel using an automated ISCO system (24 g column, eluting with 5-50% EtOAc/hexanes) to give compound 45 (52 mg, 0.099 mmol, 99% yield) as a colorless oil. MS (ESI) m/z 526.2 (M+H).

COMPOUND 47. A mixture of compound 45 (39 mg, 0.074 mmol), 5-bromothiazole-2-carbaldehyde 46 (21.4 mg, 0.111 mmol), Pd(dppf)$Cl_2$ DCM complex (6.1 mg, 7.42 μmol) and $K_3PO_4$ (47.3 mg, 0.223 mmol) in 1,4-dioxane (2 mL) was evacuated, back filled with nitrogen three times and heated at 85° C. for 5 days. LCMS showed about 20% conversion. The reaction mixture was diluted with EtOAc and washed with water and brine. The organic layer was dried over $MgSO_4$ and concentrated in vacuo. The crude product was purified by flash chromatography on silica gel using an automated ISCO system (24 g column, eluting with 10-90% EtOAc/hexanes). Compound 47 (10 mg, 0.020 mmol, 26.4% yield) was obtained as a foaming solid. MS (ESI) m/z 511.2 (M+H).

COMPOUND 48. A solution of compound 47 (10 mg, 0.020 mmol) and cyclobutanamine 39 (1.8 mg, 0.025 mmol) in DCM (0.5 mL)/MeOH (0.5 mL) was stirred at RT overnight. $NaBH_4$ (1.1 mg, 0.029 mmol) was added and the reaction mixture was stirred at RT for 10 min. The reaction mixture was diluted with EtOAc and washed with water and brine. The organic layer was dried over $MgSO_4$ and concentrated in vacuo. The crude product was purified by flash chromatography on silica gel using an automated ISCO system (12 g gold column, eluting with 1-6% 2 N $NH_3$ in MeOH/DCM). Compound 48 (9 mg, 0.016 mmol, 81% yield) was obtained as a foaming solid. MS (ESI) m/z 566.2 (M+H).

COMPOUND IIb-13. A mixture of compound 48 (9 mg, 0.016 mmol) and iron (7.1 mg, 0.127 mmol) in acetic acid (0.66 mL)/water (0.13 mL) was heated at 85° C. for 45 min. Solvent was evaporated in vacuo and the residue was suspended in 25% MeOH/DCM and filtered. The filtrate was concentrated and the crude product was dissolved in 25% MeOH/DCM and absorbed onto silica, purified by flash chromatography on silica gel using an automated ISCO system (12 g gold column, eluting with 2-16% 2 N $NH_3$ in MeOH/DCM) to afford compound IIb-13 (2.3 mg, 4.37 μmol, 27.4% yield) as a white solid. MS (ESI) m/z 490.2 (M+H); $^1$H NMR (500 MHz, methanol-$d_4$) δ 8.29 (s, 1H), 7.55 (s, 2H), 7.31-7.21 (m, 2H), 5.76-5.65 (m, 1H), 5.53 (dt, J=15.3, 7.5 Hz, 1H), 4.97 (s, 2H), 4.81 (br s, 2H), 4.14 (s, 1H), 4.04 (s, 1H), 3.41 (quin, J=7.7 Hz, 1H), 3.35 (s, 1H), 3.27 (br d, J=6.7 Hz, 2H), 2.49 (br d, J=5.2 Hz, 2H), 2.27-2.16 (m, 2H), 2.11-1.97 (m, 1H), 1.97-1.54 (m, 5H).

Figure 6:
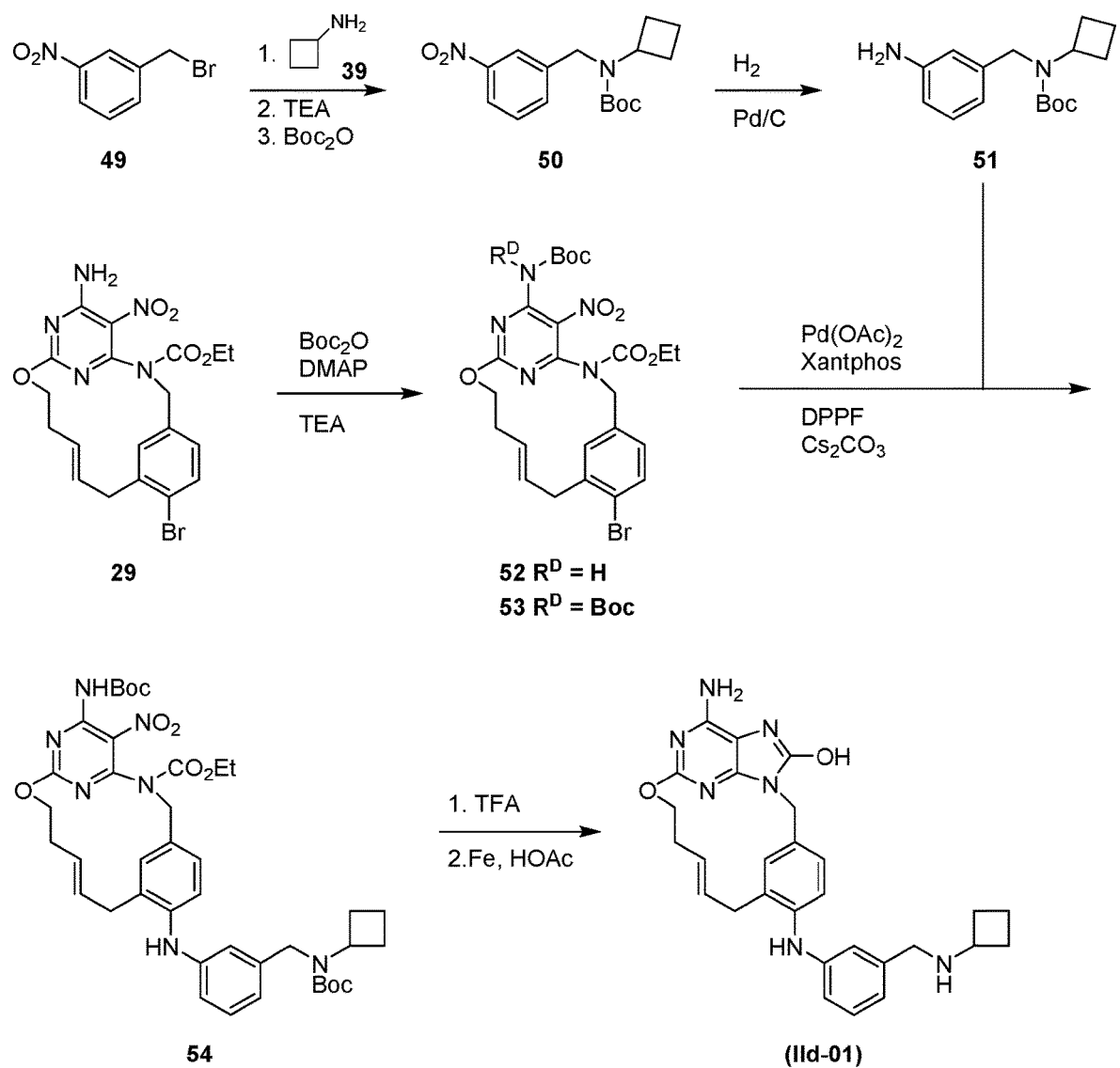

Example 6—Synthesis of Compounds According to FIG. 6

This example relates to the synthesis of compounds according to the scheme of FIG. 6, with compound (IId-01) being used as an exemplar.

COMPOUND 50. Compound 49 (1.080 g, 5 mmol) in DCM (2 mL) was added to a solution of cyclobutanamine 39 (0.356 g, 5.00 mmol) and TEA (1.0 mL, 7.50 mmol) in DCM (15 mL) at RT. The reaction mixture was stirred at RT for 24 h. Boc-anhydride (1.31 g, 6.00 mmol) was added to the reaction mixture and the reaction mixture was stirred at RT for 2 h. Solvent was evaporated in vacuo. The crude product was purified by flash chromatography on silica gel using an automated ISCO system (80 g column, eluting with 0-30% EtOAc/hexanes). Compound 50 (0.867 g, 2.83 mmol, 56.6% yield) was obtained as a light yellow oil. $^1$H NMR (400 MHz, CHLOROFORM-d) δ 8.19-8.02 (m, 2H), 7.58-7.41 (m, 2H), 4.57 (s, 2H), 2.22-2.10 (m, 2H), 2.10-1.97 (m, 2H), 1.67-1.59 (m, 3H), 1.44 (br s, 9H).

COMPOUND 51 A mixture of compound 50 (0.87 g, 2.84 mmol) and Pd—C (0.30 g, 0.284 mmol) in EtOAc (30 mL) was hydrogenated at 50 psi for 3 hours. The reaction mixture was filtered through CELITE™ and the filtrate was concentrated in vacuo to give crude compound 51 (0.75 g, 2.71 mmol, 96% yield) as an oil. The crude product was purified by flash chromatography on silica gel using an automated ISCO system (80 g column, eluting with 5-60% MeOH/DCM). Compound 51 (0.69 g, 2.497 mmol, 88% yield) was obtained as a colorless oil. MS (ESI) m/z 277.4 (M+H); $^1$H NMR (400 MHz, chloroform-d) δ 7.10 (t, J=7.8 Hz, 1H), 6.63-6.50 (m, 3H), 4.40 (s, 2H), 3.90-3.26 (m, 2H), 2.15-2.03 (m, 4H), 1.67-1.51 (m, 3H), 1.44 (br s, 9H).

COMPOUNDS 52 & 53. A solution of compound 29 (98 mg, 0.205 mmol), Boc-anhydride (59.1 mg, 0.27 mmol), DMAP (2.503 mg, 0.020 mmol) and TEA (42.8 μL, 0.307 mmol) in DCM (4 mL) was stirred at RT overnight. The solvent was evaporated in vacuo and the crude product was purified by flash chromatography on silica gel using an automated ISCO system (40 g gold column, eluting with 5-35% EtOAc/hexanes) to afford compounds 52 (86 mg, 73%, MS (ESI) m/z 578.2 (M+H)) and 53 (20 mg, 14%, MS (ESI) m/z 678.1 (M+H)).

COMPOUND 54. Compound 53 (20 mg, 0.029 mmol), compound 51 (10.6 mg, 0.038 mmol), palladium(II) acetate (2.0 mg, 8.84 μmol), bis(diphenylphosphino)ferrocene (1.6 mg, 2.95 μmol), xantphos (1.7 mg, 2.95 μmol) and $Cs_2CO_3$ (19 mg, 0.059 mmol) were combined in 1,4-dioxane (1.5 mL). The reaction mixture was evacuated, back filled with nitrogen three times, heated at 100° C. overnight. The reaction mixture was diluted with EtOAc and washed with water and brine. The organic layer was dried over $MgSO_4$ and concentrated in vacuo. The crude product was purified by flash chromatography on silica gel using an automated ISCO system (24 g gold column, eluting with 5-60% EtOAc/hexanes). Compound 54 (5.3 mg, 6.85 μmol, 23.23% yield) was obtained. MS (ESI) m/z 774.7 (M+H).

COMPOUND IId-01. Compound 54 was treated with TFA to remove Boc group, followed by the same sequence as used for converting compound 36 to compound IIb-01 above, to yield compound IId-01. MS (ESI) m/z 498.4 (M+H); $^1$H NMR (500 MHz, DMSO-$d_6$) δ 8.13 (s, 1H), 7.35 (s, 1H), 7.13-7.00 (m, 3H), 6.87 (s, 1H), 6.75-6.66 (m, 2H), 6.57 (br s, 2H), 5.76-5.64 (m, 1H), 5.51-5.41 (m, 1H), 4.83-4.67 (m, 4H), 3.14-3.06 (m, 2H), 2.47-2.40 (m, 2H), 2.09-1.99 (m, 2H), 1.81 (br s, 2H), 1.70-1.56 (m, 3H), 1.55-1.46 (m, 1H).

Figure 7:
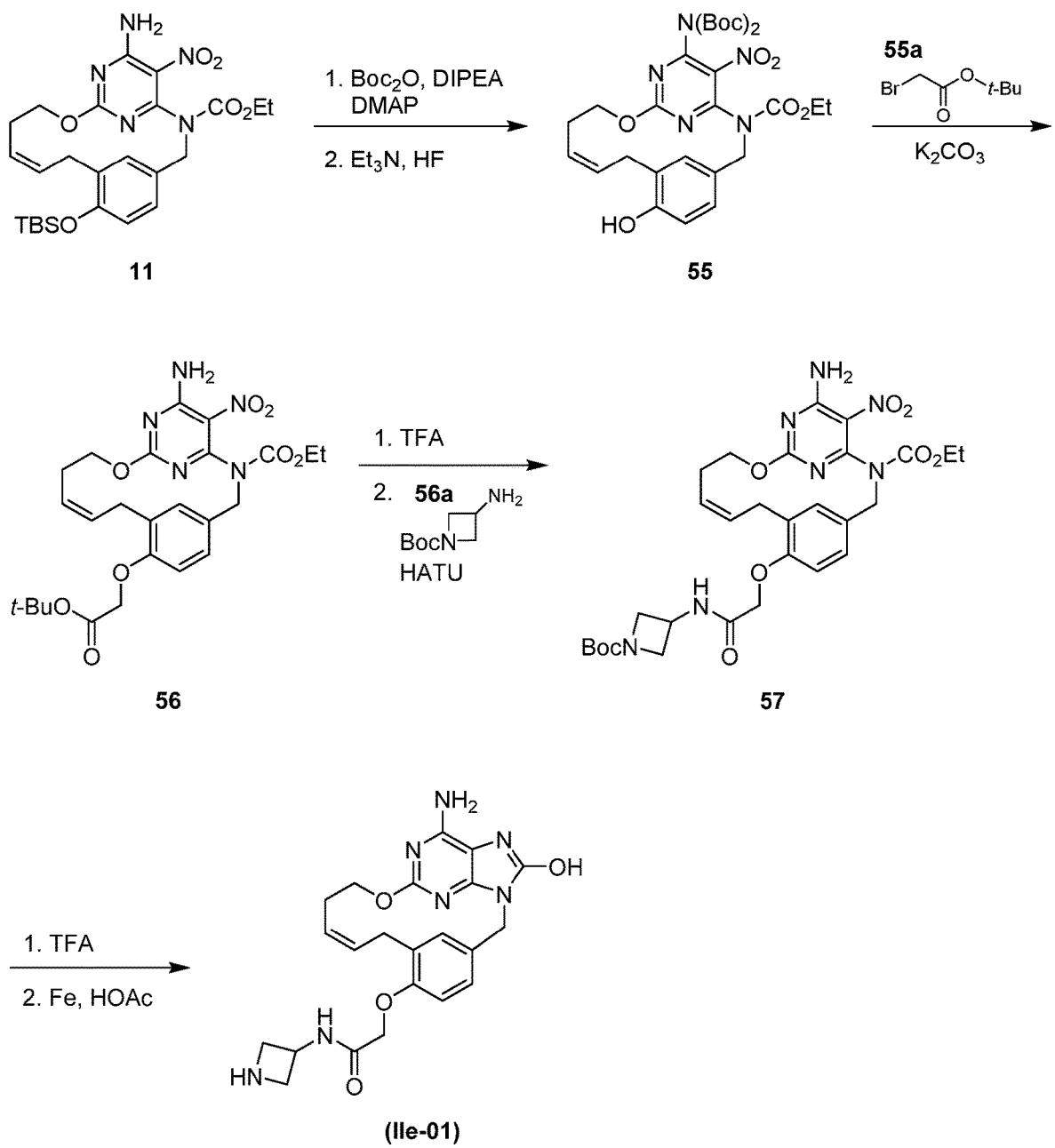

Example 7—Synthesis of Compounds According to FIG. 7

This example relates to the synthesis of compounds according to the scheme of FIG. 7, with compound (IIe-01) being used as an exemplar.

COMPOUND 55. A solution of compound 11 (200 mg, 0.318 mmol), Boc-anhydride (180 mg, 0.620 mmol), DIPEA (120 mg, 0.95 mmol) and DMAP (8 mg, 0.09 mmol) in DCM (2 mL) was stirred at RT for 16 hours. The reaction mixture was concentrated in vacuo. The crude mixture was purified using ISCO silica gel (12 g column, eluting with 0-50% EtOAc/hexane) to obtain an unisolated intermediate (232 mg, 0.26 mmol, 70% yield) as colorless foaming solid which was carried to the next step. MS (ESI) m/z 730.5 (M+H).

Triethylamine trihydrofluoride (558 μl, 3.43 mmol) was added to the solution of above intermediate (500 mg, 0.685 mmol) and TEA (477 μl, 3.43 mmol) in acetonitrile (7 mL). The reaction was stirred at RT for 2 hours. The reaction was concentrated in vacuo and the crude product was purified with ISCO silica gel (40 g column, eluting with 0-100% EtOAc/DCM) to give compound 55 (400 mg, 0.650 mmol, 95% yield). MS (ESI) m/z 616.08 (M+H).

COMPOUND 56. A mixture of compound 55 (100 mg, 0.162 mmol), $K_2CO_3$ (45 mg, 0.324 mmol) and tert-butyl 2-bromoacetate 55a (63 mg, 0.324 mmol) in acetonitrile (3 mL) was stirred at RT for 16 hours. The reaction was diluted with EtOAc-water (10:2 mL). The organic layer was washed with water, dried over $Na_2SO_4$, and concentrated in vacuo. The crude product was purified by ISCO silica gel (12 g gold column, eluting with 0-45% EtOAc/hexanes). Compound 56 (80 mg, 0.1 mmol, 62.1% yield) obtained. MS (ESI) m/z 730.3 (M+H).

COMPOUND 57. A mixture of compound 56 (30 mg, 0.041 mmol) and TFA (46.9 mg, 0.411 mmol) in DCM (1 mL) was stirred at RT for 1 hour. The reaction mixture was concentrated and kept under vacuum for 16 hours and the crude intermediate was taken as such to the next step. MS (ESI) m/z 474.1 (M+H).

The crude intermediate was dissolved in DMF (0.5 mL). To this solution DIPEA (0.046 mL, 0.247 mmol), tert-butyl 3-aminoazetidine-1-carboxylate 56a (10.62 mg, 0.062 mmol) and HATU (46.9 mg, 0.123 mmol). The reaction mixture was stirred for 6 hrs at RT. The reaction was diluted with EtOAc-water (5:1 mL). The organic layer was washed with water, dried and concentrated. The crude product was purified using ISCO column (4 g, 20-100% hexane-EtOAc) to yield compound 57 (22 mg, 0.032 mmol, 77% yield). MS (ESI) m/z 628.3 (M+H).

COMPOUND IIe-01. A mixture of compound 57 (38 mg, 0.061 mmol) and TFA (69.0 mg, 0.605 mmol) in DCM (1 mL) was stirred at RT for 1 hour. The reaction was concentrated and the residue was dried under vacuum for 4 hours. The residue was taken up in acetic acid (0.8 mL) and water (0.2 mL) mixture and to which was added iron (33.8 mg, 0.605 mmol). The reaction was heated at 85° C. for 45 min. The reaction was allowed to cool to RT and diluted with 1 mL DMF. The mixture was filtered through a syringe filter and the filtrate was subjected to preparative LCMS using these conditions as below: Column: XBridge C18, 200 mm×19 mm, 5-μm particles; Mobile Phase A: 5:95 acetonitrile:water with 10-mM $NH_4OAc$; Mobile Phase B: 95:5 acetonitrile:water with 10-Mm $NH_4OAc$; Gradient: a 0-min hold at 1% B, 1-41% B over 30 minutes, then a 4-min hold at 100% B; Flow Rate: 20 mL/min; Column Temperature: 25 C. Fraction collection was triggered by MS signals. Fractions containing the desired product were combined and dried via centrifugal evaporation to furnish compound IIe-01 (6.4 mg, 0.014 mmol, 22.55% yield). MS (ESI) m/z 452.02 (M+H). $^1$H NMR (500 MHz, DMSO-$d_6$) δ 10.52 (br s, 1H), 7.81 (s, 1H), 7.41 (br d, J=7.5 Hz, 2H), 7.26 (br d, J=7.5 Hz, 3H), 7.21 (d, J=7.6 Hz, 1H), 6.65 (br s, 1H), 5.8-5.61 (m, 1H), 5.56-5.48 (m, 1H), 4.58 (m, 2H), 4.51 (s, 2H), 3.94 (m, 1H), 3.45 (br d, J=7.0 Hz, 2H), 3.30 (m, 2H), 3.14 (br d, J=7.0 Hz, 2H), 2.80 (m, 2H).

Compound IIe-02 was analogously prepared mutatis mutandis. MS (ESI) m/z 452.1 (M+H). $^1$H NMR (500 MHz, DMSO-$d_6$) δ 10.4 (br s, 1H), 7.74 (s, 1H), 7.49 (br d, J=7.5 Hz, 2H), 7.32 (br d, J=7.5 Hz, 3H), 7.24 (d, J=7.6 Hz, 1H), 6.68 (br s, 1H), 5.6 (m, 1H), 5.4 (m, 1H), 4.58 (m, 2H), 4.45 (s, 2H), 3.83 (m, 1H), 3.45 (br d, J=7.0 Hz, 2H), 3.30 (m, 2H), 3.14 (br d, J=7.0 Hz, 2H), 2.76 (m, 2H).

Figure 8:
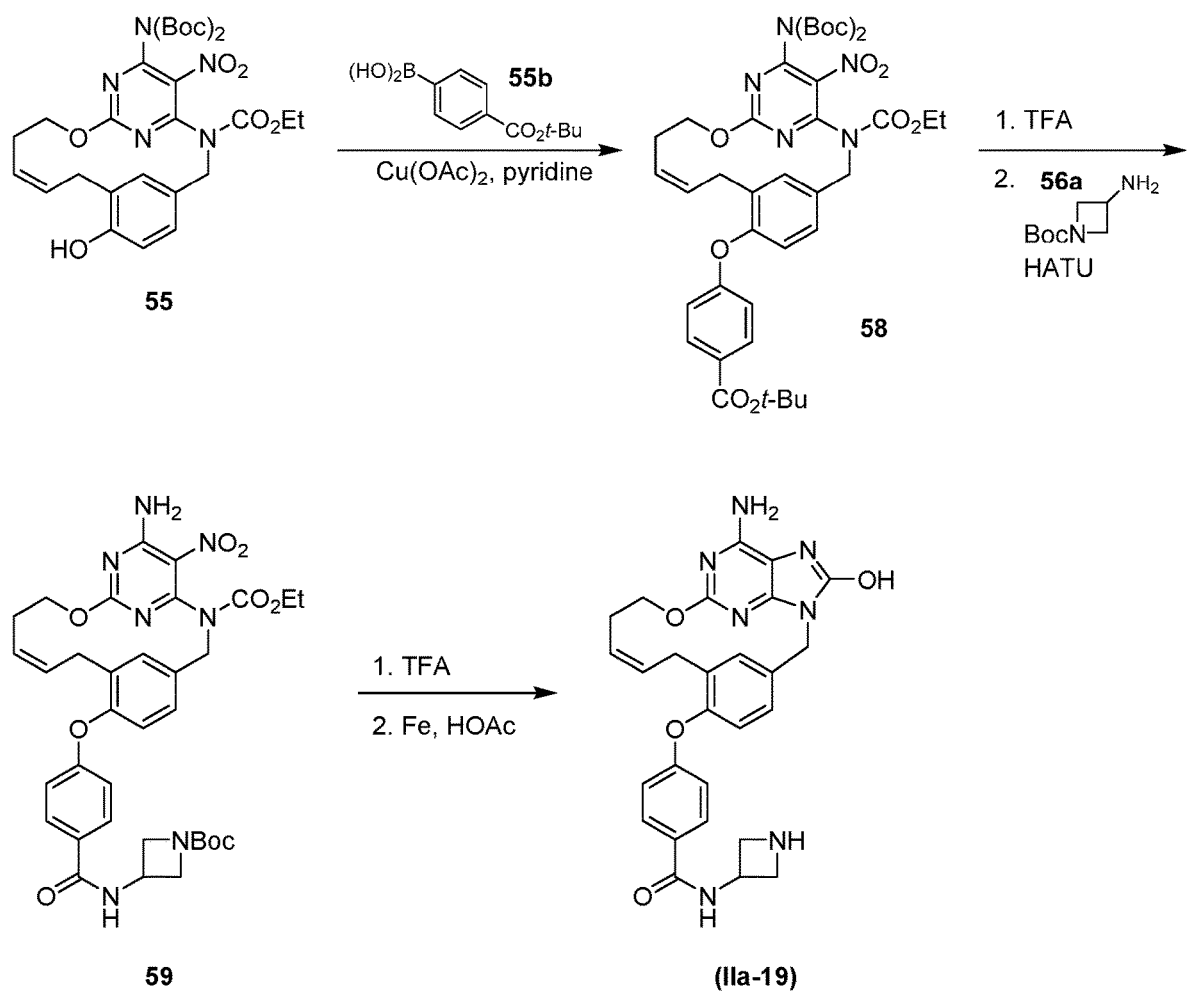

Example 8—Synthesis of Compounds According to FIG. 8

This example relates to the synthesis of compounds according to the scheme of FIG. 8, with compound (IIa-19) being used as an exemplar.

COMPOUND 58. A mixture of compound 55 (82 mg, 0.133 mmol), (4-(tert-butoxycarbonyl)phenyl)boronic acid 55b (89 mg, 0.400 mmol), copper (II) acetate (36.3 mg, 0.200 mmol), pyridine (53.9 μl, 0.666 mmol) and molecular sieves (4 A, 150 mg) in DCM (1332 μL) was stirred at 35° C. overnight. CELITE™ was added and the reaction mixture was filtered. The filtrate was concentrated and the crude product was purified by ISCO silica gel (40 g gold column, eluting with 10-35% EtOAc/hexanes) to give compound 58 (76 mg, 0.086 mmol, 65.1% yield) as a yellow solid. MS (ESI) m/z 792.3 (M+H).

COMPOUND 59. A mixture of compound 58 (85 mg, 0.10 mmol) and TFA (46.9 mg, 0.411 mmol) in DCM (1 mL) was stirred at RT for 1 hour. The reaction mixture was concentrated and kept under vacuum for 16 hours and the crude intermediate was taken as such to the next step. MS (ESI) m/z 592.1 (M+H).

The crude intermediate was dissolved in DMF (0.5 mL). To this was added DIPEA (0.12 mL, 0.66 mmol), compound 56a (28 mg, 0.16 mmol) and HATU (122 mg, 0.32 mmol). The reaction mixture was stirred for 6 hrs at RT. The reaction mixture was diluted with EtOAc-water (5:1 mL). The organic layer was washed with water, dried and concentrated. The crude product was purified using ISCO column (4 g, 20-100% hexane-EtOAc) to give compound 59 (40 mg, 0.052 mmol, 48.6% yield). MS (ESI) m/z 690.3 (M+H).

COMPOUND IIa-19. A mixture of compound 59 (40 mg, 0.058 mmol) and TFA (66 mg, 0.58 mmol) in DCM (1 mL) was stirred at RT for 1 hour. The reaction mixture was concentrated. The residue was dried under vacuum for 16 h and then taken up in an HOAc (0.8 mL)-water (0.2 mL) mixture and to which was added iron (32.5 mg, 0.58 mmol). The reaction mixture was heated at 85° C. for 45 min, allowed to cool to room temperature, and diluted with 1 mL DMF. The reaction mixture was filtered through a syringe filter and the filtrate was subjected to preparative LCMS using conditions following: Column: XBridge C18, 200 mm×19 mm, 5-m particles; Mobile Phase A: 5:95 acetonitrile:water with 10-mM $NH_4OAc$; Mobile Phase B: 95:5 acetonitrile:water with 10-Mm $NH_4OAc$; Gradient: a 0-min hold at 7% B, 7-45% B over 25 minutes, then a 6-min hold at 100% B; Flow Rate: 20 mL/min; Column Temperature: 25 C. Fraction collection was triggered by MS signals. Fractions containing the desired product were combined and dried via centrifugal evaporation to give 8.9 mg (0.015 mmol, 25.5% yield) of compound IIa-19. MS (ESI) m/z 514.26 (M+H). 1H NMR (500 MHz, DMSO-d6) δ 8.24 (s, 1H), 7.26 (br d, J=8.2 Hz, 2H), 7.14 (br d, J=7.9 Hz, 1H), 6.81 (br d, J=8.2 Hz, 2H), 6.71 (d, J=7.9 Hz, 1H), 6.43 (br s, 2H), 5.71-5.57 (m, 1H), 5.53-5.39 (m, 1H), 4.81 (s, 2H), 4.70 (br s, 2H), 3.57 (s, 1H), 3.11 (br d, J=7.0 Hz, 2H), 2.40 (br s, 2H), 2.04 (br d, J=7.6 Hz, 2H), 1.78-1.46 (m, 4H).

Compound IIa-20 was analogously prepared, mutatis mutandis. MS (ESI) m/z 514.26 (M+H).

Figure 9:
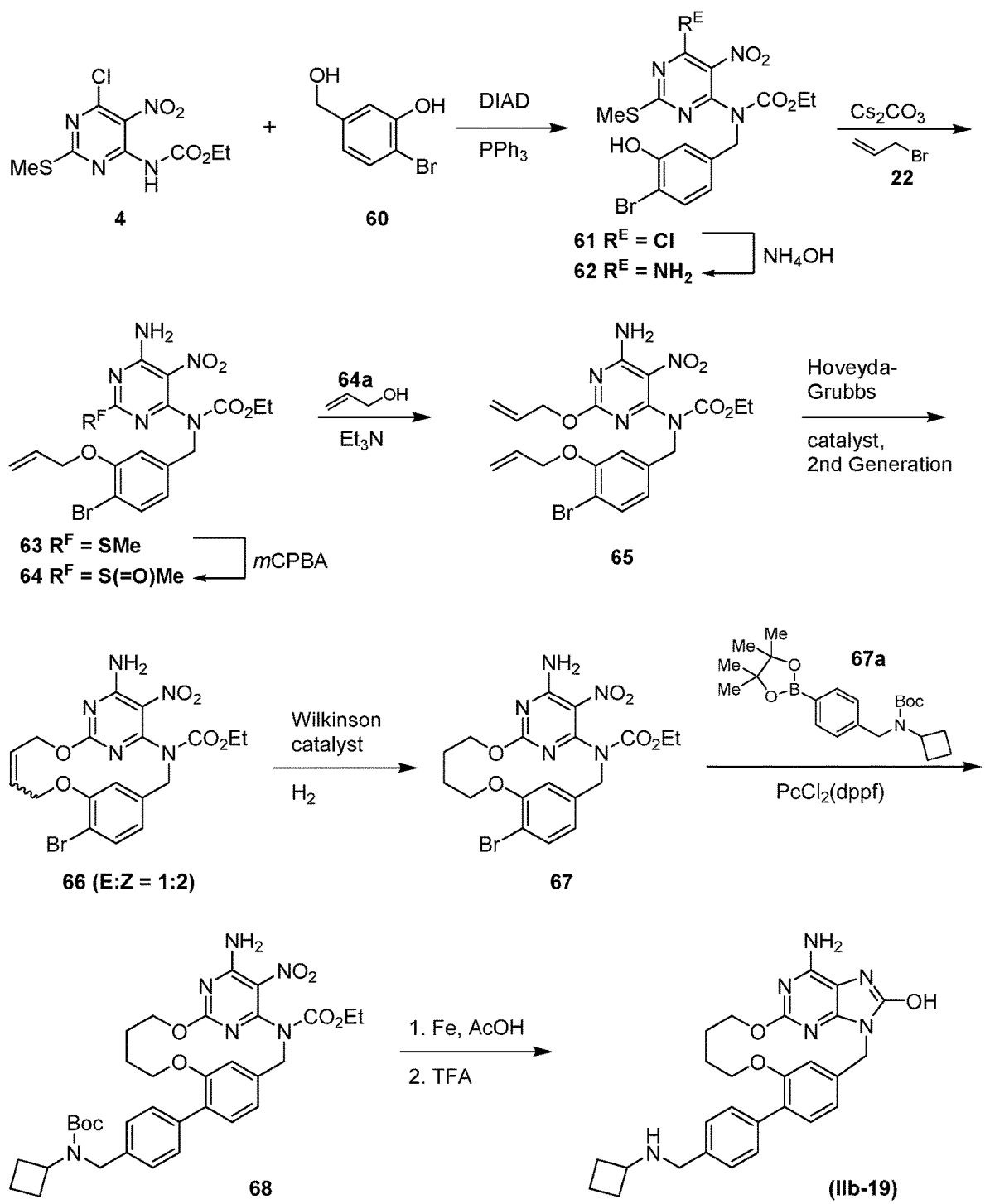

Example 9—Synthesis of Compounds According to FIG. 9

This example relates to the synthesis of compounds according to FIG. 9, with compound (IIb-19) being used as an exemplar.

COMPOUND 61. DIAD (1.049 mL, 5.12 mmol) was added to a solution of compound 4 (1 g, 3.42 mmol) and triphenylphosphine ($PPh_3$, 1.344 g, 5.12 mmol) in THF (17.08 mL) at 0 C. Compound 60 (1.041 g, 5.12 mmol) was added and allowed to stir at RT for 4 h. The solvent was evaporated in vacuo. The crude product was purified by flash chromatography on silica gel using an automated ISCO system (120 gold column. 25% EtOAc/hexanes) to afford compound 61 (0.713 g, 1.493 mmol, 43.7% yield) as thick oil. MS (ESI) m/z 479.1 (M+H).

COMPOUND 62. Ammonia in water (4.03 mL, 55.9 mmol) was added to a solution of compound 61 (0.534 g, 1.118 mmol) in THF (11.18 mL) and the reaction mixture was stirred at RT for 2 h. The reaction mixture was concentrated in vacuo to give crude compound 62 (0.512 g, 1.118 mmol, 100% yield) as a yellow solid which was used without further purification. MS (ESI) m/z 460.2 (M+H).

COMPOUND 63. To a solution of compound 62 (300 mg, 0.655 mmol) in DMF (6 mL) was added $Cs_2CO_3$ (640 mg, 1.964 mmol) followed by 3-bromoprop-1-ene 22 (0.277 mL, 3.27 mmol). The reaction mixture was stirred at RT overnight, diluted with EtOAc, washed with brine, dried over $Na_2SO_4$, and concentrated. The crude was purified using an ISCO silica gel (24 g column, eluting with 2% MeOH/DCM) to afford compound 63 (255 mg, 0.512 mmol, 78% yield) as thick pale yellow oil. MS (ESI) m/z 500.1 (M+H).

COMPOUND 64. mCPBA (116 mg, 0.512 mmol) was added to a solution of compound 63 (255 mg, 0.512 mmol) in DCM (10 mL) at 0° C. and the reaction mixture was stirred at RT for 2 h. LCMS showed completion of the reaction. Sodium thiosulfate (162 mg, 1.023 mmol) in water (20 mL) was added to the reaction mixture. The layers were separated and the aqueous layer was extracted with DCM (2×20 mL). The organic layer was dried over $MgSO_4$ and concentrated. The crude product was purified using a Combiflash (24 g column, eluting with 5% MeOH/DCM) to furnish compound 64 (214 mg, 0.416 mmol, 81% yield). MS (ESI) m/z 516.1 (M+H).

COMPOUND 65. To a solution of compound 64 (2 g, 3.89 mmol) and allyl alcohol 64a (10.58 mL, 156 mmol) was added TEA (2.168 mL, 15.55 mmol). The solution was then stirred at RT overnight. The reaction mixture was diluted with EtOAc (200 mL) and washed with water (2×200 mL) and brine (100 mL). The organic layer was dried, concentrated and purified using Combiflash (40 g column, eluting with. 50% EtOAc/hexane) to afford compound 65 (1.42 g, 2.79 mmol, 71.8% yield) as an oil. MS (ESI) m/z 510.1 (M+H). 1H NMR (400 MHz, DMSO-d6) δ 8.47 (s, 1H), 7.97 (s, 1H), 7.52 (d, J=8.1 Hz, 1H), 7.16 (d, J=1.9 Hz, 1H), 6.91 (dd, J=8.2, 1.9 Hz, 1H), 6.00 (dddt, J=17.2, 13.7, 10.6, 5.2 Hz, 2H), 5.36 (ddq, J=28.8, 17.3, 1.7 Hz, 2H), 5.24 (ddq, J=10.5, 7.3, 1.5 Hz, 2H), 5.06 (s, 2H), 4.76 (dt, J=5.5, 1.5 Hz, 2H), 4.59 (dt, J=5.0, 1.6 Hz, 2H), 4.06 (q, J=7.1 Hz, 2H), 1.10 (t, J=7.1 Hz, 3H).

COMPOUND 66. To a solution of compound 65 (112 mg, 0.220 mmol) in DCE (48 mL) was added 1,3-dimesitylimidazolidin-2-ylidene)(2-isopropoxybenzylidene)ruthenium (VI) chloride (Hoveyda Grubbs catalyst, second generation, 4.14 mg, 6.61 μmol) and the reaction mixture was heated at 80° C. for 4 h in a sealed pressure flask. Imidazole (90 mg, 1.322 mmol) was added and heated at 80° C. for 1 h. The reaction mixture was cooled to RT, washed with 1N HCl followed by water. The organic layer was dried and concentrated. The crude product was purified using Combiflash (24 g column, eluting with 45% EtOAc/hexane) to give E-isomer of compound 66 (25 mg, 0.052 mmol, 23.63% yield). MS (ESI) m/z 480.1 (M+H). 1H NMR (400 MHz, DMSO-d6) δ 8.46 (s, 1H), 7.89 (s, 1H), 7.46 (d, J=8.1 Hz, 1H), 7.22 (d, J=2.0 Hz, 1H), 6.91 (dd, J=8.1, 1.9 Hz, 1H), 5.91 (d, J=16.1 Hz, 1H), 5.58-5.30 (m, 1H), 4.99-4.74 (m, 4H), 4.72 (s, 2H), 4.04 (q, J=7.0 Hz, 2H), 1.09 (t, J=7.1 Hz, 3H). 45% EtOAc/hexane fractions collected at 18 min were concentrated to provide Z-isomer of compound 66 (44 mg, 0.092 mmol, 41.6% yield). MS (ESI) m/z 480.1 (M+H). 1H NMR (400 MHz, DMSO-$d_6$) δ 8.48 (s, 1H), 7.87 (s, 1H), 7.50 (d, J=7.9 Hz, 1H), 6.97 (dd, J=8.1, 1.7 Hz, 1H), 5.70 (dt, J=10.4, 4.9 Hz, 1H), 5.56 (dt, J=11.5, 7.0 Hz, 1H), 5.25 (brs, 2H), 4.79 (d, J=7.1 Hz, 2H), 4.69 (s, 2H), 3.97 (brs, 2H), 1.07 (brs, 3H). An additional 13 mg of EZ mixture was also isolated. For the following step all the material was combined and taken forward.

COMPOUND 67. A compound 66 (300 mg, 0.625 mmol) and tris(triphenyl-phosphine)rhodium(I) chloride (Wilkinson's catalyst, 57.8 mg, 0.062 mmol) in THF/MeOH (1:1; 62 mL) was hydrogenated in Paar shaker at 5 bar pressure for 20 hours. The reaction was filtered over CELITE™ and the filtrate was concentrated. The crude product was purified using Combiflash (40 g column, eluting with 45% EtOAc/hexane) to give compound 67 (109 mg, 0.226 mmol, 36.2% yield) as white solid. MS (ESI) m/z 484.1 (M+H).

COMPOUND 68. A mixture of compound 67 (21 mg, 0.044 mmol), compound 67a (20.24 mg, 0.052 mmol), Pd(dppf)Cl$_2$-DCM adduct (3.56 mg, 4.35 µmol) and K$_3$PO$_4$ (27.7 mg, 0.131 mmol) in 1,4-dioxane (1089 µl) was stirred under nitrogen at 85° C. overnight. The reaction mixture was diluted with EtOAc and washed with water and brine. The organic layer was dried over MgSO$_4$ and concentrated in vacuo. The crude product was purified by flash chromatography on silica gel using an automated ISCO system (12 g column, eluting with 55% EtOAc/hexanes) to furnish compound 68 (19 mg, 0.029 mmol, 65.8% yield) as a foaming solid. MS (ESI) m/z 663.4 (M+H)

COMPOUND IIb-19. A mixture of compound 68 (38 mg, 0.057 mmol) and iron (19.21 mg, 0.344 mmol) in HOAc (956 µl)/water (191 µL) was heated at 100° C. overnight. LCMS showed a mixture of the desired product and Boc protected product. The solvent was evaporated in vacuo. The reaction mixture was suspended in 25% MeOH/DCM (5 mL) and the solid was filtered. The filtrate was concentrated and the crude was treated with 25% TFA in DCE (0.6 mL) at RT for 1 hour. The crude material was purified via preparative LC/MS with the following conditions: Column: XBridge C18, 200 mm×19 mm, 5-µm particles; Mobile Phase A: 5:95 acetonitrile:water with 0.1% TFA; Mobile Phase B: 95:5 acetonitrile:water with 0.1% TFA; Gradient: a 0-min hold at 4% B, 4-50% B over 30 min, then a 4-min hold at 100% B; Flow Rate: 20 mL/min; Column Temperature: 25 C. Fraction collection was triggered by MS signals. Fractions containing the desired product were combined and dried via centrifugal evaporation. 7.5 mg of compound IIb-19 was obtained. MS (ESI) m/z 487.12 (M+H). 1H NMR (500 MHz, DMSO-d6) δ 8.02 (s, 1H), 7.61-7.36 (m, 4H), 7.20 (d, J=7.6 Hz, 1H), 6.94 (d, J=7.7 Hz, 1H), 6.42 (s, 2H), 4.87 (s, 2H), 4.60 (s, 2H), 4.27 (s, 2H), 4.00 (s, 2H), 3.74-3.47 (m, 2H), 2.32-2.08 (m, 4H), 1.78 (dt, J=19.1, 9.4 Hz, 2H), 1.59 (s, 4H).

Figure 10:
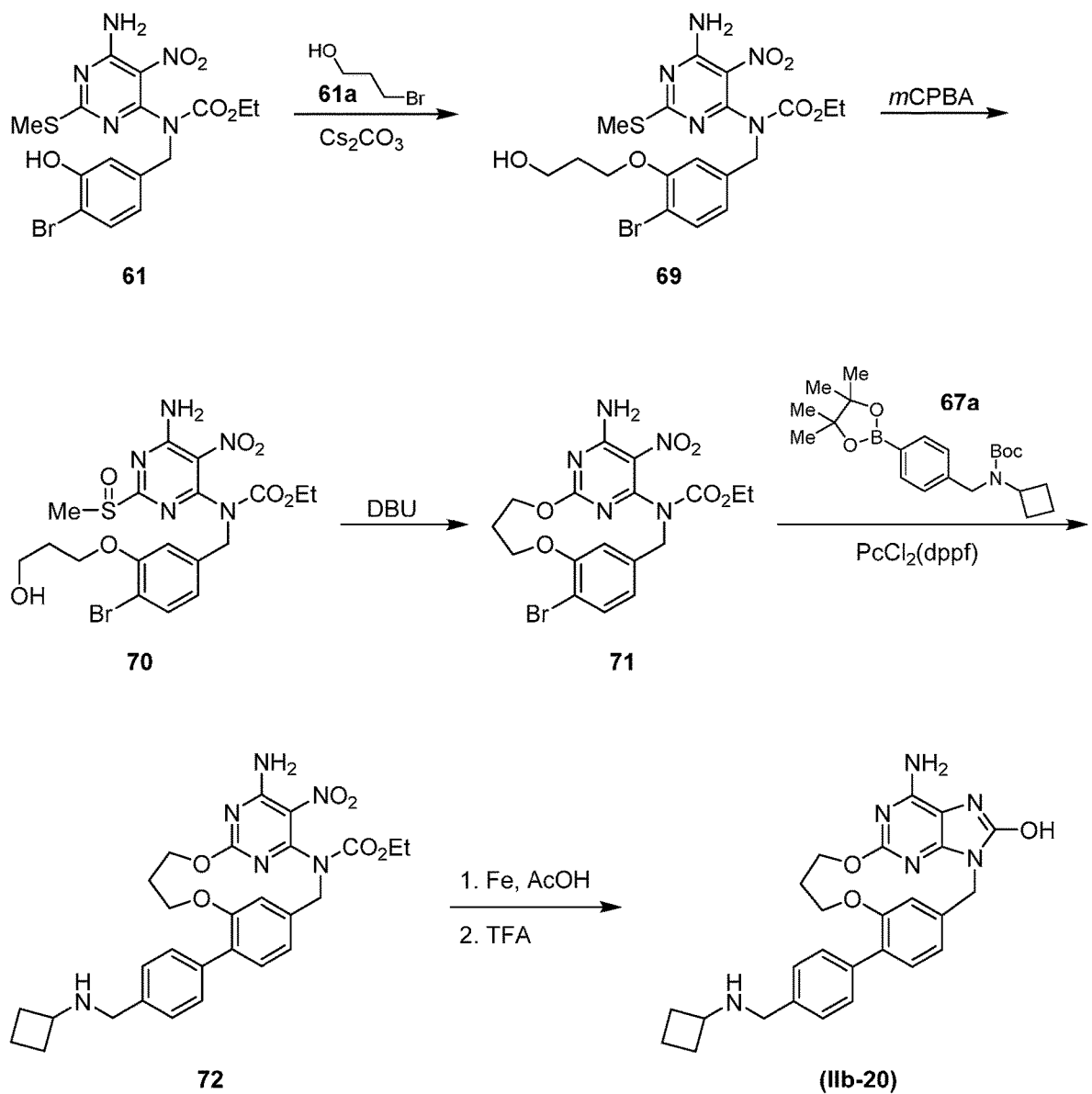

Example 10—Synthesis of Compounds According to FIG. 10

This example relates to the synthesis of compounds according to FIG. 10, with compound (IIb-20) being used as an exemplar.

COMPOUND 69: To a flask containing compound 61 (200 mg, 0.436 mmol) in DMF (4 mL) was added Cs$_2$CO$_3$ (427 mg, 1.309 mmol) followed by 3-bromopropan-1-ol 61a (0.191 mL, 2.182 mmol). The resulting mixture was stirred at RT overnight. The reaction mixture was diluted with EtOAc, washed with brine, dried, and concentrated. The crude product was purified using ISCO (40 g column, eluting with 4% MeOH/DCM) to afford compound 69 (155 mg, 0.301 mmol, 69% yield) as thick pale yellow oil. MS (ESI) m/z 518.1 (M+H).

COMPOUND 70. mCPBA (0.347 g, 1.549 mmol) was added to a solution of compound 69 (0.8 g, 1.549 mmol) in DCM (40 mL) at 0° C. The reaction mixture was stirred at RT for 2 hours. Sodium thiosulfate (0.490 g, 3.10 mmol) in water (10 mL) was added to the reaction mixture. The layers were separated and the aqueous layer was extracted with DCM (2×10 mL). The organic layer was dried over MgSO$_4$ and concentrated. The crude product was purified on Combiflash (40 g column, eluting with 5% MeOH/DCM) to afford compound 70 (0.343 g, 0.644 mmol, 41.6% yield). MS (ESI) m/z 534.1.

COMPOUND 71. To a solution of compound 70 (243 mg, 0.456 mmol) in 1,4-dioxane (45.6 mL), DBU (0.138 mL, 0.913 mmol) was added. The reaction mixture stirred at RT for 3 days. The reaction mixture was diluted with EtOAc (100 mL) and washed with water (3×50 mL). The organic layer was dried and concentrated. The crude product was purified using Combiflash (40 g column, eluting with 60% EtOAc/hexane) to give compound 71 (8 mg, 4% yield) as white solid. MS (ESI) m/z 470.1 (M+H).

COMPOUND 72. A mixture of compound 71 (2 mg, 4.27 µmol), compound 67a (1.985 mg, 5.13 µmol), Pd(dppf)Cl$_2$-DCM adduct (0.349 mg, 0.427 µmol) and K$_3$PO$_4$ (2.72 mg, 0.013 mmol) in 1,4-dioxane (107 µl) was stirred under nitrogen at 85° C. overnight. The reaction mixture was diluted with EtOAc and washed with water and brine. The organic layer was dried over MgSO$_4$ and concentrated in vacuo. The crude product was purified by ISCO system (4 g column, eluting with 55% EtOAc/hexane. Product containing fractions were concentrated to give compound 72 (2 mg, 3.08 µmol, 72.2% yield) as a foaming solid. MS (ESI) m/z 649.2 (M+H).

COMPOUND IIB-20. A mixture of compound 72 (2 mg, 3.08 µmol) and iron (1.033 mg, 0.018 mmol) in HOAc (257 µL)/Water (51.4 µL) was heated at 85° C. for 4 h. The reaction mixture was suspended in 25% MeOH/DCM and filtered. The filtrate was concentrated and purified via preparative LC/MS with the following conditions: Column: XBridge C18, 200 mm×19 mm, 5-µm particles; Mobile Phase A: 5:95 acetonitrile:water with 0.1% TFA; Mobile Phase B: 95:5 acetonitrile:water with 0.1% TFA; Gradient: a 0-min hold at 3% B, 3-43% B over 23 min, then a 4-min hold at 100% B; Flow Rate: 20 mL/min; Column Temperature: 25 C. 0.7 mg of compound IIb-20 was obtained. MS (ESI) m/z 473.07 (M+H).

Example 11—HEK-Blue™ TLR7 Reporter Assay

This example describes a method for assaying TLR7 agonist activity of the compounds disclosed in this specification.

Figure 14:
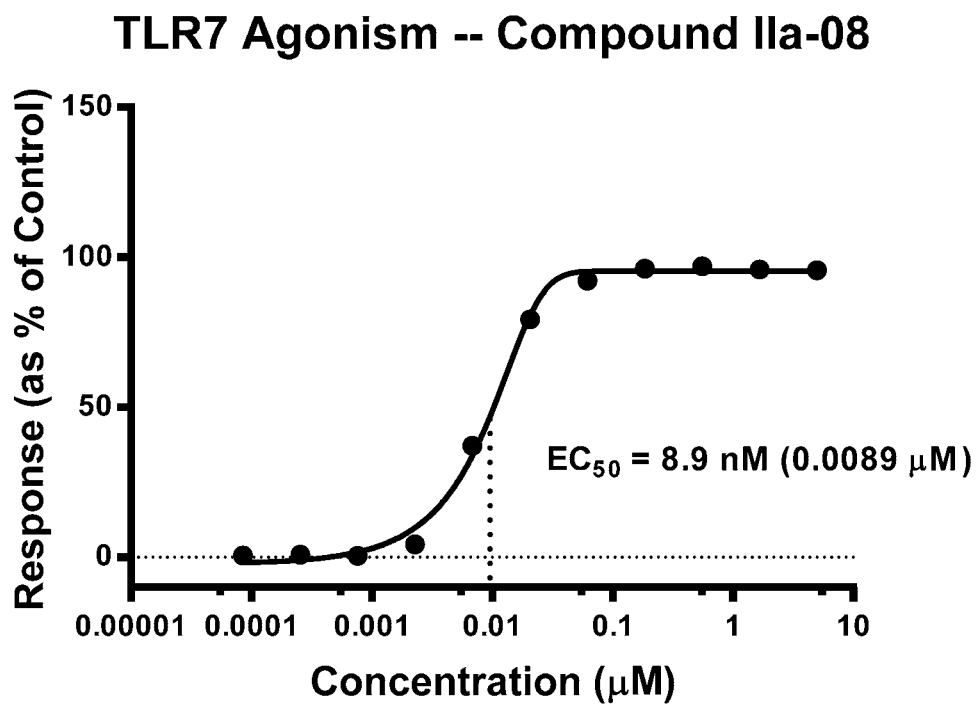
FIG. 14 is an exemplary plot of data used to determine TLR7 agonist efficacy of compounds disclosed herein.

Engineered human embryonic kidney blue cells (HEK-Blue™ TLR cells; Invivogen) possessing a human TLR7-secreted embryonic alkaline phosphatase (SEAP) reporter transgene were suspended in a non-selective, culture medium (DMEM high-glucose (Invitrogen), supplemented with 10% fetal bovine serum (Sigma)). HEK-Blue™ TLR7 cells were added to each well of a 384-well tissue-culture plate (15,000 cells per well) and incubated 16-18 h at 37° C., 5% CO$_2$. Compounds (100 nl) were dispensed into wells containing the HEK-Blue™ TLR cells and the treated cells were incubated at 37° C., 5% CO$_2$. After 18 h treatment ten microliters of freshly-prepared Quanti-Blue™ reagent (Invivogen) was added to each well, incubated for 30 min (37° C., 5% CO$_2$) and SEAP levels measured using an Envision plate reader (OD=620 nm). The half maximal effective concentration values (EC$_{50}$; compound concentration which induced a response halfway between the assay baseline and maximum) were calculated. EC$_{50}$'s can be determined with software such as Graphpad Prism™. An exemplary EC$_{50}$ plot, for compound (IIa-08), is shown in FIG. 14.

Example 12—Interleukin 6 Induction Assay

This example describes a method for assaying interleukin 6 (IL 6) induction by compounds disclosed in this specification.

Compounds suspended in DMSO were transferred to individual wells of a Matrix Technologies clear, V-bottom 384-well plate using ECHO acoustic liquid handling technology (25 nL per well). Human whole-blood samples (25 uL) were added to each well using a CyBio FeliX liquid handling instrument and the plate was shaken on a plate shaker for three minutes before incubating the reaction mixtures at 37° C. for 20 h. Basel RPMI 1640 medium (supplemented with L-glutamine) was then added to each well (25 uL per well) prior to liberating plasma from each sample by centrifugation (450×g, 5 min, ambient temperature). Treated plasma samples (3 uL) were subsequently transferred to individual wells of a white, shallow, 384-well ProxiPlate (PerkinElmer) using the FeliX liquid handling instrument and their IL6 levels were measured using AlphaLISA technology as described by the manufacturer (PerkinElmer). Software was used to determine compound $EC_{50}$ values where assay baselines were set using relative luminescence (RLU) values from DMSO-treated control cells, and 100% was set using resiquimod reference agonist RLU values from cells treated at the highest compound concentration, 10 uM.

Figure 15:
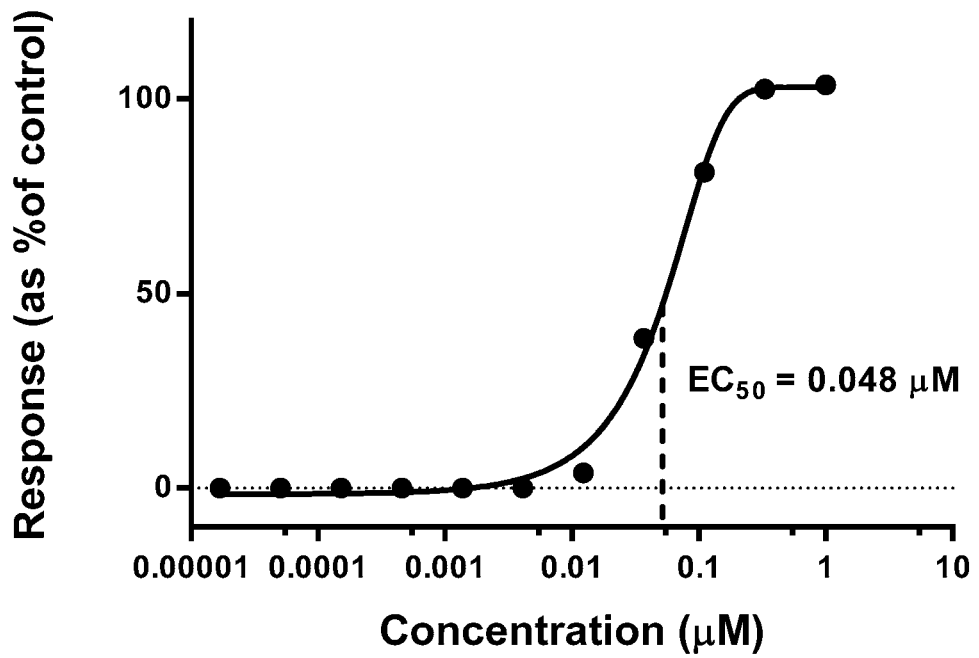
FIG. 15 is an exemplary plot of data used to determine interleukin 6 induction by compounds disclosed herein.

An exemplary $EC_{50}$ plot, for compound (IIa-03), is shown in FIG. 15, derived using GraphPad PRISM™ software.

Example 13—Transglutaminase-Mediated Conjugation

The following procedure can be used for transglutaminase mediated conjugation of agonist-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody: enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5. The eluted fractions are neutralized with 1M Tris pH 9.0. The conjugate can be formulated in 20 mg/mL Sorbitol, 10 mg/mL Glycine, pH 5.0.

Those skilled in the art will understand that the conditions and methodologies in this example are illustrative and non-limiting and other conjugation methods can be employed. For example, conjugation of a maleimide-terminated compound-linker moiety by Michael addition can be effected as taught in Cheng et al., U.S. Pat. No. 8,394,922 B2 (2013) and Cong et al., U.S. Pat. No. 8,980,824 B2 (2013).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

ACRONYMS AND ABBREVIATIONS

This is a list of acronyms and abbreviations used in this specification, along with their meanings.

| ACRONYM OR ABBREVIATION | MEANING OR DEFINITION |
|---|---|
| Boc | t-Butyloxycarbonyl |
| DBU | 1,8-Diazabicyclo[5.4.0]undec-7-ene |
| DCM | Dichloromethane |
| DIAD | Diisopropyl azodicarboxylate |
| DIPEA, DIEA | N,N-diisopropylethylamine, also known as Hünig's base |
| DMA | N,N-Dimethylacetamide |
| DMAP | 4-(Dimethylamino)pyridine |
| DMF | N,N-dimethylformamide |
| Fmoc | Fluorenylmethyloxycarbonyl |
| HATU | Hexafluorophosphate Azabenzotriazole Tetramethyl Uronium; 1-[Bis(dimethylamino)-methylene]-1H-1,2,3-triazolo[4,5-b]pyridinium 3-oxide hexafluorophosphate |
| mCPBA | m-chloroperbenzoic acid |
| PEG | Poly(ethylene glycol) |
| RT | Room temperature, circa 25° C. |
| TBS | t-Butyldimethylsilyl group |
| TEA | Triethylamine |
| TFA | Trifluoroacetic acid |
| THF | Tetrahydrofuran |

REFERENCES

Full citations for the following references cited in abbreviated fashion by first author (or inventor) and date earlier in this specification are provided below. Each of these references is incorporated herein by reference for all purposes.

Akinbobuyi et al., *Tetrahedron Lett.* 2015, 56, 458, "Facile syntheses of functionalized toll-like receptor 7 agonists".
Akinbobuyi et al., *Bioorg. Med. Chem. Lett.* 2016, 26, 4246, "Synthesis and immunostimulatory activity of substituted TLR7 agonists."
Barberis et al., US 2012/0003298 A1 (2012).
Beesu et al., *J. Med. Chem.* 2017, 60, 2084, "Identification of High-Potency Human TLR8 and Dual TLR7/TLR8 Agonists in Pyrimidine-2,4-diamines."
Berghöfer et al., *J. Immunol.* 2007, 178, 4072, "Natural and Synthetic TLR7 Ligands Inhibit CpG-A- and CpG-C-Oligodeoxynucleotide-Induced IFN-α Production."
Bonfanti et al., US 2014/0323441 A1 (2015) [2015a].
Bonfanti et al., US 2015/0299221 A1 (2015) [2015b].
Bonfanti et al., US 2016/0304531 A1 (2016).
Carson et al., US 2013/0202629 A1 (2013).
Carson et al., U.S. Pat. No. 8,729,088 B2 (2014).
Carson et al., U.S. Pat. No. 9,050,376 B2 (2015).
Carson et al., US 2016/0199499 A1 (2016).
Chan et al., *Bioconjugate Chem.* 2009, 20, 1194, "Synthesis and Immunological Characterization of Toll-Like Receptor 7 Agonistic Conjugates."
Chan et al., *Bioconjugate Chem.* 2011, 22, 445, "Synthesis and Characterization of PEGylated Toll Like Receptor 7 Ligands."
Coe et al., U.S. Pat. No. 9,662,336 B2 (2017).
Cortez et al., US 2017/0121421 A1 (2017).
Cortez et al., U.S. Pat. No. 9,944,649 B2 (2018).
Dellaria et al., WO 2007/028129 A1 (2007).

Desai et al., U.S. Pat. No. 9,127,006 B2 (2015).
Ding et al., WO 2016/107536 A1 (2016).
Ding et al., US 2017/0273983 A1 (2017) [2017a].
Ding et al., WO 2017/076346 A1 (2017) [2017b].
Gadd et al., *Bioconjugate Chem.* 2015, 26, 1743, "Targeted Activation of Toll-Like Receptors: Conjugation of a Toll-Like Receptor 7 Agonist to a Monoclonal Antibody Maintains Antigen Binding and Specificity."
Graupe et al., U.S. Pat. No. 8,993,755 B2 (2015).
Embrechts et al., *J. Med. Chem.* 2018, 61, 6236, "2,4-Diaminoquinazolines as Dual Toll Like Receptor (TLR) 7/8 Modulators for the Treatment of Hepatitis B Virus."
Halcomb et al., U.S. Pat. No. 9,161,934 B2 (2015).
Hashimoto et al., US 2009/0118263 A1 (2009).
He et al., US 2019/0055246 A1 (2019) [2019a].
He et al., US 2019/0055247 A1 (2019) [2019b].
Hirota et al., U.S. Pat. No. 6,028,076 (2000).
Holldack et al., US 2012/0083473 A1 (2012).
Isobe et al., U.S. Pat. No. 6,376,501 B1 (2002).
Isobe et al., JP 2004137157 (2004).
Isobe et al., *J. Med. Chem.* 2006, 49 (6), 2088, "Synthesis and Biological Evaluation of Novel 9-Substituted-8-Hydroxyadenine Derivatives as Potent Interferon Inducers."
Isobe et al., U.S. Pat. No. 7,521,454 B2 (2009) [2009a].
Isobe et al., US 2009/0105212 A1 (2009) [2009b].
Isobe et al., US 2011/0028715 A1 (2011).
Isobe et al., U.S. Pat. No. 8,148,371 B2 (2012).
Jensen et al., WO 2015/036044 A1 (2015).
Jones et al., U.S. Pat. No. 7,691,877 B2 (2010).
Jones et al., US 2012/0302598 A1 (2012).
Kasibhatla et al., U.S. Pat. No. 7,241,890 B2 (2007).
Koga-Yamakawa et al., *Int. J. Cancer* 2013, 132 (3), 580, "Intratracheal and oral administration of SM-276001: A selective TLR7 agonist, leads to antitumor efficacy in primary and metastatic models of cancer."
Li et al., U.S. Pat. No. 9,902,730 B2 (2018).
Lioux et al., U.S. Pat. No. 9,295,732 B2 (2016).
Lund et al., *Proc. Nat'l Acad. Sci (USA)* 2004, 101 (15), 5598, "Recognition of single-stranded RNA viruses by Toll-like receptor 7."
Maj et al., U.S. Pat. No. 9,173,935 B2 (2015).
McGowan et al., US 2016/0168150 A1 (2016) [2016a].
McGowan et al., U.S. Pat. No. 9,499,549 B2 (2016) [2016b].
McGowan et al., *J. Med. Chem.* 2017, 60, 6137, "Identification and Optimization of Pyrrolo[3,2-d]pyrimidine Toll-like Receptor 7 (TLR7) Selective Agonists for the Treatment of Hepatitis B."
Musmuca et al., *J. Chem. Information & Modeling* 2009, 49 (7), 1777, "Small-Molecule Interferon Inducers. Toward the Comprehension of the Molecular Determinants through Ligand-Based Approaches."
Nakamura et al., *Bioorg. Med. Chem. Lett.* 2013, 13, 669, "Synthesis and evaluation of 8-oxoadenine derivatives as potent Toll-like receptor agonists with high water solubility."
Ogita et al., US 2007/0225303 A1 (2007).
Pilatte et al., WO 2017/216293 A1 (2017).
Poudel et al., US 2019/0055243 A1 (2019) [2019a].
Poudel et al., US 2019/0055245 A1 (2019) [2019b].
Pryde, U.S. Pat. No. 7,642,350 B2 (2010).
Vernejoul et al., US 2014/0141033 A1 (2014).
Young et al., US 2019/0055244 A1 (2019).
Yu et al., *PLoS One* 2013, 8 (3), e56514, "Toll-Like Receptor 7 Agonists: Chemical Feature Based Pharmacophore Identification and Molecular Docking Studies."
Zhang et al., *Immunity* 2016, 45, 737, "Structural Analysis Reveals that Toll-like Receptor 7 Is a Dual Receptor for Guanosine and Single-Stranded RNA."
Zhang et al., WO 2018/095426 A1 (2018)>
Zurawski et al., US 2012/0231023 A1 (2012).

What is claimed is:
1. A compound having a structure represented by formula (I)

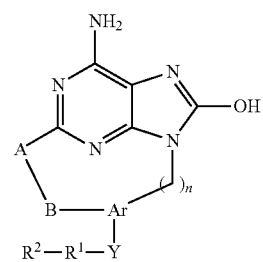

wherein
A is O, NH, N($C_1$-$C_3$ alkyl), or S;
B is a $C_1$-$C_{10}$ unsaturated or saturated alkyl, ($C_2$-$C_6$ alkyl)NHC(=O)($C_1$-$C_6$ alkyl), ($C_2$-$C_6$ alkyl)NHC(=O)($C_1$-$C_6$ alkyl)O, ($C_2$-$C_{10}$ unsaturated or saturated alkyl)O, ($C_2$-$C_6$ alkyl)O($C_2$-$C_6$ alkyl), ($C_2$-$C_6$ alkyl)O($C_2$-$C_6$ alkyl)O; each optionally substituted with $C_1$-$C_3$ alkyl or ($C_1$-$C_3$ alkyl)O;
Ar is a 6-membered aromatic, a 5- to 6-membered heteroaromatic, a 4- to 7-membered cycloaliphatic, or a 4- to 7-membered heterocycloaliphatic moiety;
Y is a bond, O, S, NH, N($C_1$-$C_3$ alkyl), $(CH_2)_{1-2}$, C(=O)NH, or C(=O)N($C_1$-$C_3$ alkyl);
$R^1$ is a 6-membered aromatic, a 5- to 6-membered heteroaromatic, a 4- to 7-membered cycloaliphatic, or a 4- to 7-membered heterocycloaliphatic moiety, or $R^1$ can be absent if Y is other than a bond;
$R^2$ is H, $C_1$-$C_3$ alkyl, halo, O($C_1$-$C_3$ alkyl), CN, $NO_2$, $(CH_2)_{1-4}R^3$,

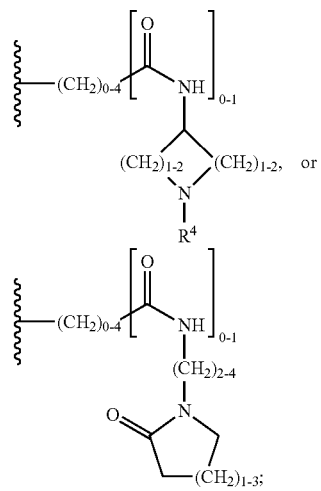

with the proviso that $R^2$ is other than halo, O($C_1$-$C_3$ alkyl), CN, or $NO_2$ when $R^1$ is absent;
$R^3$ is halo, OH, CN, $NH_2$, NH($C_1$-$C_5$ alkyl), NH($CH_2$)N($C_1$-$C_5$ alkyl)$_2$, NH($C_3$-$C_6$ cycloaliphatic), NH($C_4$-

C₈ bicycloaliphatic), NH(C₆-C₁₀ spirocycloaliphatic), N(C₃-C₆ cycloaliphatic)₂, NH(CH₂)₁₋₃(aryl), N((CH₂)₁₋₃(aryl))₂, NH(CH₂)₁₋₃CO₂(C₁-C₃ alkyl), N((CH₂)₁₋₃CO₂(C₁-C₃ alkyl))₂, or a cyclic amine moiety having the structure

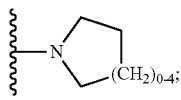

R⁴ is H, C₁-C₃ alkyl, or C(=O)(C₁-C₃ alkyl); and
n is 1, 2, or 3;
wherein
  an alkyl, cycloaliphatic, bicycloaliphatic, spirocycloaliphatic, cyclic amine, 6-membered aromatic or heteroaromatic, or 5-membered heteroaromatic moiety is optionally substituted with one or more substituents selected from OH, halo, CN, (C₁-C₃ alkyl), O(C₁-C₃ alkyl), C(=O)(C₁-C₃ alkyl), SO₂(C₁-C₃ alkyl), CO₂(C₁-C₃ alkyl), NH₂, NH(C₁-C₃ alkyl), and N(C₁-C₃ alkyl)₂;
  a cycloaliphatic, bicycloaliphatic, spirocycloaliphatic, or cyclic amine moiety may have a CH₂ group replaced by O, S, NH, C(=O), N(C₁-C₃ alkyl), NC(=O)(C₁-C₃ alkyl), or N(Boc); and
  a cycloaliphatic, heterocycloaliphatic, aromatic, or heteroaromatic moiety may be fused to another cycloaliphatic, heterocycloaliphatic, aromatic, or heteroaromatic moiety.

2. A compound according to claim 1, wherein -A-B— is

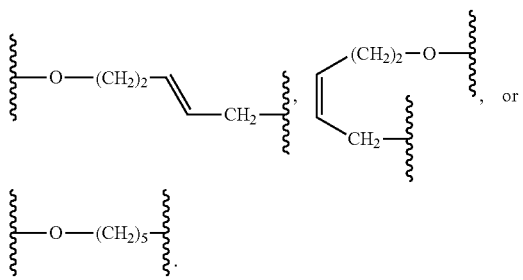

3. A compound according to claim 1 wherein Y is O, NH, or a bond and n is 1.

4. A compound according to claim 1, wherein R¹ is not absent and R² is (CH₂)₁₋₂NHR³, where R³ is OH, Cl,

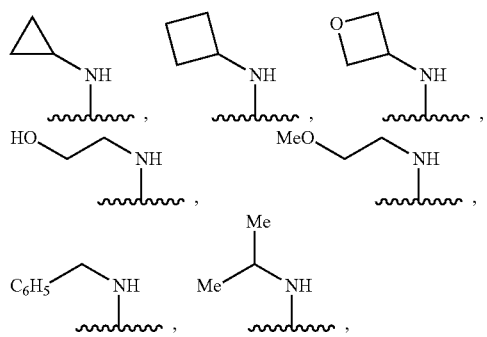

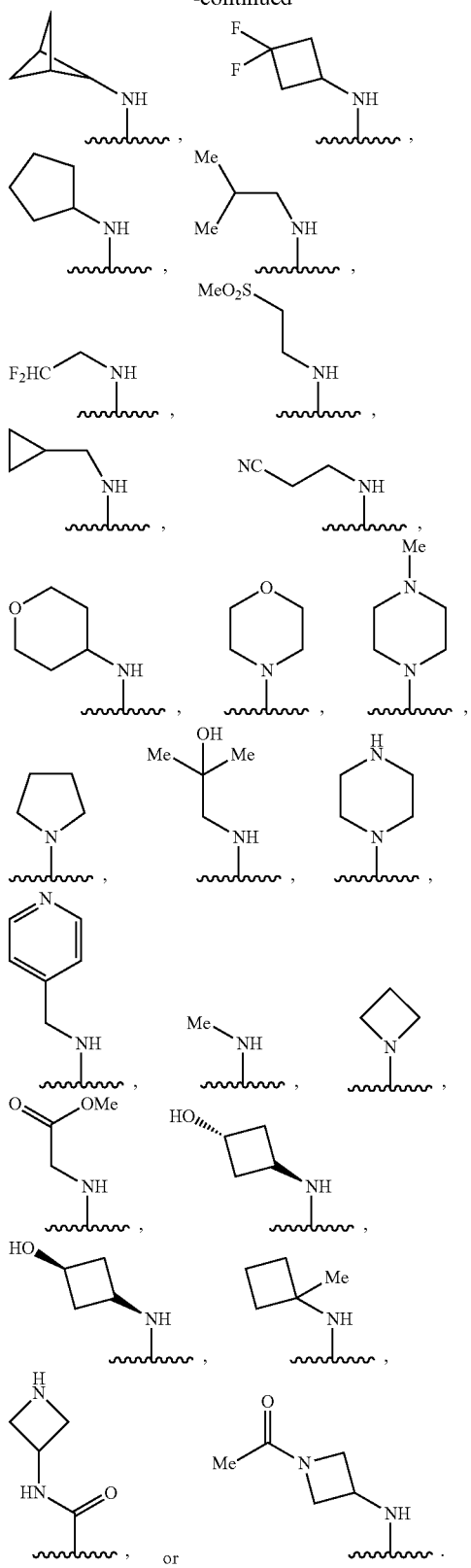

5. A compound according to claim 1, having an EC₅₀ of 50 nM or less in the HEK-Blue TLR7 Reporter Assay and 50 nm or less in the IL-6 Induction Assay.

6. A compound according to claim 1, which is PEGylated.

7. A compound according to claim 1, having a structure represented by formula (II)
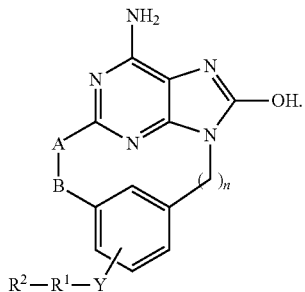
8. A compound according to claim 7, wherein n is 1.
9. A compound according to claim 8, wherein -A-B— is
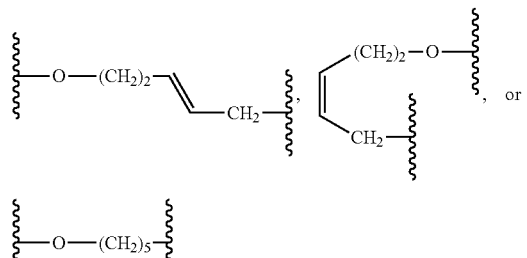
10. A compound according to claim 8, wherein Y is O, NH, or a bond.
11. A compound according to claim 8, wherein $R^1$ is not absent and $R^2$ is $(CH_2)_{1-2}NHR^3$, where $R^3$ is OH, Cl,
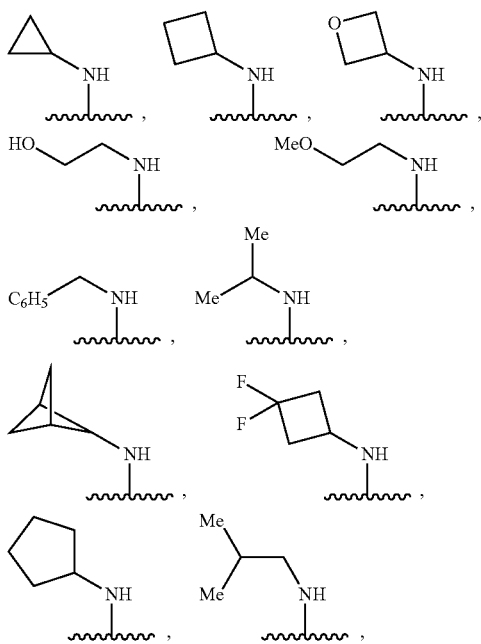
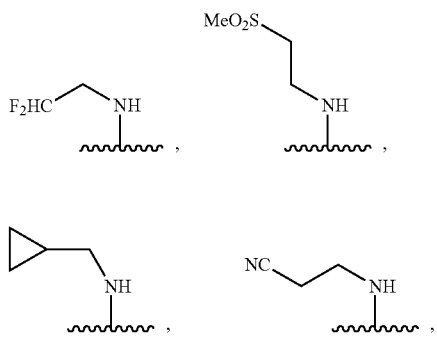
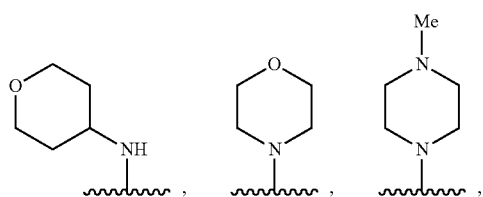
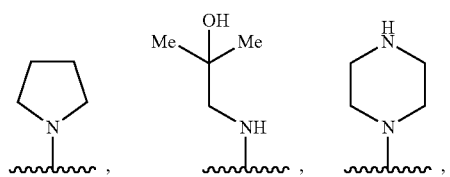
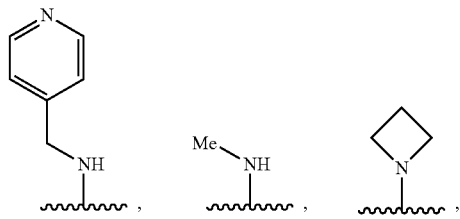
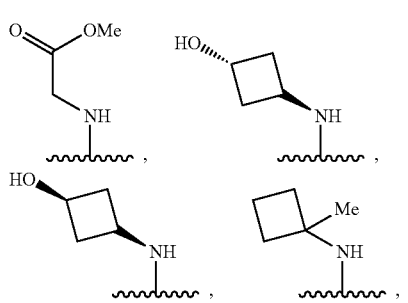
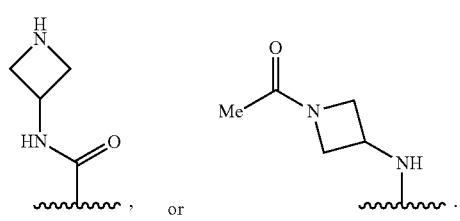

12. A compound according to claim 1, having a structure represented by formula (IIa)

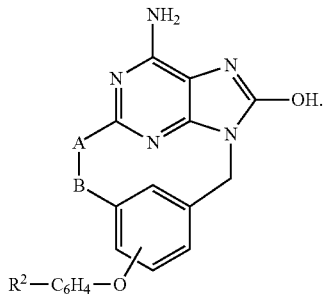

(IIa)

13. A compound according to claim 1, having a structure represented by formula (IIb)

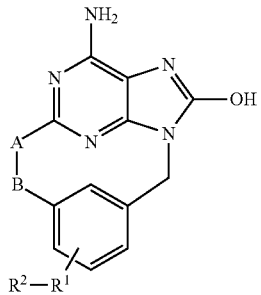

(IIb)

wherein $R^1$ is a phenyl, 6-membered heteroaromatic, or 5-membered heteroaromatic moiety.

14. A compound according to claim 13, wherein $R^1$ is

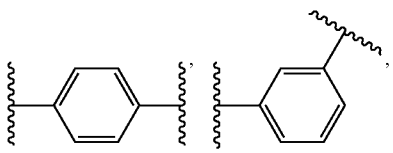

,

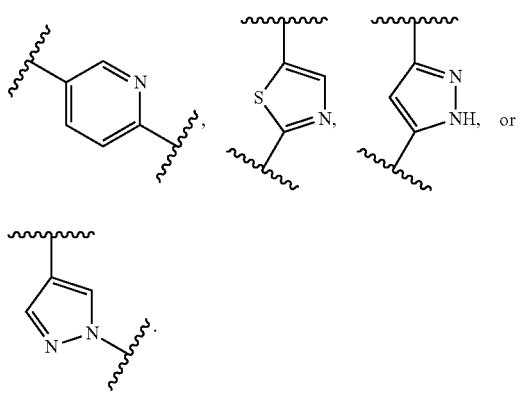

or

15. A compound according to claim 13, wherein $R^1$ is

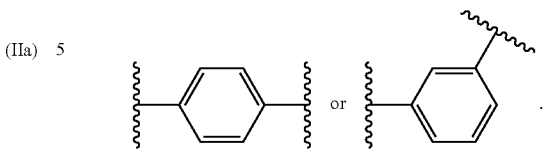

16. A compound according to claim 1, having a structure represented by formula (IIc):

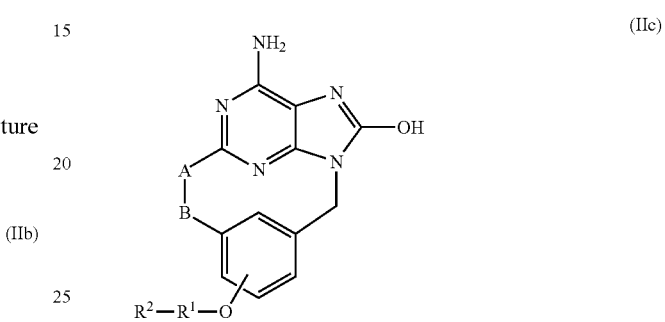

(IIc)

wherein $R^1$ is a 4- to 7-membered heterocycloaliphatic moiety.

17. A compound according to claim 1, having a structure represented by formula (IId):

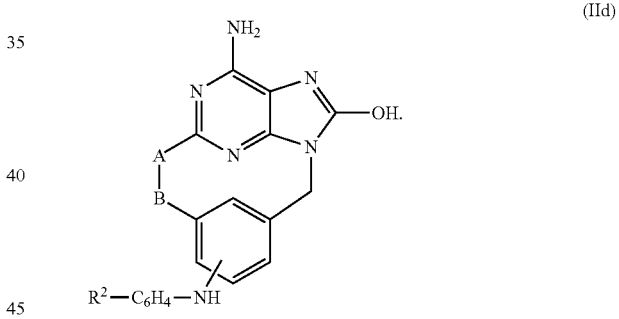

(IId)

18. A compound according to claim 1, having a structure represented by formula (IIe):

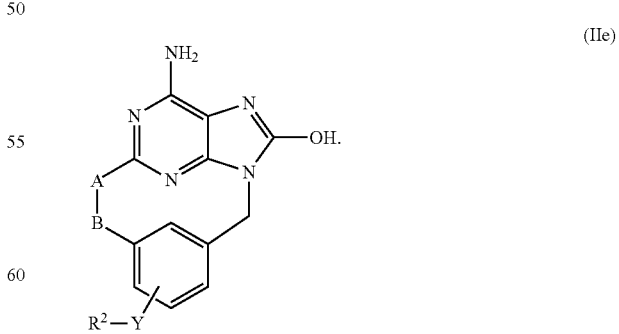

(IIe)

* * * * *